US012728156B2

(12) United States Patent
Subramanian et al.

(10) Patent No.: US 12,728,156 B2

(45) Date of Patent: Sep. 8, 2026

(54) TUMOR CELL-DERIVED EXOSOMES AND METHOD OF TREATING COLORECTAL CANCER

(71) Applicant: REGENTS OF THE UNIVERSITY OF MINNESOTA, Minneapolis, MN (US)

(72) Inventors: Subbaya Subramanian, Minneapolis, MN (US); Xianda Zhao, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 458 days.

(21) Appl. No.: 17/150,571

(22) Filed: Jan. 15, 2021

(65) Prior Publication Data

US 2021/0220456 A1 Jul. 22, 2021

Related U.S. Application Data

(60) Provisional application No. 62/962,312, filed on Jan. 17, 2020.

(51) Int. Cl.

*A61K 39/00* (2006.01)
*A61K 40/46* (2025.01)
*A61K 45/06* (2006.01)
*A61P 35/00* (2006.01)

(52) U.S. Cl.

CPC .......... *A61K 39/0011* (2013.01); *A61K 40/46* (2025.01); *A61K 45/06* (2013.01); *A61P 35/00* (2018.01)

(58) Field of Classification Search

CPC A61K 39/0011; A61K 45/06; A61K 2039/55; A61P 35/00; C12N 2310/141

See application file for complete search history.

(56) References Cited

PUBLICATIONS

Dai et al., miR-424-5p promotes the proliferation and metastasis of colorectal cancer by directly targeting SCN4B, ePub 2019, Pathology, Research and Practice, vol. 216, pp. 1-9 (Year: 2019).*

Choo et al., M1 Macrophage-Derived Nanovesicles Potentiate the Anticancer Efficacy of Immune Checkpoint Inhibitors, 2018, ACS Nano, vol. 12, pp. 8977-8993 (Year: 2018).*

Koyama et al., Exosomes derived from tumor cells genetically modified to express *Mycobacterium tuberculosis* antigen: a novel vaccine for cancer therapy, 2016, Biotechnology Letters, vol. 38, pp. 1857-1866 (Year: 2016).*

Kitdumrongthum et al., Dysregulated microRNA expression profiled in cholangiocarcinoma cell-derived exosomes, 2018, Life Sciences, vol. 210, pp. 65-75 (Year: 2018).*

Mousavi et al., Tumor-derived exosomes: Potential biomarkers and therapeutic target in the treatment of colorectal cancer, 2017, Journal of Cellular Physiology, vol. 234, pp. 12422-12432 (Year: 2017).*

Sarvizadeh et al., Vaccines for colorectal cancer: an update, 2018, Journal of Cellular Biochemistry, vol. 120, pp. 8815-8828 (Year: 2018).*

Torres et al., Combined miRNA profiling and proteomics demonstrates that different miRNAs target a common set of proteins to promote colorectal cancer metastasis, 2017, Journal of Pathology, vol. 242, pp. 39-51 (Year: 2017).*

Singh, N.P., et al. (2003). A novel approach to cancer immunotherapy: tumor cells decorated with CD80 generate effective antitumor immunity. Cancer Res. 63, 4067-4073.

Song, M.K., et al. (2013). 5-Fluorouracil-induced changes of intestinal integrity biomarkers in BALB/c mice. Journal of cancer prevention 18, 322-329.

Subramanian, S. Extracellular Vesicles Mediated Tumor-cell Intrinsic Immune Evasion in Colorectal Cancer. Presentaton at ISEV MRS 2019. Aug. 2, 2019. 27 pages.

Tesniere, A., et al. (2010). Immunogenic death of colon cancer cells treated with oxaliplatin. Oncogene 29, 482-491.

Toki, M.I., et al. (2020). Benign lymph node microenvironment is associated with response to immunotherapy. Precision Clin. Med. 3, 44-53.

Topalian, S.L., et al. (2012). Safety, activity, and immune correlates of anti-PD-1 antibody in cancer. N. Engl. J. Med. 366, 2443-2454.

Tuveson et al. Cancer modeling meets human organoid technology: Science vol. 364, Issue 6444, Jun. 7, 2019.

Vallejo, A.N., et al. (1999). Modulation of CD28 expression: distinct regulatory pathways during activation and replicative senescence. J. Immunol. 162, 6572-6579.

Veglia, F., et al. (2018). Myeloid-derived suppressor cells coming of age. Nat. Immunol. 19, 108-119.

Vincent, J., et al. (2010). 5-Fluorouracil selectively kills tumor-associated myeloid-derived suppressor cells resulting in enhanced T cell-dependent antitumor immunity. Cancer Res. 70, 3052-3061.

Wang, N., et al. (2018). A Cisplatin-loaded immunochemotherapeutic nanohybrid bearing immune checkpoint inhibitors for enhanced cervical cancer therapy. Angew. Chem. 57, 3426-3430.

Watanabe, S., et al. (2008). Tumor-induced CD11b+Gr-1+ myeloid cells suppress T cell sensitization in tumor-draining lymph nodes. J. Immunol. 181, 3291-3300.

Wu, X., et al. (2014). PD-1(+) CD8(+) T cells are exhausted in tumours and functional in draining lymph nodes of colorectal cancer patients. Br. J. Cancer 111, 1391-1399.

Zhang, L., et al. (2008). Differential impairment of regulatory T cells rather than effector T cells by paclitaxelbased chemotherapy. Clin. Immunol. 129, 219-229.

Zhang, Y., et al. "Exosomes derived from IL-12-anchored renal cancer cells increase induction of specific antitumor response in vitro: a novel vaccine for renal cell carcinoma." International journal of oncology 36.1 (2010): 133-140.

(Continued)

*Primary Examiner* — Jeffrey Stucker
*Assistant Examiner* — Brittney E Donoghue
(74) *Attorney, Agent, or Firm* — QUARLES & BRADY LLP

(57) ABSTRACT

The present invention provides tumor-derived extracellular vesicles (EVs) lacking an immune suppressive factor, for example, miR-424, methods of making and methods of use for treating cancer. Further the present invention provide vaccine compositions comprising modified tumor-derived EVs for use in treating secondary tumors.

11 Claims, 44 Drawing Sheets
(41 of 44 Drawing Sheet(s) Filed in Color)

Specification includes a Sequence Listing.

(56) References Cited

PUBLICATIONS

Zhao, X., et al. "Chemotherapy but not the tumor draining lymph nodes determine the immunotherapy response in secondary tumors." Iscience 23.5 (May 2020): 101056.
Zhao, X., et al. "Tumor location impacts immune response in mouse models of colon cancer." Oncotarget 8.33 (2017): 54775.
Zhao, X., et al. (2017). Intrinsic resistance of solid tumors to immune checkpoint blockade therapy. Cancer Res. 77, 817-822.
Beyranvand Nejad, E., et al. (2016). Tumor eradication by Cisplatin is sustained by CD80/86-mediated costimulation of CD8+ T cells. Cancer Res. 76, 6017-6029.
Buchan, S.L., et al. (2018). Antibodies to costimulatory receptor 4-1BB enhance anti-tumor immunity via T regulatory cell depletion and promotion of CD8 T cell effector function. Immunity 49, 958-970.e7.
Cao, Z., et al. (2014). Antitumor and immunomodulatory effects of low-dose 5-FU on hepatoma 22 tumor-bearing mice. Oncol. Lett. 7, 1260-1264.
Chambers, B.J., et al. (1996). Triggering of natural killer cells by the costimulatory molecule CD80 (B7-1). Immunity 5, 311-317.
Chester, C., et al. (2016). 4-1BB agonism: adding the accelerator to cancer immunotherapy. Cancer Immunol. Immunother. 65, 1243-1248.
Cochran, A.J., et al. (2001). Sentinel lymph nodes show profound downregulation of antigen-presenting cells of the paracortex: implications for tumor biology and treatment. Mod. Pathol. 14, 604-608.
Cochran, A.J., et al. (2006). Tumourinduced immune modulation of sentinel lymph nodes. Nat. Rev. Immunol. 6, 659-670.
Dai, W., et al. "miR-424-5p promotes the proliferation and metastasis of colorectal cancer by directly targeting SCN4B." Pathology—Research and Practice 216.1 (2020): 152731.
Devita, V.T., Jr., et al. (2008). A history of cancer chemotherapy. Cancer Res. 68, 8643-8653.
Emens, L.A., et al. (2015). The interplay of immunotherapy and chemotherapy: harnessing potential synergies. Cancer Immunol. Res. 3, 436-443.
Fend, L., et al. (2017). Immune checkpoint blockade, immunogenic chemotherapy or IFN-alpha blockade boost the local and abscopal effects of oncolytic virotherapy. Cancer Res. 77, 4146-4157.
Fisher, B., et al. (1971). Studies concerning the regional lymph node in cancer. I. Initiation of immunity. Cancer 27, 1001-1004.
Fransen, M.F., et al. (2018). Tumordraining lymph nodes are pivotal in PD-1/PD-L1 checkpoint therapy. JCI Insight 3, 124507.
Galluzzi, L., et al. (2017). Immunogenic cell death in cancer and infectious disease. Nat. Rev. Immunol. 17, 97-111.
Genbank. Genbank Gene ID 494336. Version updated Jun. 4, 2019. Available online at https://web.archive.org/web/20190608190615/https://www.ncbi.nlm.nih.gov/gene/494336.
Ghiringhelli, F., et al. (2007). Metronomic cyclophosphamide regimen selectively depletes CD4+CD25+ regulatory T cells and restores T and NK effector functions in end stage cancer patients. Cancer Immunol. Immunother. 56, 641-648.
Gide, T.N., et al. (2018). Primary and acquired resistance to immune checkpoint inhibitors in metastatic melanoma. Clin. Cancer Res. 24, 1260-1270.
International Searching Authority. International Search Report and Written Opinion for application PCT/US2021/013657. Mailed on May 26, 2021. 12 pages.
Ito, M., et al. (2006). Tumor-derived TGFbeta-1 induces dendritic cell apoptosis in the sentinel lymph node. J. Immunol. 176, 5637-5643.
Jeanbart, L., et al. (2014). Enhancing efficacy of anticancer vaccines by targeted delivery to tumor-draining lymph nodes. Cancer Immunol. Res. 2, 436-447.
Jennings et al. Adjuvants and Delivery Systems for Viral Vaccines-Mechanisms and Potential. In: Brown F, Haaheim LR, (eds). Modulation of the Immune Response to Vaccine Antigens. Dev. Biol. Stand, vol. 92. Basel: Karger 1998; 19-28.
Kamphorst, A.O., et al. (2017). Rescue of exhausted CD8 T cells by PD-1-targeted therapies is CD28-dependent. Science 355, 1423-1427.
Kareva, I. (2017). A combination of immune checkpoint inhibition with metronomic chemotherapy as a way of targeting therapyresistant cancer cells. Int. J. Mol. Sci. 18, E2134.
Karlsson, M., et al. (2010). Pilot study of sentinel-node-based adoptive immunotherapy in advanced colorectal cancer. Ann. Surg. Oncol. 17, 1747-1757.
Khosravianfar, N., et al. (2018). Myeloid-derived suppressor cells elimination by 5-fluorouracil increased dendritic cell-based vaccine function and improved immunity in tumor mice. Iran. J. Allergy Asthma Immunol. 17, 47-55.
Kumar, V., et al. (2016). The nature of myeloidderived suppressor cells in the tumor microenvironment. Trends Immunol. 37, 208-220.
Lake, R.A., et al. (1993). CD28 mRNA rapidly decays when activated T cells are functionally anergized with specific peptide. Int. Immunol. 5, 461-466.
Lanier, L.L., et al. (1995). CD80 (B7) and CD86 (B70) provide similar costimulatory signals for T cell proliferation, cytokine production, and generation of CTL. J. Immunol. 154, 97-105.
Le, D.T., et al. (2017). Mismatch repair deficiency predicts response of solid tumors to PD-1 blockade. Science 357, 409-413.
Lee, C.K., et al. (2017). Checkpoint inhibitors in metastatic EGFR-mutated non-small cell lung cancer—a meta-analysis. J. Thorac. Oncol. 12, 403-407.
Linterman, M.A., et al. (2014). CD28 expression is required after T cell priming for helper T cell responses and protective immunity to infection. Elife 3, e03180.
Liu, J., et al. (2016). Improved efficacy of neoadjuvant compared to adjuvant immunotherapy to eradicate metastatic disease. Cancer Discov. 6, 1382-1399.
Lutsiak, M.E., et al. (2005). Inhibition of CD4(+)25+ T regulatory cell function implicated in enhanced immune response by low-dose cyclophosphamide. Blood 105, 2862-2868.
Marzo, A.L., et al. (1999). Tumor antigens are constitutively presented in the draining lymph nodes. J. Immunol. 162, 5838-5845.
Michels, T., et al. (2012). Paclitaxel promotes differentiation of myeloid-derived suppressor cells into dendritic cells in vitro in a TLR4-independent manner. J. Immunotoxicology 9, 292-300.
Mirbase. miRBase accession MI0001446. Stem-loop sequence hsa-mir-424. Versino dated Nov. 2, 2017. Available online at https://web.archive.org/web/20171102061909/https://www.mirbase.org/cgi-bin/mirna_entry.pl?acc=MI0001446.
Munn, D.H., et al. (2006). The tumordraining lymph node as an immune-privileged site. Immunol. Rev. 213, 146-158.
Murthy, V., et al. (2019). Tumor-draining lymph nodes demonstrate a suppressive immunophenotype in patients with non-small cell lung cancer assessed by endobronchial ultrasound-guided transbronchial needle aspiration: a pilot study. Lung Cancer 137, 94-99.
Natasha, G., et al. "Exosomes as immunotheranostic nanoparticles." Clinical therapeutics 36.6 (2014): 820-829.
Petrovsky, N. et al. "Vaccine adjuvants: Current state and future trends." Immunology and Cell Biology 82 (2004): 488-496.
Pfirschke, C., et al. (2016). Immunogenic chemotherapy sensitizes tumors to checkpoint blockade therapy. Immunity 44, 343-354.
Rizvi, N.A., et al. (2015). Activity and safety of nivolumab, an anti-PD-1 immune checkpoint inhibitor, for patients with advanced, refractory squamous non-smallcell lung cancer (CheckMate 063): a phase 2, single-arm trial. Lancet Oncol. 16, 257-265.
Robert, C., et al. (2011). Ipilimumab plus dacarbazine for previously untreated metastatic melanoma. N. Engl. J. Med. 364, 2517-2526.
Samanta, D., et al. (2018). Chemotherapy induces enrichment of CD47(+)/ CD73(+)/PDL1(+) immune evasive triple-negative breast cancer cells. Proc. Natl. Acad. Sci. U S A 115, E1239-E1248.
Sato, T., et al. "Long-term expansion of epithelial organoids from human colon, adenoma, adenocarcinoma, and Barrett's epithelium." Gastroenterology 141.5 (2011): 1762-1772.
Sayers, S., et al. "Vaxjo: a web-based vaccine adjuvant database and its application for analysis of vaccine adjuvants and their uses in vaccine development." Journal of Biomedicine and Biotechnology 2012 (2012).

(56) References Cited

PUBLICATIONS

Scrimieri, F., et al. (2013). Murine leukemia virus envelope gp70 is a shared biomarker for the high-sensitivity quantification of murine tumor burden. Oncoimmunology 2, e26889.
Sharma, P., et al. (2017). Primary, adaptive, and acquired resistance to cancer immunotherapy. Cell 168, 707-723.
Shu, S., et al. (2006). Immune responses in the draining lymph nodes against cancer: implications for immunotherapy. Cancer Metastasis Rev. 25, 233-242.
Shuang, Z.-Y., et al. (2017). The tumor-draining lymph nodes are immunosuppressed in patients with hepatocellular carcinoma. Transl. Cancer Res. 6, 1188-1196.

* cited by examiner

E

Fig. 4A-4C
A
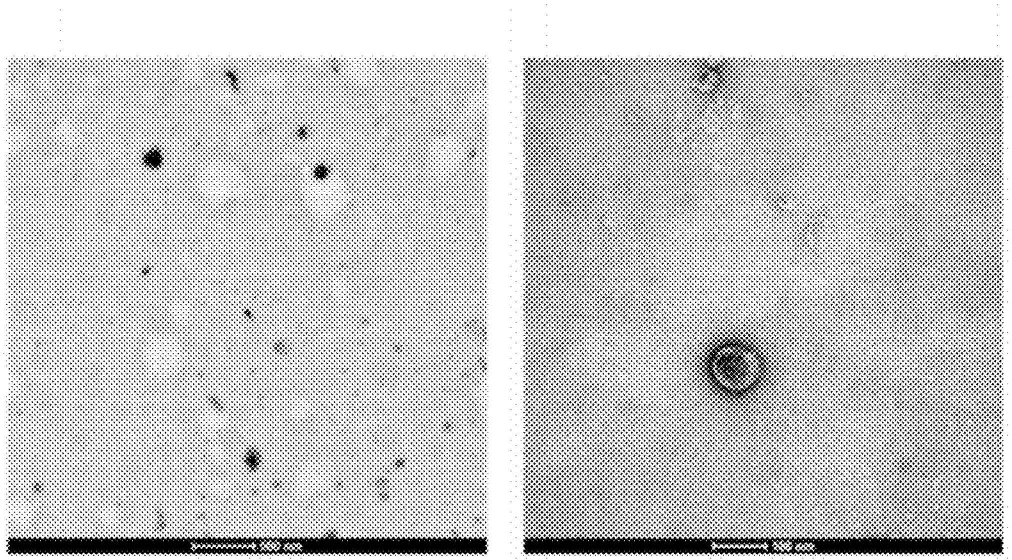
B
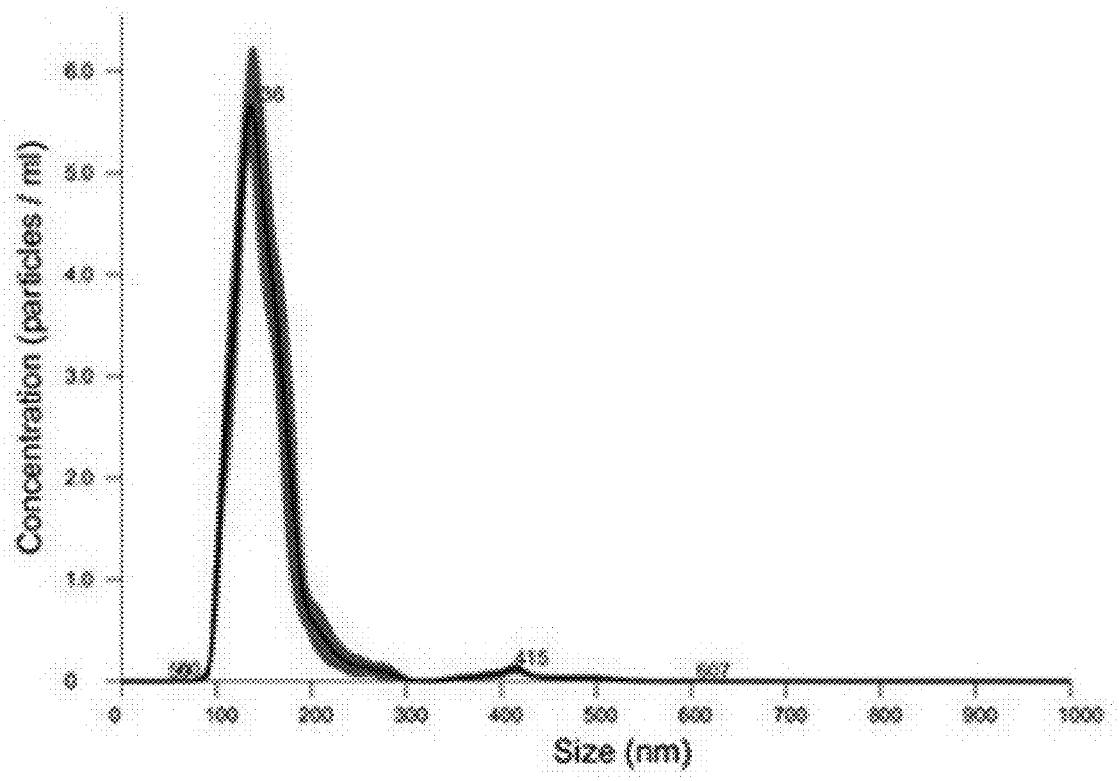

E-H

FIGS. 20A-20K (continued)
I
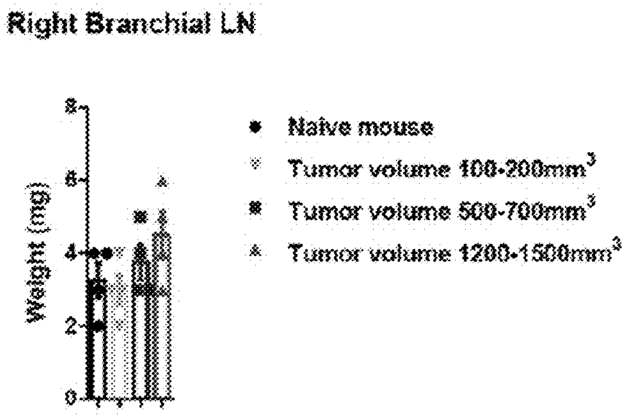
J
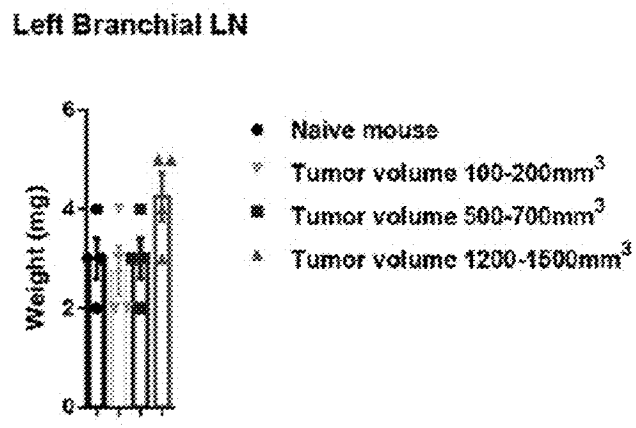
K
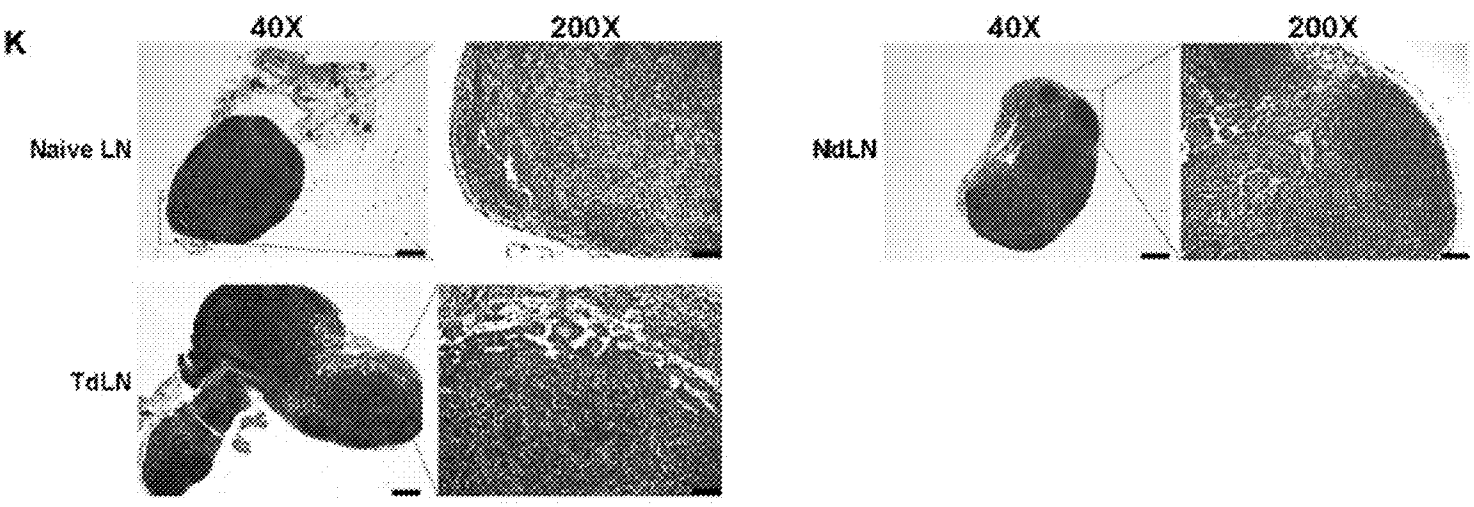

SEQUENCE LISTING

```
<160> NUMBER OF SEQ ID NOS: 27

<210> SEQ ID NO 1
<211> LENGTH: 22
<212> TYPE: RNA
<213> ORGANISM: Homo sapiens

<400> SEQUENCE: 1

cagcagcaau ucauguuuug aa                                              22


<210> SEQ ID NO 2
<211> LENGTH: 22
<212> TYPE: RNA
<213> ORGANISM: Mus musculus

<400> SEQUENCE: 2

cagcagcaau ucauguuuug ga                                              22


<210> SEQ ID NO 3
<211> LENGTH: 20
<212> TYPE: RNA
<213> ORGANISM: Homo sapiens
```

<400> SEQUENCE: 3
uuggccaugg ggcugcgcgg 20

<210> SEQ ID NO 4
<211> LENGTH: 124
<212> TYPE: RNA
<213> ORGANISM: Homo sapiens

<400> SEQUENCE: 4
aacccuccuu gggaagugaa gcucaggcug ugauuucaag ccagggggcg uuuuucuaua 60
acuggaugaa aagcaccucc agagcuugaa gcucacaguu ugagagcaau cgucuaagga 120
aguu 124

<210> SEQ ID NO 5
<211> LENGTH: 83
<212> TYPE: RNA
<213> ORGANISM: Homo sapiens

<400> SEQUENCE: 5
ccuuggagua aaguagcagc acauaauggu uuguggauuu ugaaaaggug caggccauau 60
ugugcugccu caaaaauaca agg 83

<210> SEQ ID NO 6
<211> LENGTH: 89
<212> TYPE: RNA
<213> ORGANISM: Homo sapiens

<400> SEQUENCE: 6
gucagcagug ccuuagcagc acguaaauau uggcguuaag auucuaaaau uaucuccagu 60
auuaacugug cugcugaagu aagguugac 89

<210> SEQ ID NO 7
<211> LENGTH: 87
<212> TYPE: RNA
<213> ORGANISM: Homo sapiens

<400> SEQUENCE: 7
agcuucccug gcucuagcag cacagaaaua uuggcacagg gaagcgaguc ugccaauauu 60
ggcugugcug cuccaggcag gguggug 87

<210> SEQ ID NO 8
<211> LENGTH: 97
<212> TYPE: RNA
<213> ORGANISM: Homo sapiens

<400> SEQUENCE: 8
cacucugcug uggccuaugg cuuuucauuc cuaugugauu gcugucccaa acucauguag 60
ggcuaaaagc caugggcuac agugaggggc gagcucc 97

<210> SEQ ID NO 9
<211> LENGTH: 87
<212> TYPE: RNA
<213> ORGANISM: Homo sapiens

<400> SEQUENCE: 9
cagacguguc auccccagau acaauggaca auaugcuauu auaaucguau ggcauugucc 60
uugcuguuug gagauaauac ugcugac 87

-continued

<210> SEQ ID NO 10
<211> LENGTH: 99
<212> TYPE: RNA
<213> ORGANISM: Homo sapiens

<400> SEQUENCE: 10
ccgaugugua uccucagcuu ugagaacuga auuccauggg uugugucagu gucagaccuc 60
ugaaauucag uucuucagcu gggauaucuc ugucaucgu 99

<210> SEQ ID NO 11
<211> LENGTH: 119
<212> TYPE: RNA
<213> ORGANISM: Homo sapiens

<400> SEQUENCE: 11
aggauucugc ucaugccagg gugagguagu aaguuguauu guuguggggu agggauauua 60
ggccccaauu agaagauaac uauacaacuu acuacuuucc cuggugugug gcauauuca 119

<210> SEQ ID NO 12
<211> LENGTH: 86
<212> TYPE: RNA
<213> ORGANISM: Homo sapiens

<400> SEQUENCE: 12
ugcucccucu cucacauccc uugcauggug gagggugagc uuucugaaaa ccccucccac 60
augcaggguu ugcaggaugg cgagcc 86

<210> SEQ ID NO 13
<211> LENGTH: 68
<212> TYPE: RNA
<213> ORGANISM: Homo sapiens

<400> SEQUENCE: 13
cccucgucuu acccagcagu guuugggugc gguugggagu cucuaauacu gccggguaau 60
gauggagg 68

<210> SEQ ID NO 14
<211> LENGTH: 90
<212> TYPE: RNA
<213> ORGANISM: Homo sapiens

<400> SEQUENCE: 14
ccgggccccu gugagcaucu uaccggacag ugcuggauuu cccagcuuga cucuaacacu 60
gucugguaac gauguucaaa ggugacccgc 90

<210> SEQ ID NO 15
<211> LENGTH: 110
<212> TYPE: RNA
<213> ORGANISM: Homo sapiens

<400> SEQUENCE: 15
ccgcagagug ugacuccugu ucuguguaug gcacugguag aauucacugu gaacagucuc 60
agucagugaa uuaccgaagg gccauaaaca gagcagagac agauccacga 110

<210> SEQ ID NO 16
<211> LENGTH: 110
<212> TYPE: RNA
<213> ORGANISM: Homo sapiens

<400> SEQUENCE: 16

-continued

```
gagcugcuug ccucccccg uuuuuggcaa ugguagaacu cacacuggug agguaacagg     60

auccgguggu ucuagacuug ccaacuaugg ggcgaggacu cagccggcac              110


<210> SEQ ID NO 17
<211> LENGTH: 22
<212> TYPE: RNA
<213> ORGANISM: Homo sapiens

<400> SEQUENCE: 17

uagcuuauca gacugauguu ga                                              22


<210> SEQ ID NO 18
<211> LENGTH: 22
<212> TYPE: RNA
<213> ORGANISM: Artificial Sequence
<220> FEATURE:
<223> OTHER INFORMATION: Synthetic- anti-miR-424 oligo

<400> SEQUENCE: 18

uucaaaacau gaauugcugc ug                                              22


<210> SEQ ID NO 19
<211> LENGTH: 22
<212> TYPE: DNA
<213> ORGANISM: Artificial Sequence
<220> FEATURE:
<223> OTHER INFORMATION: Synthetic- hsa-miR-424-5p guide RNA

<400> SEQUENCE: 19

cagcagcaat tcatgttttg aa                                              22


<210> SEQ ID NO 20
<211> LENGTH: 22
<212> TYPE: DNA
<213> ORGANISM: Artificial Sequence
<220> FEATURE:
<223> OTHER INFORMATION: Synthetic- mmu-miR-322-5p guide RNA

<400> SEQUENCE: 20

cagcagcaat tcatgttttg ga                                              22


<210> SEQ ID NO 21
<211> LENGTH: 20
<212> TYPE: DNA
<213> ORGANISM: Artificial Sequence
<220> FEATURE:
<223> OTHER INFORMATION: Synthetic- U6 snRNA primer

<400> SEQUENCE: 21

aaggatgaca cgcaaattcg                                                 20


<210> SEQ ID NO 22
<211> LENGTH: 20
<212> TYPE: DNA
<213> ORGANISM: Artificial Sequence
<220> FEATURE:
<223> OTHER INFORMATION: Synthetic- 18S rRNA forward primer

<400> SEQUENCE: 22

gttggttttc ggaactgagg                                                 20


<210> SEQ ID NO 23
<211> LENGTH: 20
<212> TYPE: DNA
```

-continued

```
<213> ORGANISM: Artificial Sequence
<220> FEATURE:
<223> OTHER INFORMATION: Synthetic- 18S rRNA reverse primer

<400> SEQUENCE: 23

agtcggcatc gtttatggtc                                                20


<210> SEQ ID NO 24
<211> LENGTH: 20
<212> TYPE: DNA
<213> ORGANISM: Artificial Sequence
<220> FEATURE:
<223> OTHER INFORMATION: Synthetic- gp70 forward primer

<400> SEQUENCE: 24

aaagtgacac atgcccacaa                                                20


<210> SEQ ID NO 25
<211> LENGTH: 20
<212> TYPE: DNA
<213> ORGANISM: Artificial Sequence
<220> FEATURE:
<223> OTHER INFORMATION: Synthetic- gp70 reverse primer

<400> SEQUENCE: 25

ccccaagagg cacaatagaa                                                20


<210> SEQ ID NO 26
<211> LENGTH: 9
<212> TYPE: PRT
<213> ORGANISM: Artificial Sequence
<220> FEATURE:
<223> OTHER INFORMATION: Synthetic- Murine leukemia virus epitope used
      in H-2Ld MuLV gp70 Tetramer

<400> SEQUENCE: 26

Ser Pro Ser Tyr Val Tyr His Gln Phe
1               5


<210> SEQ ID NO 27
<211> LENGTH: 9
<212> TYPE: PRT
<213> ORGANISM: Artificial Sequence
<220> FEATURE:
<223> OTHER INFORMATION: Synthetic- Influenza A virus epitope used in
      Influenza HA Tetramer

<400> SEQUENCE: 27

Ile Tyr Ser Thr Val Ala Ser Ser Leu
1               5
```

TUMOR CELL-DERIVED EXOSOMES AND METHOD OF TREATING COLORECTAL CANCER

CROSS-REFERENCE TO RELATED APPLICATIONS

This application claims priority to U.S. Provisional Application No. 62/962,312 filed on Jan. 17, 2020, the contents of which are incorporated by reference in its entirety.

STATEMENT REGARDING FEDERALLY SPONSORED RESEARCH

N/A

BACKGROUND OF THE INVENTION

Colorectal cancer (CRC) remains the third most common cause of cancer-related deaths in the United States. Approximately 85% of CRC tumors are nonimmunogenic (i.e. they lack a significant number of tumor-infiltrating T cells) and are typically unresponsive to current immune checkpoint inhibitor-based therapies. Tumor-derived exosomes (or extracellular vesicles (EVs)) have been identified as a major source of tumor antigens that can stimulate tumor-specific immunity. However, immunosuppressive factors, such as PD-L1 and miRNAs that target T-cell activation, were also identified in the tumor-derived EVs. It has been shown that these immunosuppressive components compromise the tumor immunity stimulating effects of tumor-derived EVs, leading to immunosuppression in the cancer patients.

Thus, there is a need in the art for compositions and methods for increasing the immune response to tumors and for increasing the efficacy of checkpoint blockades for cancer treatment.

SEQUENCE LISTING

A Sequence Listing accompanies this application and is submitted as an ASCII text file of the sequence listing named "920171_00394_ST25.txt" which is 5.94 KB in size and was created on Jan. 14, 2021. The sequence listing is electronically submitted via EFS-Web with the application and is incorporated herein by reference in its entirety.

SUMMARY OF THE INVENTION

In some aspects, the present disclosure provides modified tumor-derived extracellular vesicles (EVs) isolated from a tumor cell having reduced or lacking expression of an immune suppressive factor. In a preferred embodiment, the immune suppressive factor is miR-424. These modified tumor-derived EVs may be used as a vaccine for treating tumors by increasing the immune response to the tumors, more particularly secondary tumors which which are distal to the primary tumor site.

In another aspect, the present disclosure provides a composition comprising one or more tumor-derived EVs and a pharmaceutically acceptable carrier. In some aspects, the two or more EVs are from the same tumor type.

In another aspect, the present disclosure provides a method of producing a tumor-derived extracellular vesicle (EV) substantially lacking expression of an immune suppressive factor, preferably miR-424, the method comprising (a) providing a modified tumor cell that lacks expression of the immune suppressive factor and can produce EVs; and (b) isolating EVs produced by the tumor cell, wherein the EVs substantially lack expression of the immune suppressive factor, preferably miR-424.

In another aspect, the present disclosure provides a method of treating cancer in a subject comprising administering an effective amount of tumor-derived EVs to a subject in need thereof. The EVs should substantially lack expression of an immune suppressive factor or miR-424 and should comprise one or more cancer antigen.

In yet another aspect, the present disclosure provides a method of stimulating an anti-tumor response in a subject having cancer. The method involves administering a vaccine comprising tumor-derived EVs described herein or the composition described herein to a subject having cancer in an amount effective to elicit an anti-tumor response in the subject.

In another aspect, the present disclosure provides a method of sensitizing a tumor cell in a subject to immune checkpoint inhibitors. The method involves administering one or more tumor-derived EVs described herein or the composition described herein to a subject having cancer and subsequently administering one or more checkpoint inhibitors to the subject. In some aspects, the checkpoint inhibitor is a PD-1 inhibitor, a PD-L1 inhibitor, a CTLA-4 inhibitor or combinations thereof.

In another aspect, the present disclosure provides a method of preventing, reducing or inhibiting tumor cell growth in a subject. The method involves administering an effective amount of a vaccine comprising tumor-derived EVs to a subject in need thereof to prevent, reduce, or inhibit tumor cell growth. The EVs should substantially lack expression of an immune suppressive factor or miR-424. In some aspects, the cancer to be inhibited is adenocarcinoma from an adenoma.

In another aspect, the present disclosure provides a method of preventing the growth of a secondary tumor in a subject following resection of a primary tumor. The method involves administering an effective amount of a vaccine comprising tumor-derived EVs to the subject. The EVs should substantially lack expression of an immune suppressive factor or miR-424.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 1A, T-cell infiltration (CD3) was evaluated in human colorectal cancer (CRC) patients' samples using immunofluorescent staining. The bar graph below depicts the total number of cases of microsatellite stable (MSS) subtype CRC tumors and microsatellite instability (MSI) subtype CRC tumors that exhibited high T-cell infiltration and low T-cell infiltration in this assay. In FIG. 1B, expression of CD28 was measured on $CD4^+$ T-cells and $CD8^+$ T-cells, and expression of CD80 and CD86 was measured on DCs by performing flow cytometry on CRC colon tissues and paired normal colon tissues. In FIG. 1C, the results of FIG. 1B were confirmed by performing immunofluorescent staining. Assayed markers include: CD28 expression on CRC tumor infiltrating T-cells (left), CD80 expression on CRC tumor infiltrating CD11c+ cells (middle), and CD86 expression on CRC tumor infiltrating CD11c+ cells (right). FIG. 1D shows tumor growth in wild-type mice, CD28 knockout mice, and CD80/86 knockout mice treated with anti-CTLA-4 in combination with anti-PD-1, with or without antibody that blocks CD80 and CD86.

FIG. 2A is a schematic depicting the process used to identify miRNAs that might downregulate CD28 and CD80. FIG. 2B is a scatterplot showing miR-424 expression levels in CRC and normal colon samples, using data from the TCGA database. FIG. 2C shows the results of an in situ hybridization (ISH) experiment, which confirm that miR-424 is expressed in CRC tumor cells. FIG. 2D is a heatmap comparing the miR-424 expression levels (as measured by qPCR) in paired samples (from the same patients) from CRC and normal colon cases. FIG. 2F shows the levels of CD28 and CD80 protein in T-cells and DCs transfected with either a miR-424 mimic or a scrambled control miR sequence, as measured by flow cytometry. FIG. 2G shows a heatmap depicting the expression levels of various immune markers on various cell types during tumor growth.

FIG. 3A shows a heatmap depicting the relative levels of miR-424 in different cells and EVs. FIG. 3B shows Dio labeled EVs within T-cells and DCs. FIG. 3C shows bar graphs depicting the levels of miR-422 expression measured in T-cells (left) and DCs (right) co-cultured with CT26 cells. GW4869 was used to block EV production in the co-culture systems. FIG. 3D shows the GFP signal that was detected in tumor infiltrating T-cells and DCs by flow cytometry, demonstrating that tumor cell-derived EVs (expressing GFP) were engulfed by these cells. FIG. 3E shows bar graphs depicting the miR-424 expression levels in T-cells and DCs isolated from wild-type tumors, miR-424 knockout tumors, or naïve mouse spleen. FIG. 3F shows bar graphs depicting the levels of CD28 expression on Jurkat cells (left) and CD80 expression on Raji cells (right) in tumors treated with wild-type EVs, miRi control EVs, or inactivated miR-424 (miR-424i). FIG. 3G shows a bar graph depicting IL-2 production from Jurkat cells and Raji cells co-cultured with human CRC derived organoids.

FIG. 4A shows transmission electron microscopy images of EVs isolated from CT26 tumor cells. FIG. 4B shows the size distribution of EVs isolated from CT26 tumor cells, as measured by the Nanosight system. FIG. 4C shows the levels of CD9 (left) and CD63 (right) protein expression detected on the surface of EVs isolated from CT26 tumor cells by flow cytometry.

FIG. 5A shows the levels of EV production from tumor cell after knock down of Rab27a. FIG. 5B shows tumor growth after knock down of Rab27a. FIG. 5C shows the growth of tumors that do not express endogenous miR-424 after treatment with exogenous tumor-derived EVs that express miR-424. FIG. 5D shows tumor growth and survival in immune competent mice after inactivation (miR-424i) or depletion (miR-424KO) of tumor derived miR-424. FIG. 5E shows the levels of tumor specific CD8+ T-cells detected in tumor free mice that were injected with miR-424i CT26 tumor cells. FIG. 5F shows tumor growth in immune deficient mice after inactivation or depletion of tumor-derived miR-424. Below, levels of the proliferative marker (Ki-67) and apoptotic marker (Cleaved-Caspase-3) were measured in control tumors and tumors with inactivated miR-424. FIG. 5G shows gene expression in CT26 cells after inactivation of tumor cell-derived miR-424 based on mRNA-seq data. Below, the biological pathways that were up/down regulated are shown.

FIG. 6A shows MC38 tumor growth and survival in immune competent mice after inactivation (miR-424i) or depletion (miR-424KO) of tumor derived miR-424. FIG. 6B shows the levels of tumor specific CD8+ T-cells detected in tumor free mice that were injected with miR-424i MC38 tumor cells. FIGS. 6C-6D show gene expression in MC38 cells after inactivation of tumor cell-derived miR-424 based on mRNA-seq data. In FIG. 6D, biological pathways that were up regulated are shown. FIG. 6E shows volcano plots of the miRNA expression profiles of wild-type (WT), control (miRi-Ctrl), and miR-424 inactivated (miR-424i) cells.

FIG. 7A shows images depicting T-cell infiltration in CT26 tumors with inactivated miR-424 and control tumors. FIG. 7B shows a heatmap depicting the anti-tumor immune profiles of CT26 tumors with inactivated miR-424 and control tumors. FIG. 7C shows the levels of immune marker expression on various cells localized to tumor draining lymph nodes (TdLNs) and spleen (SPL). FIGS. 7D-7E shows the volume of CT26 tumors (FIG. 7D) and MC38 tumors (FIG. 7E) treated with ICBT, alone and in combination with inactivation of the tumor cell-derived miR-424.

FIG. 8A shows images depicting the T-cell infiltration in MC38 tumors with inactivated miR-424 and in control tumors. FIG. 8B is a heatmap showing the anti-tumor immune profiles of MC38 tumors with inactivated miR-424 and of control tumors. FIG. 8C shows the immune profiles of TdLNs and SPL in CT26 tumor-bearing mice. FIG. 8D shows the immune profiles of TdLNs and SPL in MC38 tumor bearing mice.

FIG. 9A shows the detection of GFP in T-cells or DCs collected from peripheral lymphatic organs after tumor cell-derived EVs (expressing GFP) were injected intravenously through the tail vein of mice. FIG. 9B shows the detection of indicators of T-cell expansion in the peripheral lymphatic organs after treatment with tumor cell-derived EVs with inactivated miR-424. FIG. 9C shows tumor volume and frequency in pre-conditioned naïve mice treated with tumor cell-derived EVs with inactivated (miR-424i-EV) or depleted (miR-424KO-EV) miR-424 in the MC38 (left) and CT26 (right) models. The effects were examined in wild-type (WT) mice, TLR4-KO mice, SCID mice, CD28KO mice, and CD80/86KO mice.

FIG. 10A shows the growth of mice after injection with tumor cell-derived EVs. FIG. 10B shows the D-dimer levels (an indicator of extensive thrombosis) in the serum of mice after injection with tumor cell-derived EVs. FIG. 10C shows the serum levels of cytokines in mice after injection with tumor cell-derived EVs. FIG. 10D shows a histological analysis by hematoxylin and eosin staining, demonstrating the lack of immune infiltration in major organs (spleen, lung, heart, liver, kidney, and small intestine) collected from mice after injection with tumor cell-derived EVs.

FIG. 11A shows a scan of advanced orthotopic cecum tumors in mice treated with ICBT, alone and in combination with tumor cell-derived EVs with inactivated miR-424. FIG. 11B shows the metastatic tumor burden after two weeks treatment with ICBT, alone and in combination with tumor cell-derived EVs with inactivated miR-424. FIG. 11C shows the survival after treatment with ICBT, alone and in combination with tumor cell-derived EVs with inactivated miR-424. FIG. 11D is a heatmap of the immune profiles of tumors treated by different therapies.

FIG. 12A shows images of primary tumors and liver metastatic lesions from the orthotopic cecum model (left) and the histology of primary tumors (right; 1: tumor cells submucosa; 2: tumor cells in muscularis externa; 3: tumor cells outside the colon wall; 4: tumor cells in mucosa; 5: liver tissue; 6: tumor cells spreading to the surface of liver; 7: tumor metastasis in the liver). FIG. 12B shows growth curves for individual tumors from mice in each treatment group. Mice that did not survive longer than 7 days after treatment are not shown. FIG. 12C shows the raw data and statistical analysis used to generate the heatmap shown in FIG. 11D.

FIG. 13A shows an experimental schedule and tumor growth curves in mice with or without TdLNs. Both CT26 (BALB/c mouse as the host) and MC38 (C57BL/6 mouse as the host) subcutaneous models were enrolled in the experiment. Mice were pre-conditioned by TdLNs resection (right inguinal and axillary LNs), NdLNs resection (left inguinal and axillary LNs), or sham surgery prior to tumor inoculation. Accelerated tumor growth was observed in mice without TdLNs (n=5 in each group, One-way ANOVA test between all groups, data represent each individual mouse, *p<0.05, p<0.01, *p<0.001). FIG. 13B shows the distribution of tumor antigen (gp70) specific CD8+ T cells in tumor-bearing mice with or without TdLNs. Less tumor antigen-specific CD8+ T cells was detected in right and left brachial lymph nodes and spleen of TdLNs resected tumor-bearing mice (n=4 in each group, Tukey's multiple comparisons test between two groups, data were displayed as means±SEMs, n.s.: no significance, p<0.01). FIG. 13C shows the experimental schedule and early-stage tumor response to anti-4-1BB treatment. Two injections of anti-4-1BB were given shortly after tumor inoculation. The treatment prevented tumor development in tumor-bearing mice with intact TdLNs. Rechallenge of the tumor cells did not form tumors in all anti-4-1BB cured mice (n=4 in each group, One-way ANOVA test between all groups, data represent each individual mouse, p<0.0001). See also FIGS. 19-21** and Table 2.

FIG. 14A shows the experimental schedule. Resection of TdLNs did not accelerate localized secondary tumor (mimicking recurrent tumor) development in both CT26 and MC38 subcutaneous tumor models. However, systemic deletion of T cells significantly accelerated secondary tumor development in both tumor models (n=8-10 in each group, both individual and summarized curves were shown, t-tests were performed between the TdLN resected and T-cell depleted groups, data were displayed as means #SEMs, t-test was performed between the TdLN(−) and TdLN(−) T-cell depleted groups, *p<0.05, p<0.01, *p<0.001, **p<0.0001). FIG. 14B shows that systemic depletion of T cells, but not TdLN resection, led to a shorter survival time of mice due to secondary tumor development (n=8-10 in each group, log-rank test between indicated groups, p<0.01). FIG. 14C shows the response to anti-4-1BB and anti-PD-1 treatment, which was tested in localized secondary tumors with or without TdLNs. Anti-4-1BB and anti-PD-1 treatments suppressed secondary tumor growth in both TdLN intact and resected mice (n=5 in each group, data were displayed as means±SEMs). See also FIGS. 19, 20, 22, and Table 2.

FIG. 15A shows that more activated ($CD62L^-$) CD4+ T cells were observed in TdLNs than NdLNs on 7 days post tumor cells inoculation. However, at the late stage of tumor development, the proportion of activated $CD4^+$ T cells was similar in TdLNs and NdLNs. The proportion of activated CD8+ T cells were close in TdLNs and NdLNs during tumor development (n=4 in each group, t-tests were performed, data were displayed as means±SEMs, n.s.: no significance, p<0.01). FIG. 15B shows that CD80 expression level on antigen presentation cells (APCs) was higher in TdLNs than NdLNs on 7 days post tumor cells inoculation (n=4 in each group, t-tests were performed, data were displayed as means±SEMs, n.s.: no significance, *p<0.001, MFI: mean fluorescent intensity). FIG. 15C shows that the proportion of $CD28^{high}$ T cells (both CD4+ and $CD8^+$) in TdLNs was decreased during tumor development (n=4 in each group, t-tests were performed, data were displayed as means±SEMs, n.s.: no significance, *p<0.001). FIG. 15**D shows that the concentration of IFNγ in TdLNs was higher at the early stage of tumor development than the late-stage (n=4 in each group, t-tests were performed, data were displayed as means±SEMs, n.s.: no significance, *p<0.05). FIG. 15E shows that at the established tumor model (volume 500-700 mm3), systemic distribution of tumor antigen (gp70) specific CD8+ T cells were detected in multiple lymphatic organs and the tumor microenvironment. The tumor microenvironment has the highest frequency of gp70 specific $CD8^+$ T cells than lymphatic organs (n=6 in each group, t-tests were performed between indicated groups, data were displayed as means±SEMs, n.s.: no significance, *p<0.05, p<0.01, *p<0.001). See also FIGS. 19-21 and Table 2.

FIG. 16A shows a schematic of the experimental design. Tumor (500 $mm^3$ to 700 $mm^3$ in volume) bearing mice were randomly assigned to 6 treatment groups: IgG (one dose/3 days), 5-FU monotherapy (one dose/12 days), anti-4-1BB monotherapy (one dose/3 days), anti-CD3 therapy (one dose/3 days) and anti-4-1BB therapy (one dose/3 days, two days after anti-CD3), 5-FU (one dose) and anti-4-1BB (1 dose/3 day, starting at 9 days post 5-FU) sequential therapy, and 5-FU (one dose/12 days) and anti-4-1BB (1 dose/3 day, started at the same day of 5-FU) concurrent therapy. The treatment was continued until the endpoint of follow-up. FIG. 16B shows the CT26 tumor response to different treatments. The 5-FU and anti-4-1BB sequential treatment significantly prolonged survival time of the tumor-bearing mice (n=4 in each group for the tumor growth curve, data were displayed as means±SEMs, n=7 in each group for the mouse survival curve, log-rank test between all survival curves, **p<0.0001). FIG. 16C shows the results of the same experiments of panel B repeated in the MC38 tumor model (n=4 in each group for the tumor growth curve, data were displayed as means±SEMs, n=7 in each group for the mouse survival curve, log-rank test between all survival curves, p<0.0001). See also FIGS. 23 and 24**.

FIG. 17A shows a schematic of the experimental design. The primary tumor and TdLNs were resected when tumors are at around 500 $mm^3$ in volume. Secondary tumors were induced and treated by different strategies at 300-350 $mm^3$ in volume. Some mice rejected the secondary tumors and were not included in the therapeutic study (anti-4-1BB or anti-PD-1). FIG. 17B shows that the 5-FU and anti-4-1BB sequential treatment was more efficient than the 5-FU and anti-4-1BB concurrent treatment in controlling secondary tumors in CT26 and MC38 models (n=7 in each group, data were displayed as means±SEMs, t test was performed between the sequential and concurrent treatment groups, *p<0.05). FIG. 17C shows that the 5-FU and anti-PD-1 sequential treatment was more efficient in controlling secondary tumors than the 5-FU and anti-PD-1 concurrent treatment in the CT26 model (n=7 in each group, data were displayed as means±SEMs, t test was performed between the sequential and concurrent treatment groups, *p<0.05). See also FIG. 23.

FIG. 18A shows ViSNE plots showing single cell level expression of PD-L1, Ki-67, CD80, and CD86 in the tumor tissue. PD-L1, Ki-67, CD80, and CD86 expression were quantified in whole tumor tissue. The 5-FU and anti-4-1BB sequential treatment significantly upregulated CD86 and CD80 expression in tumor tissues (n=3 in each group, data were displayed as means±SEMs, t-test was performed between the indicated groups, n.s.: no significance, *p<0.05, *p<0.001, MSI: mean signal intensity). FIG. 18B-18**I show the tumor-infiltrating T cells frequency, CD8/Treg ratio, Ki-67$^+$ CD8$^+$ T cells frequency, expression of PD-1 on CD8$^+$ T cells, myeloid-derived suppressive cells (MDSCs) frequency, macrophages frequency, NK cells frequency, and CD103+ dendritic cells (DCs) frequency were measured in tumors treated by different strategies (n=3 in each group, data were displayed as means±SEMs, t-test was performed between the indicated groups, n.s.: no significance, *p<0.05, p<0.01, MSI: mean signal intensity). See also FIGS. 25-27**.

FIG. 19A shows a schematic of the experimental design. Evan blue dye or Alexa Fluor® 488 dye was injected into the tumor in the right hinge flank to trace TdLNs. FIG. 19B shows stained lymph nodes. 10 min post Evan blue dye injection in the right hinge flank tumor, the right inguinal (RI) and right axillary (RA) lymph nodes (LNs) were stained. The deeper color was seen at 30 min and 60 min post-injection. Representative data from three independent experiments are shown. FIG. 19C shows a quantification of the stain. Flow cytometry was used for detecting the Alexa Fluor® 488 dye distribution in lymphatic organs (drainage from the right hinge flank tumor injection site). The RI LN and RA LN showed the highest FITC signal and were identified as the major TdLNs. The other LNs were identified as the non-draining lymph nodes (NdLNs) (n=3 in each group, data displayed as means±SEMs, RI: right inguinal, LI: left inguinal, RP: right popliteal, LP: left popliteal, RB: right brachial, LB: left brachial, RA: right axillary, LA: left axillary, M: mesenteric).

FIGS. 20A-20J show the weight of spleen and major superficial LNs (both TdLNs and NdLNs), which were measured at different time points of tumor development. During tumor development, a significant splenomegaly was observed. An obvious lymphadenopathy was observed in the TdLNs rather than in the NdLNs during tumor development (n=4 in each group, t-test was performed between indicated groups, data were displayed as means±SEMs, *p<0.05, p<0.01, *p<0.001, statistical analyses without significance were not shown). FIG. 20K shows an evaluation of the histology of TdLNs and NdLNs at the late-stage of tumor development. The TdLNs were larger than NdLNs and naïve LNs (taken from tumor-free mice). No metastasis was observed in TdLNs. Representative data from three independent experiments are shown (scale bars: 250 μm in 40× images and 50 μm in 200× images).

FIG. 21A shows a representative gating process of CD8+ gp70 (tumor) antigen-specific T cells in peripheral lymphatic organs. FIG. 21B shows a representative gating process of CD8+ gp70 (tumor) antigen-specific T cells in tumor tissues. The negative tetramer and lymphatic organs from naïve mice were used as controls for gating.

FIG. 22A shows that the frequency of lymphatic endothelia cells was higher in CT26 secondary tumors (mimicking recurrent tumors) with TdLNs than secondary tumors without TdLNs (n=8 in each group, t-test). The total tumor-infiltrating T cell frequency, PD-1 high expression T cells frequency, CD103+ dendritic cells (DCs) frequency, myeloid-derived suppressive cells (MDSCs) frequency, and PD-L1 expression were similar in two groups (n=8 in each group, t-test was performed, data displayed as means±SEMs, n.s.: no significance, *p<0.05). FIG. 22B shows the results of the experiments when they were repeated in the MC38 tumor model. The frequency of lymphatic endothelial cells and CD103+ DCs were higher in secondary tumors with TdLNs than in secondary tumors without TdLNs (n=4 in each group, t-test was performed, data displayed as means #SEMs, n.s.: no significance, *p<0.05).

FIG. 23A shows that 5-FU treatment on naïve mice depleted T cells in lymphatic organs, blood circulation, and bone marrow. The T cell population recovered around 9 days after 5-FU treatment (n=3 in each group, data were displayed as means±SEMs). FIG. 23B shows the results of a single-dose of anti-CD3 treatment on naïve mice depleted T cells for around 3 days (n=3 in each group, data were displayed as means±SEMs). FIGS. 23C-23D show that a combination of anti-4-1BB with 5-FU didn't rescue the T cell depletion induced by 5-FU treatment (n=3 in each group, t-test was performed, data were displayed as means±SEMs, n.s.: no significance).

FIGS. 24A-24B show mouse body weight, which was measured on day 12, 24, and 32 during treatment. On day 32, the mice treated with the 5-FU and anti-4-1BB sequential treatment have higher body weight than the mice treated with the 5-FU and anti-4-1BB concurrent treatment (n=7 in each group, t-test was performed between indicated groups at the last time point, individual value was shown, **p<0.0001). FIGS. 24C-24D show the results of a diarrhea assessment, which was performed at the endpoint of mice follow-up to evaluate the side effects on mouse intestine. The 5-FU and anti-4-1BB concurrent treatment, but not the sequential treatment, caused severe diarrhea (n=7 in each group, t-test was performed between indicated groups, data were displayed as means±SEMs, **p<0.0001).

FIG. 25A shows ViSNE plots of the major tumor-infiltrating immune cell populations. FIG. 25B shows manual gating of the major tumor-infiltrating immune cells. The alive cell population was first identified and the immune cells (CD45+) were then gated. The gating of T-cell populations (CD45+CD3+CD8+ for CD8+ T cells, CD45+CD3+CD4+CD25+Foxp3+ for Tregs), NK cells (CD45+CD3-CD11b-CD11c-CD49b+), macrophages (CD45+CD3−CD11b+F4/80+), myeloid-derived suppressive cells (MDSCs, CD45+CD3−CD11b+Gr−1+), and CD103+ DCs (CD45+CD3−CD11b−CD11c+I−A/I−E+

CD103+) are shown. The same markers were used throughout the study to identify the immune cells.

Figures 26A, 26B, 26C, 26D, 26E, 26F, 26G, 26H, 26I:
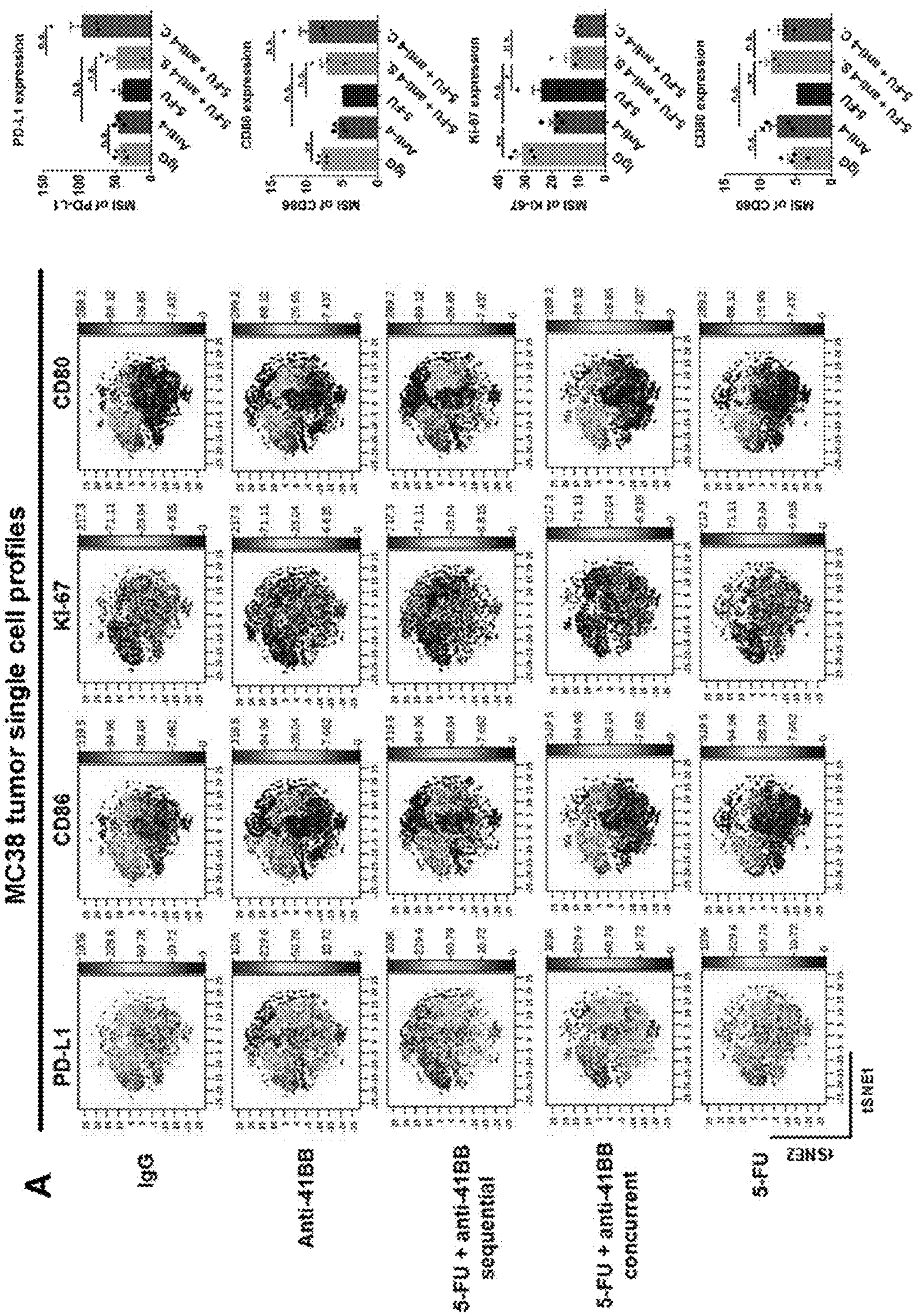
Figures 26A, 26B, 26C, 26D, 26E, 26F, 26G, 26H, 26I:
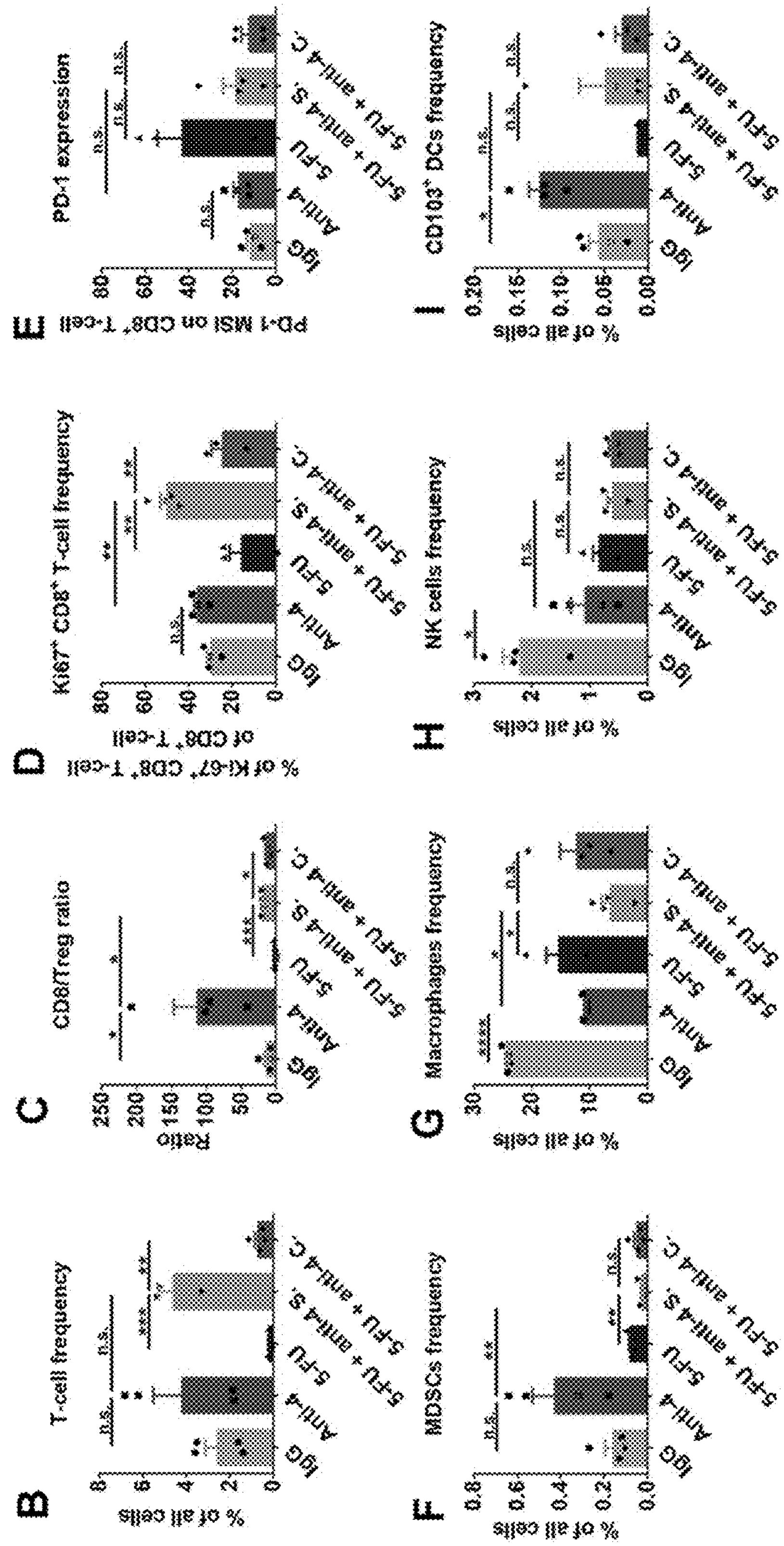

FIGS. 26A-26I show the tumor immunological response to 5-FU and anti-4-1BB treatments in MC38 tumors. Related to FIG. 18. FIG. 26A shows ViSNE plots of single cell level expression of PD-L1, Ki-67, CD80, and CD86 in the MC38 tumor tissue. The 5-FU and anti-4-1BB sequential treatment significantly upregulated CD80 while decreased Ki-67 expression in tumor tissues (n=4 in each group, t-test was performed between indicated groups, data were displayed as means±SEMs, MSI: mean signal intensity, n.s.: no significance, *p<0.05, p<0.01). FIGS. 26B-26**I show that the tumor-infiltrating T cell frequency, CD8/Treg ratio, and Ki-67+CD8+ T cell frequency were higher in the sequential treatment than the concurrent treatment group. The myeloid-derived suppressive cells (MDSCs) were depleted in 5-FU treated groups. The 5-FU and anti-4-1BB sequential treatment were compared with the anti-4-1BB monotherapy, 5-FU monotherapy, and 5-FU and anti-4-1BB concurrent treatment (n=4 in each group, t-test was performed between indicated groups, data were displayed as means±SEMs, MSI: mean signal intensity, n.s.: no significance, *p<0.05, p<0.01, *p<0.001, ****p<0.0001).

Figures 27A, 27B, 27C, 27D, 27E, 27F, 27G, 27H:
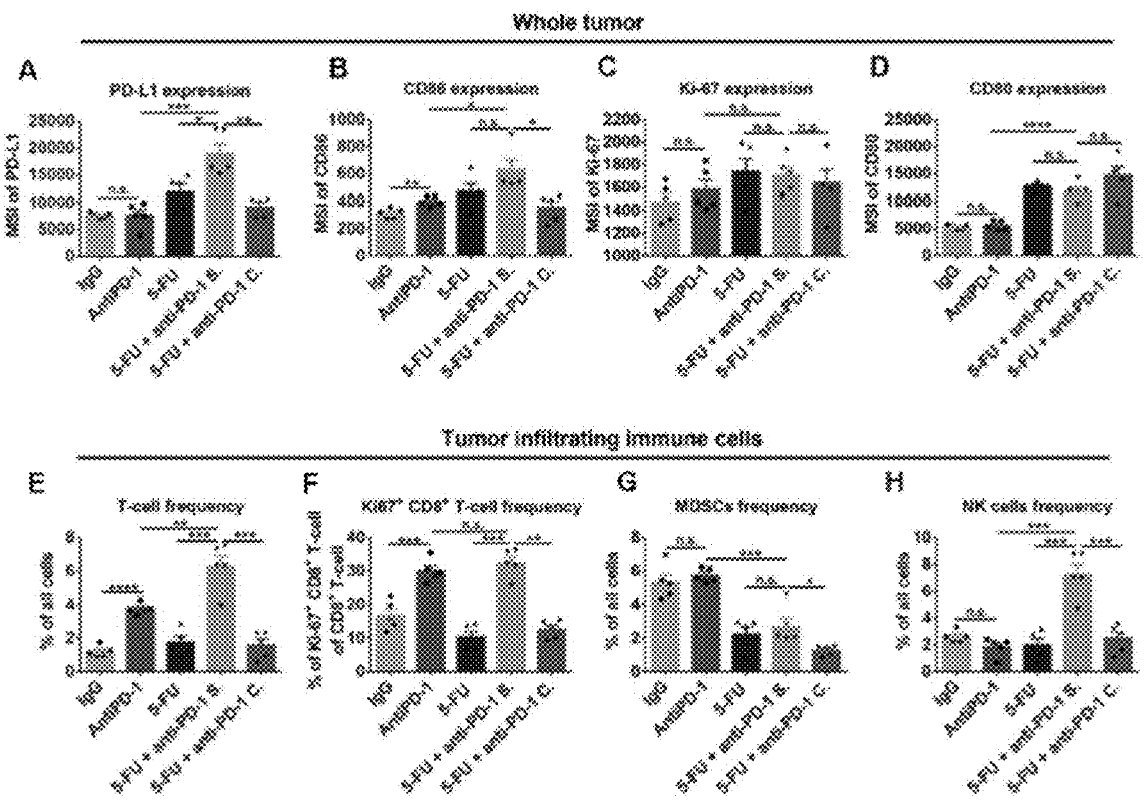

FIGS. 27A-27H show the tumor immunological response to 5-FU and anti-PD-1 treatments in CT26 tumors. Related to FIG. 18. FIGS. 27A-27D show that the 5-FU and anti-PD-1 sequential treatment significantly increased PD-L1, CD80, and CD86 expression in CT26 tumors (n=5 in each group, t-test was performed between indicated groups, data were displayed as means±SEMs, MSI: mean signal intensity, n.s.: no significance, *p<0.05, p<0.01, *p<0.001, **p<0.0001). FIGS. 27E-27**H show that the 5-FU and anti-PD-1 sequential treatment significantly increased tumor-infiltrating T cell frequency, Ki-67+CD8+ T cell frequency, and NK cell frequency in tumor tissues, compared with the concurrent treatment. The myeloid-derived suppressive cells (MDSCs) were depleted in 5-FU treated groups (n=5 in each group, t-test was performed between indicated groups, data were displayed as means±SEMs, MSI: mean signal intensity, n.s.: no significance, *p<0.05, p<0.01, *p<0.001, ****p<0.0001).

Figure 28:
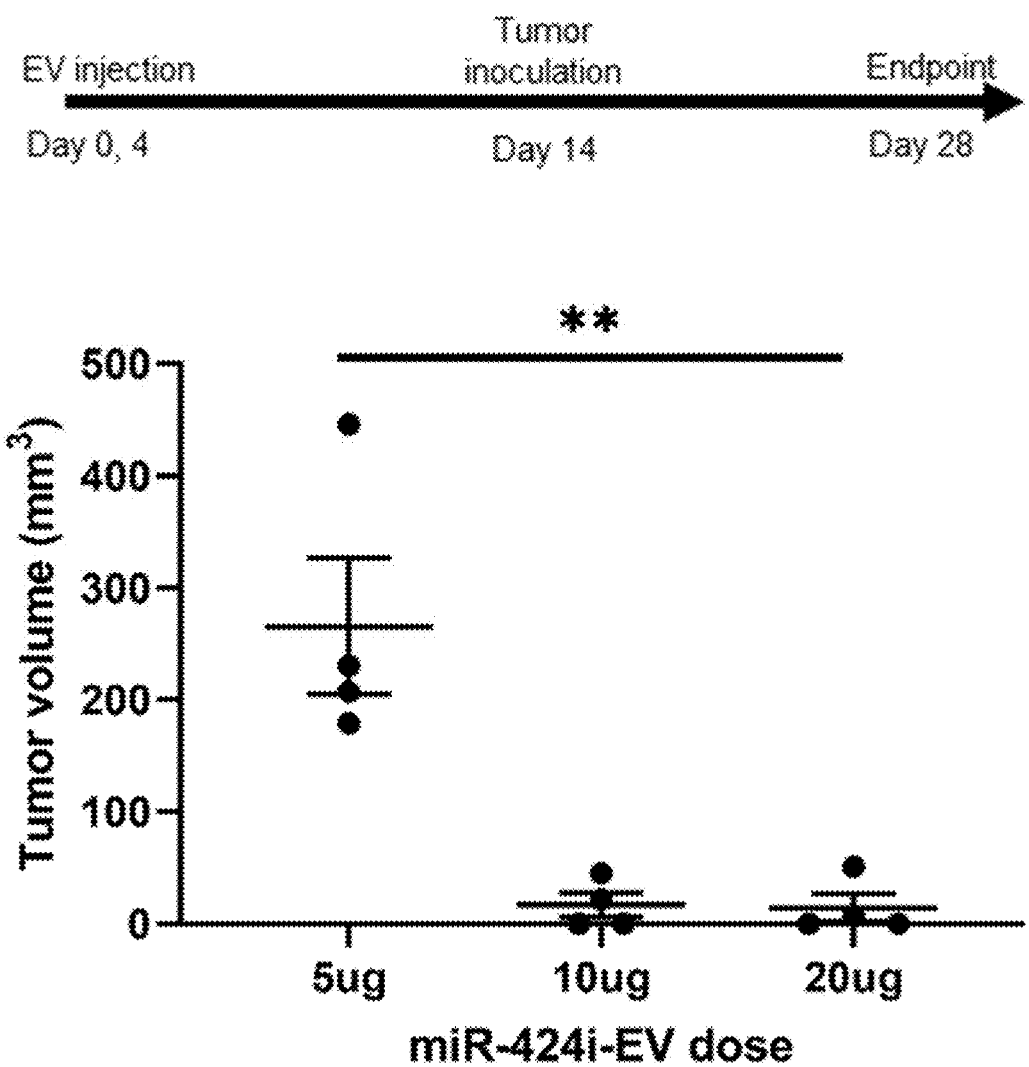

FIG. 28 shows the primary tumor volumes measured in the experiment described in Example 3. Different doses of EVs (5 ug, 10 ug, and 20 ug) were used to pre-condition the naïve mice. On day 14, CT26 tumor cells were inoculated subcutaneously to induce the primary tumor. Tumor volume from each group was measured at day 28. (**p<0.01)

Figure 29:
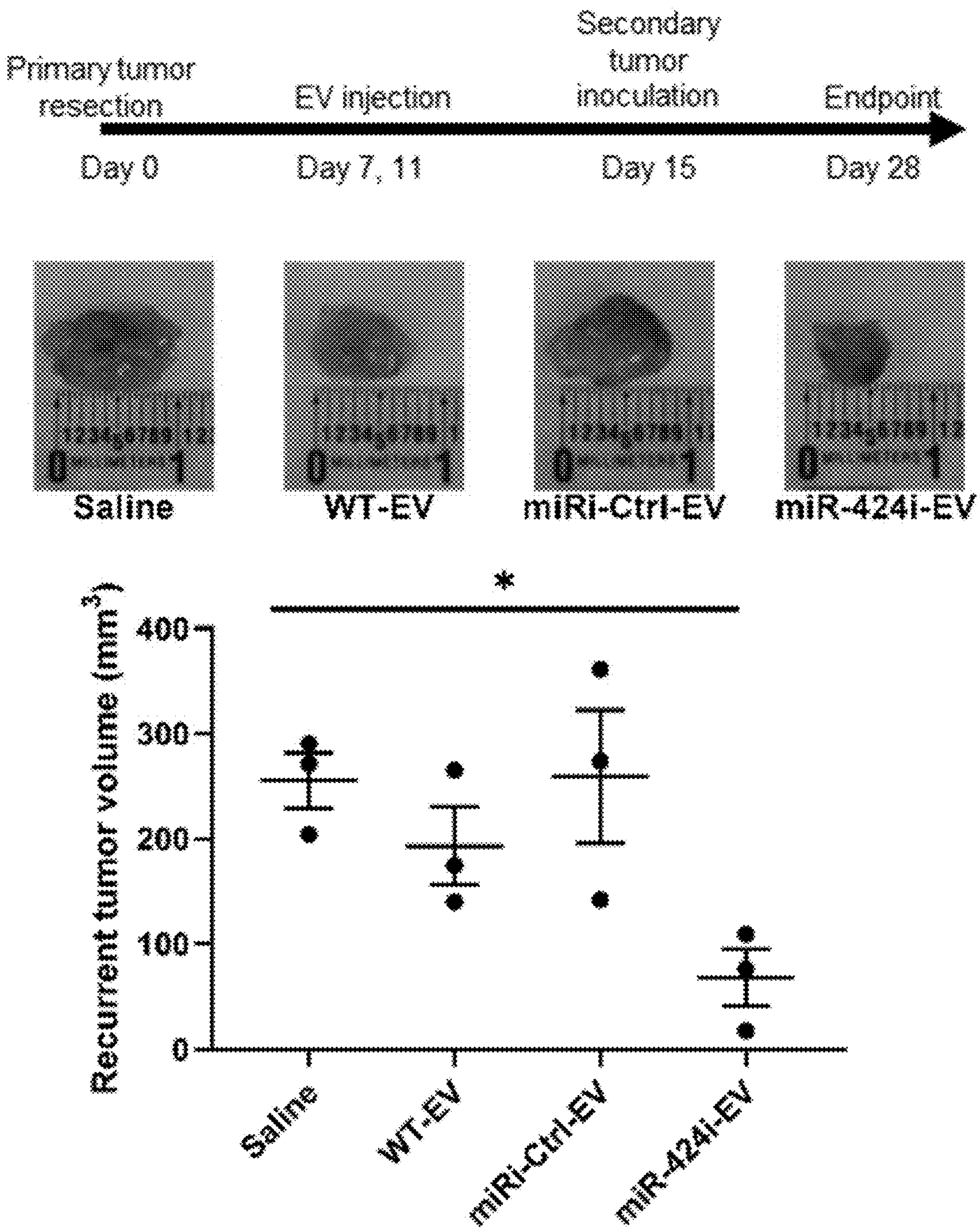

FIG. 29 shows the secondary tumor volumes measured in the experiment described in Example 3. The primary subcutaneous CT26 tumor was surgically resected at 300-500 $mm^3$ on day 0. On day 7 and day 11, the mice were treated intravenously with saline and EVs (10 ug) from different CT26 cell lines. The secondary tumor was inoculated on day 15 and the mice were followed-up for 2 weeks. The tumor volume at endpoint was plotted. (*p<0.05)

DETAILED DESCRIPTION OF THE INVENTION

In the specification and in the claims, the terms "including" and "comprising" are open-ended terms and should be interpreted to mean "including, but not limited to . . . " These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present invention is based on the finding that T-cells and antigen presentation cells (APCs) isolated from nonimmunogenic, microsatellite stable (MSS) CRC have lower levels of CD28 and CD80 expression compared to normal tissues. Downregulation of CD28 in T-cells and CD80 in APCs significantly reduced T-cell priming. The inventors found that CRC tumors have elevated levels of miR-424 compared to the normal colon tissues, and that miR-424 suppressed the expression of CD28 and CD80 in immune cells. Further, the inventors demonstrated that miR-424 is present in EVs secreted by CRC cells, which are taken up by T cells and APCs, therefore, affecting their immune-stimulating function in the tumor microenvironment.

Blocking expression of miR-424 or genetically deleting miR-424 in tumor cells significantly improved anti-tumor immunity in mouse models. Thus, the present invention provides tumor-derived extracellular vesicles (EVs) that lack or have reduced expression of an immune suppressive factor (e.g., miR-424) that can be used to improve cancer treatment efficacy and increase the anti-tumor immune response in a subject. For instance, the modified tumor-derived EVs can be used in combination with a checkpoint inhibitor therapy to improve cancer treatment outcomes.

The inventors further found that depleting the functional miR-424 in tumor cell-derived EVs unleashes the immune-stimulating function of tumor-derived EVs. Tumor cell-derived EVs without functional miR-424 were used to pre-condition the tumor naïve mice. Mice that were pre-conditioned with the modified EVs generated tumor specific T-cells in the peripheral lymphatic organs, which prevented tumor formation induced by the same tumor cells used to generate the EVs. The protection efficacy was positively correlated with the vaccination dose. Mice pre-conditioned with PBS and control wild-type EVs did not protect the mice against tumors. In orthotopic models of CRC that mimic the advanced stage of human tumors, we tested a combination of modified EVs with the current immune checkpoint inhibitor-based therapies (PD1/CTLA4). Mice treated with the combination showed better survival than those treated with the current immune checkpoint inhibitor-based therapies alone.

These results provide preclinical evidence that treating CRC tumors with modified EVs (lacking immunosuppressive miRNAs), with or without immune checkpoint inhibitor-based therapies, significantly improves antitumor immune response and reduces tumor burden. These results provide insights on how cancer cells modulate and suppress the immune response, provide novel targets, and form the basis for a new anti-cancer therapeutic strategies.

EVs and Compositions

In one embodiment, the invention provides modified tumor-derived extracellular vesicles (EVs) isolated from a tumor cell having reduced or lacking expression of an immune suppressive factor.

The term "immune suppressive factor" or "immune suppressor factor" refers to a factor or molecule that is involved in the tumor-microenvironment and associated with immune escape and dysfunctional activity of tumor-specific immune response (e.g., dysregulation and inhibition of the immune regulatory cells, e.g., $CD8^{+}T$ cells) that results in a an inhibition of a robust immune response to the tumor. The present invention reduces or eliminates the expression of such immune suppressive factor within tumor-derived EVs, releasing the immune suppression and resulting in an increased immune response against tumor cells and tumor antigens. Suitable immune suppressive factors may vary depending on the type of tumor cells to be targeted and treated. In some embodiments, the immune suppressive factor is specific to a certain tumor cell targeted, and may, in some embodiments, specific to a patient's tumor cell.

In a preferred embodiment, the immune suppressive factor is miR-424. Information regarding miR-424 (or microRNA 424) can be found at Genbank Gene ID 494336 (ncbi.nlm.nih.gov/gene/494336) miRBase accession MI0001446 (www.mirbase.org). In some embodiments, the mature human miR-424 sequence (i.e., hsa-miR-424-5p; SEQ ID NO:1) is utilized. In other embodiment, the mature mouse ortholog miR-322 (i.e., mmu-miR-322-5p; SEQ ID NO:2) is utilized.

Other suitable immune suppressive factors that may be used with the present invention include, but are not limited to, factors that target PD-L1, TGF-beta, and other miRNAs that have immunosuppressive functions, such as hsa-miR-3187-3p, hsa-miR-498, hsa-miR-15a, hsa-miR-16-1, hsa-miR-195, hsa-miR-135b, hsa-miR-2355, hsa-miR-146a, hsa-miR-98, hsa-miR-188, hsa-miR-200c, hsa-miR-200a, hsa-miR-183, hsa-miR-182, and hsa-miR-21 (SEQ ID NOs: 3-17, respectively). Immunosuppressive factors can be identified by methods known in the art, for example, CRISPR screening, preclinical animal models, and in vitro T-cell function assays, among others. Some of the noted immune suppressive factors described in this paragraph are involved with multiple cancer cell types and can be used to treat any of the cancers in which they play a role.

In one embodiment, the invention provides modified tumor-derived extracellular vesicles (EVs) isolated from a tumor cell and having reduced or eliminated miR-424 expression. Tumor-derived EVs having reduced or eliminated mir-424 can be produced from tumor cells that have been modified to have reduced or eliminated miR-424 expression. Methods of reducing or eliminating miR-4124 expression in the tumor cells (and, therefore, reducing or eliminating miR-4124 expression in the resultant EVs) are discussed in more detail below.

microRNAs (miRNAs) are short (~22 nt) non-coding RNAs that are involved in post-transcriptional regulation of gene expression in multicellular organisms, affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a miRNA-induced silencing complex (RISC), which recognizes target mRNAs through imperfect base pairing with the miRNA and most commonly results in translational inhibition or destabilization of the target mRNA.

Methods for inhibiting, reducing or eliminating expression of an immune suppressive factor described herein are known in the art and contemplated herein. Suitable methods include, for example, siRNA, transducing cells with an anti-immune suppressive factor oligonucleotides, genetically modifying the tumor cells (e.g., via CRISPR/Cas9 genome editing, etc.), among others.

Methods of blocking miR-424 expression within a tumor cell, thus, reducing or eliminating its expression within the tumor cell, are known in the art. For example, siRNA may be used to block expression of miR-424. Other methods include, but are not limited to, for example, transducing tumor cells with anti-miR-424 expression lentiviral vectors or transfecting tumor cells with anti-miR-424 oligos (e.g., an oligo with a sequence that is complementary to mature miR-424, e.g., SEQ ID NO:18). Another method of eliminating miR-424 expression is to genetically modify the tumor cell to reduce or eliminate miR-424 expression, for example, by knocking out the nucleic acid sequence encoding for the miR-424. Suitable methods for genetically modifying the tumor cell include, but are not limited to, for example, using CRISPR/Cas9-mediated genome editing to knock out the miR-424 gene from the genome, or transducing tumor cells with an expression vector that encodes an anti-miR-424 oligo or a gene able to knock out the expression of miR-424. The inventors have shown that blocking miR-424 expression or genetically deleting the miR-424 in tumor cells significantly improved the anti-tumor immunity in mouse models. Thus, in one embodiment, the present invention provides tumor-derived extracellular vesicles (EVs) that have reduced or deleted miR424 expression that can be used to improve cancer treatment and increase the anti-tumor immune response in a subject.

The term "vector" refers to a nucleic acid molecule capable of propagating and expressing another nucleic acid to which it is linked. The term includes the vector as a self-replicating nucleic acid structure as well as the vector incorporated into the genome of a host cell in which it has been introduced. Certain vectors are capable of directing the expression of nucleic acids to which they are operatively linked. Vectors include plasmid vectors and viral vectors, which are known in the art. Vectors also include expression vectors, such as viral vectors (e.g., replication defective retroviruses (including lentiviruses), adenoviruses and adeno-associated viruses (rAAV)), which serve equivalent functions. In some embodiments, the vector encodes an anti-miR precursor sequence that is able to regulate gene expression by binding to and inhibiting a specific mature miRNA, for example, miR-424 (e.g., SEQ ID NO: 1).

In some embodiments, the modified tumor-derived extracellular vesicles (EVs) of the present invention are exosomes or microvesicles. Exosomes, as used herein, are a form of extracellular vesicles that originate from intraluminal vesicles within the multivesicular bodies (MVB) that are released from cells upon fusion of a multivesicular body with the plasma membrane in a cell. Microvesicles (MVs) originate from outward blebbing of the plasma membrane. Both exosomes and MVs carry cargo, including proteins, mRNA, miRNA and lipids.

The modified tumor-derived EVs of the present invention are able to express one or more tumor antigens, which should be specific to the tumor cell, tumor organoid, or tumor cell line they are isolated from. For example, tumor-derived EVs from colorectal cancer cells will preferably express one or more antigens specific for colorectal cancer, EVs from breast cancer cell line will express one or more antigens specific for breast cancer, and so on. In some embodiments, the modified tumor-derived EVs may be modified to comprise one or more exogenous antigens.

The modified tumor-derived EVs of the present invention may be about 30 to about 300 nanometers in diameter. Alternatively, the modified tumor-derived EVs may be about 50 to about 280 nanometers in diameter.

The modified tumor-derived EVs may be produced from a tumor cell that has been modified to inhibit or reduce the expression of one or more immune suppressive factors, for example, miR-424, as discussed above. Suitable tumor cells include, but are not limited to, for example, primary tumor cells, cultured tumor cells, and patient derived tumor organoids.

Suitable tumor cell lines for use in the invention are known in the art and include, but are not limited to, colorectal cancer cell lines, such as HCT116 (ATCC® CCL-247™), HT29 (ATCC® HTB-38™), DLD-1 (ATCCR CCL-221™), SW680, SW480 (ATCC® CCL-228™), HCT8 (ATCC® CCL244™), WiDr (ATCCR CCL-218™), and Caco-2 (ATCC® HTB-37™); pancreatic cancer lines, such as PANC-1 (ATCC® CRL-1469™), MIA-PaCa-2 (ATCC® CRL-1420™), and BXPC-3 (ATCC® CRL-1687™); and stomach cancer cell lines, such as SNU-5 (ATCC® CRL-5973™), AGS (ATCC® CRL-1739™), and SNU-1 (ATCC® CRL-5971™).

One skilled in the art may establish tumor organoids from a patient's tumor, and isolate EVs from the culture media of the organoids. Primary tumor cells can also be used to establish cell lines that produce EVs. In some embodiments, the primary cells can be for a specific tumor cell isolated from a specific patient to be used for a personalized medicine treatment, i.e. the specific patient's cells are used to make a cell line and tumor-derived EVs that are used to treat the patient from which the tumor cells came. Tumor organoids are three-dimensional self-organizing structures that are grown in vitro but were made from in vivo derived tumor tissue or from healthy tissue that has been genetically modified (for example, via CRISPR/Cas9 gene editing). Methods of deriving and growing organoids for a particular cancer are known in the art. For example, human organoids are discussed in the review by Tuveson and Clevers "Cancer modeling meets human organoid technology: Science vol. 364, Issue 6444 Jun. 7, 2019, the contents of which are incorporated by reference in its entirety.

Suitably, in some embodiments, the tumor cell is a cancer cell selected from the group consisting of colorectal cancer, breast cancer, endometrial cancer, prostate cancer, lung cancer, melanoma, and pancreatic cancer. In a preferred embodiment, the tumor cell is a colorectal cancer cell. In some embodiments, the cell is autologous to the subject to which it will be used to treat, and in some alternative embodiments, the cell will be allogeneic.

In some embodiments, the modified EVs described herein and used for the treatment of cancer. In certain embodiments, the modified EVs are used for the treatment of a secondary tumor.

The present invention also provides a composition (i.e., a pharmaceutical composition) comprising one or more of the modified tumor-derived EVs described herein and a pharmaceutically acceptable carrier. The pharmaceutically acceptable carrier may be selected based upon the desired route of administration. Suitable pharmaceutically acceptable carriers will allow for maintenance of the structural stability of the tumor-derived EVs within the composition for a period of time before administration to the subject.

In some embodiments, the composition is a vaccine composition. The vaccine composition may be used in the methods described herein to increase an immune response against one or more tumor antigens, and in turn, against tumor cells. In some embodiments, the vaccine composition is used to target secondary or metastatic tumors, for example, after resection or removal of a first primary tumor. The vaccine composition may inhibit or reduce the formation of secondary tumors within a subject. The vaccine composition suitably comprises one or more modified EVs described herein. In some embodiments, the vaccine further comprises one or more adjuvants that can increase the immune response to the tumor antigens present in the modified EVs. The vaccine compositions may be used for any of the methods described herein, including for the inhibition and treatment of secondary tumors (e.g., metastatic tumors).

In some embodiments, the compositions of the present invention further comprise one or more checkpoint inhibitor, for example, one or more PD-1 inhibitors, or PDL1 inhibitors, or CLTA-4 inhibitor, among others.

In some embodiments, the compositions of the present invention comprise two or more tumor-derived EVs that are derived from two or more different tumor cells. In some embodiments, the two or more tumor-derived EVs may be derived from the same type of tumor (e.g., breast cancer, colorectal cancer) but are from different individual tumors (e.g., tumors that have different mutations (e.g., KRAS mutant, EGFR mutant), are from two different sources (e.g., two different subjects), etc.). In some embodiments, the two- or more tumor-derived EVs are from two or more tumor cells from the same type of cancer, e.g., breast cancer, colorectal cancer.

In some embodiments, the composition or vaccine composition further comprises a pharmaceutically acceptable carrier. The term "pharmaceutically acceptable" means approved by a regulatory agency of the Federal or a state government or listed in the U.S. Pharmaceutically acceptable" carriers are known in the art and include, but are not limited to, suitable diluents, preservatives, solubilizers, emulsifiers, liposomes, nanoparticles and adjuvants. For example, pharmaceutically acceptable carriers may comprise 0.01 to 0.1 M and preferably 0.05M phosphate buffer or 0.9% saline. Additionally, such pharmaceutically acceptable carriers may be aqueous or non-aqueous solutions, suspensions, and emulsions. Examples of nonaqueous solutions include propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media.

The term "carrier" refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration. The vaccine compositions may include a pharmaceutical carrier, excipient, or diluent, which are nontoxic to the cell or subject being exposed thereto at the dosages and concentrations employed. Often a pharmaceutical diluent is in an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN brand surfactant, polyethylene glycol (PEG), and PLURONICS™ surfactant.

The vaccine compositions described herein may include adjuvants to increase immunogenicity of the composition. The adjuvant may be any of the currently FDA-licensed adjuvants for vaccine usage including, without limitation, aluminum salt (alum) and the squalene oil-in-water emulsion systems MF59 (Wadman 2005 (Novartis)) and AS03 (GlaxoSmithKline).

In some embodiments, these vaccine compositions comprise one or more of a mineral adjuvant, gel-based adjuvant, tensoactive agent, bacterial product, oil emulsion, particulated adjuvant, fusion protein, and lipopeptide. Mineral salt adjuvants include aluminum adjuvants, salts of calcium (e.g. calcium phosphate), iron and zirconium. Gel-based adjuvants include aluminum gel-based adjuvants and acemannan. Tensoactive agents include Quil A, saponin derived from an aqueous extract from the bark of *Quillaja saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gramnegative bacteria (e.g., from *Mycobacterium* spp., *Corynebacterium parvum, C. granulosum, Bordetella pertussis* and *Neisseria meningitidis*), N-acetyl muramyl-L-alanyl-D-isoglutamine (MDP), different compounds derived from MDP (e.g., threonyl-MDP), lipopolysaccharides (LPS) (e.g., from the cell wall of Gram-negative bacteria), trehalose dimycolate 5 (TDM), cholera toxin or other bacterial toxins, and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide) microspheres have been extensively studied and find use herein. Notably, several of the delivery particles noted above may also act as adjuvants. In some embodiments, the vaccine compositions further include cytokines (e.g., IFN-γ, granulocyte-macrophage colony stimulating factor (GM-CSF) IL-2, or IL-12) or immunostimulatory molecules such as FasL, CD40 ligand or a toll-like receptor agonist, or carbohydrate adjuvants (e.g. inulin-derived adjuvants, such as, gamma inulin, algammulin, and polysaccharides based on glucose and mannose, such as glucans, dextrans, lentinans, glucomannans and galactomannans).

In some embodiments, adjuvant are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol. In some embodiments, the additional adjuvants are described in Jennings et al. Adjuvants and Delivery Systems for Viral Vaccines-Mechanisms and Potential. In: Brown F, Haaheim L R, (eds). Modulation of the Immune Response to Vaccine Antigens. Dev. Biol. Stand, Vol. 92. Basel: Karger 1998; 19-28 and/or Sayers et al. J Biomed Biotechnol. 2012; 2012:831486, and/or Petrovsky and Aguilar, Immunology and Cell Biology (2004) 82, 488-496. In some embodiments, the adjuvant is an aluminum gel or salt, such as aluminum hydroxide, aluminum phosphate, and potassium aluminum sulfate, AS04 (which is composed of aluminum salt and MPL), and ALHYDROGEL. In some embodiments, the aluminum gel or salt is a formulation or mixture with any of the additional adjuvants described herein.

Pharmaceutical compositions and vaccine compositions of the present disclosure may be sterilized by conventional, well known sterilization techniques. The compositions may contain pharmaceutically acceptable additional substances as required to approximate physiological conditions such as a pH adjusting and buffering agents, toxicity adjusting agents, such as, sodium acetate, sodium chloride, potassium chloride, calcium chloride, sodium lactate, and the like. For example, the compositions may include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc., or onto liposomes, microemulsions, micelles, milamellar or multilamellar vesicles, erythrocyte ghosts, or spheroplasts. Such compositions may influence the physical state, solubility, stability, rate of in vivo release, and rate of in vivo clearance. Controlled or sustained release compositions include formulations in lipophilic depots (e.g., fatty acids, waxes, oils).

Methods of Producing EVs and Methods of Use

The present invention provides tumor-derived EVs lacking one or more immune suppressive factors, e.g., miR-424, and methods of making and using the same.

In one embodiment, a method of producing a tumor-derived extracellular vesicle (EV) substantially lacking expression of one or more immune suppressive factor (e.g., miR-424) expression comprises: (a) providing a modified tumor cell that is lacking in expression of the immune suppressive factor (e.g., miR-424) and can produce EVs; and (b) isolating EVs produced by the tumor cell, wherein the EVs substantially lack expression of the immune suppressive factor.

In some preferred embodiments, the immune suppressive factor is miR-424 and the EVs substantially lack expression of miR-424.

Modified tumor cells that lack or have reduced expression of the immune suppressive factor are discussed above and include, but are not limited to, a tumor cell line that has been genetically modified to eliminate the immune suppressive factor, for example, to eliminate miR-424 expression. Multiple methods can be used to reduce or eliminate miR-424 expression from tumor cells. For example, one can transduce tumor cells with an anti-miR-424 expression vector, for example, a lentiviral vector. In another example, the tumor cells may be transfected with one or more anti-miR-424 oligonucleotides. In another nonlimiting example, CRISPR/Cas9 gene editing can be used to knockout the miR-424 gene from tumor cell genome. However, any suitable method may be used to remove functional miR-424.

Methods of isolating the EVs from the tumor cell include, but are not limited to, collecting or harvesting media in which the tumor cells were cultured, for example, collecting media after miR-424 modified tumor cells have been cultured for at least 24 hours, alternatively for at least 48 hours, or alternatively for at least 72 hours. In some embodiments, media is collected every 24 hours and pooled. The media or pooled media can then be ultracentrifuged to separate the EVs from the media. In some embodiments, the media is xenogen-free medium. In some embodiments, the medium is serum-free medium. Methods of isolating EVs are known in the art. General methods to isolate EVs include, for example, ultra-centrifugation (e.g., using the ExoQuick ULTRA (System Biosciences, LLC) kit), size exclusion chromatography, and membrane ultrafiltration. One exemplary protocol includes, for example, isolating EVs from cell culture supernatants. In this method, cells are cultured in media supplemented with 10% exosome depleted FBS (Gibco). Supernatants are then collected from 24 h cell cultures and EVs are purified by a standard differential centrifugation protocol. In brief, culture supernatants are centrifuged at 300 g for 10 min to remove cells. The supernatant is then centrifuged at 3,000 g for 10 min to remove dead cells. Debris is pelleted after centrifugation at 10,000 g for 30 min. Supernatants are then centrifuged at 100,000 g for 70 min at 4° C. (Beckman Coulter). The pelleted EVs are suspended in PBS and collected by ultracentrifugation at 100,000 g for 70 min at 4° C. again to minimize protein. In this Examples, a similar method was used to isolate human CRC organoid-derived EVs. Thus, in some embodiments, the tumor cell is a cultured tumor cell or a tumor organoid.

The present invention further provides methods of treating a subject having cancer. In one embodiment, the method of treating cancer in a subject comprises administering an effective amount of tumor-derived EVs to a subject in need thereof. In this method, the EVs substantially lack expression of an immune suppressive factor or miR-424 and the EVs comprise one or more tumor or cancer antigens. The one or more tumor or cancer antigens are derived from the tumor cell from which the EVs lacking miR-424 are produced. For example, if the EVs are produced from colorectal cancer cells, the EVs will comprise one or more antigens specific for colorectal cancer, etc. As discussed above, the EVs for use in the methods described herein are lacking in one or more immune suppressive factor, e.g., miR-424. Not to be bound by any theory, but it is believed that reducing miR-424 expression will reduce the immunoinhibitory effects of miR-424 on the EVs, allowing for a robust and increased immune response to be mounted against the tumor antigens.

In some embodiments, the method further comprises administering one or more additional anti-cancer therapies. In one preferred embodiment, the one or more additional cancer therapies include a checkpoint inhibitor.

In some embodiments, one or more additional cancer therapies include a chemotherapy. In Example 2, the inventors demonstrate that treatment with an immune checkpoint blockade therapy is more effective when it is administered subsequently to a chemotherapy as compared to when it is administered simultaneously with a chemotherapy, and that intact systemic immunity is required for this improvement (see FIGS. 16-18). Thus, in some embodiments in which a chemotherapy is utilized, the tumor-derived EVs are administered after the subject's T-cell population have substantially recovered following the chemotherapy (e.g., at least a week after chemotherapy is administered).

The term "anti-cancer therapy," "cancer therapy," and "anti-cancer drug" are used interchangeably to refer to therapeutics that are used for the treatment of cancer, including chemotherapy, immunotherapy, among others. Suitable anti-cancer therapies are known in the art and depend on the type of cancer being treated. Suitable anti-cancer therapies are described herein and include, for example kinase inhibitors, including BRAF inhibitors or MEK inhibitors, checkpoint inhibitors, and chemotherapeutics.

The terms "cancer," "tumor" or "malignancy" are used throughout this description interchangeably and refer to the diseases of abnormal cell growth. In some embodiments, the cancer treated by the methods is solid tumor. In some embodiments, the cancer treated by the methods is a colorectal cancer, an ovarian cancer, a cervical cancer, a breast cancer, an endometrial cancer, a colon cancer, a prostate cancer, a lung cancer, a melanoma, or a pancreatic cancer. In preferred embodiments, the cancer is a colorectal cancer.

As used herein, the terms "administering" and "administration" refer to any method of providing a pharmaceutical preparation or the EVs to a subject. Such methods are well known to those skilled in the art and include, but are not limited to, oral administration, transdermal administration, administration by inhalation, nasal administration, topical administration, intravaginal administration, intraaural administration, intracerebral administration, rectal administration, sublingual administration, buccal administration, and parenteral administration, including injectable such as intravenous administration, intra-arterial administration, intramuscular administration, intradermal administration, intrathecal administration, intratumoral administration and subcutaneous administration. In preferred embodiments, the composition or EVs are administered intratumorally or intravenously. Administration can be continuous or intermittent. In various aspects, a preparation can be administered therapeutically; that is, administered to treat an existing cancer or metastasis.

An effective amount will depend on the cancer and the route of administration. In some embodiments, the subject will be treated with one or more times with the EVs or compositions comprising the EVs, for example, with once a week, twice a week, one every other week, or other intermittent or regular schedules decided by a skilled artisan.

By "treating" we mean the management and care of a subject for the purpose of combating the disease, condition, or disorder. Treating includes the administration of a compound or composition described herein to reduce, prevent, ameliorate and/or improve the onset of the symptoms or complications, alleviating the symptoms or complications, or reducing or eliminating the disease, condition, or disorder. For example, treating cancer in a subject includes the reducing, repressing, delaying or preventing of cancer growth, reduction of tumor volume, and/or preventing, repressing, delaying or reducing metastasis of the tumor. Treating cancer in a subject also includes the reduction of the number of tumor cells within the subject. The term "treatment" can be characterized by at least one of the following: (a) the reducing, slowing or inhibiting of the growth of cancer and cancer cells, including slowing or inhibiting the growth of metastatic cancer cells; (b) preventing the further growth of tumors; (c) reducing or preventing the metastasis of cancer cells within a subject; and (d) reducing or ameliorating at least one symptom of cancer. In some embodiments, the optimum effective amount can be readily determined by one skilled in the art using routine experimentation.

By "modulation" of, e.g., a symptom, level or biological activity of a molecule, replication of a pathogen, cellular response, cellular activity or the like means that the cellular level or activity is detectably increased or decreased. Such increases or decreases may be observed in treated subjects as compared to subjects not treated with the EVs or compositions, where the untreated subjects have, or are susceptible to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self-assessment, by a clinician's assessment, or by conducting an appropriate assay or measurement, including, e.g., quality of life assessments or suitable assays for the level or activity of molecules, cells, or cell migration within a subject. Modulation may be transient, prolonged or permanent or it may be variable at relevant times during or after the EVs or composition is administered to a subject or is used in an assay or other method described herein or a cited reference, e.g., within about 1 hour of the administration or use of the EVs or compositions to about 3, 6, 9 months or more after a subject(s) has received the EVs or compositions.

As used herein "subject" or "patient" refers to mammals and non-mammals. "Mammals" means any member of the class Mammalia including, but not limited to, humans, non-human primates (e.g., chimpanzees, other apes, and monkey species), farm animals (e.g., cattle, horses, sheep, goats, and swine), domestic animals (e.g., rabbits, dogs, and cats) laboratory animals including rodents (e.g., rats, mice, and guinea pigs). Examples of non-mammals include, but are not limited to, birds, and the like. The term "subject" does not denote a particular age or sex. In one specific embodiment, a subject is a mammal, preferably a human.

The term "effective amount" or "therapeutically effective amount" refers to an amount sufficient to effect beneficial or desirable biological and/or clinical results. That result can be reducing, inhibiting, or preventing the growth of cancer cells, including drug-resistant or therapy resistant cancer cells, reducing, inhibiting, or preventing metastasis of the cancer cells or invasiveness of the cancer cells or metastasis, or reducing, alleviating, inhibiting or preventing at least one symptom of the cancer or metastasis thereof, or any other desired alteration of a biological system. An "effective treatment" refers to treatment producing a beneficial effect, e.g., amelioration of at least one symptom of a cancer. A beneficial effect can take the form of an improvement over baseline, i.e., an improvement over a measurement or observation made prior to initiation of therapy according to the method. A beneficial effect can also take the form of reducing, inhibiting or preventing further growth of cancer cells, reducing, inhibiting or preventing metastasis of the cancer cells or invasiveness of the cancer cells or metastasis or reducing, alleviating, inhibiting or preventing at least one symptoms of the cancer or metastasis thereof. Such effective treatment may, e.g., reduce patient pain, reduce the size or number of cancer cells, may reduce or prevent metastasis of a cancer cell, or may slow cancer or metastatic cell growth.

In some embodiments, the method further comprises treating the subject with one or more suitable checkpoint inhibitors, for example, one or more PD-1 inhibitors, or PDL1 inhibitors, or CLTA-4 inhibitor, among others.

Compositions comprising one or more tumor-derived EVs and one or more checkpoint inhibitors (e.g., PD-1 inhibitor, PD-L1 inhibitor, or CTLA-4 inhibitor, among others) are also contemplated. This combinational therapeutic can be used for the treatment of cancer.

In some embodiments, the tumor-derived EVs, compositions and methods described herein can be used for personalized medicinal purposes. For example, the tumor-derived EVs may be derived from the tumor cells from the subject, or may be derived from tumor organoids generated from the subject's tumor cells.

In other embodiments, the tumor-derived EVs and compositions will be used for treatment of an unrelated subject, and may be used to make an off-the shelf product that could be used for treatment of cancers.

Suitable cancers that can be treated by the methods described herein include, for example, solid tumors, and may include, but are not limited to, colorectal cancer, ovarian cancer, cervical cancer, breast cancer, endometrial cancer, colon cancer, prostate cancer, lung cancer, melanoma, or pancreatic cancer rectal cancer, liver cancer, sarcomas (multiple types), brain tumors kidney cancer, bladder cancer, head and neck neuroblastoma thyroid cancer, among others.

In another embodiment, the present disclosure provides a method of stimulating an anti-tumor response in a subject having cancer, the method comprising administering tumor-derived EVs described herein or the composition described herein to a subject having cancer in an amount effective to elicit an anti-tumor response in the subject. The above methods of treating cancer and stimulating an anti-tumor response may further include treating the subject with a checkpoint inhibitor. In some embodiments, administering tumor-derived, miR-424-depleted EVs (a) increases CD28 expression on T cells, (b) increases T cell proliferation in the subject or (c) both (a) and (b) in a subject having cancer. In some embodiments, the anti-tumor response comprises the reduction or inhibition of secondary tumor growth.

In some embodiments, the present invention provides a method of stimulating an anti-tumor immune response, the method comprising administering tumor-derived EVs described herein or the composition described herein to a subject having cancer in an amount effective to stimulate an anti-tumor response in the subject.

Not to be bound by any theory, but the methods of the present invention provide a method of inducing T cell activation against cancer antigens presented on the EVs. Thus, in some embodiments, the anti-tumor immune response comprises an improved immune-mediated anti-tumor response to an anti-cancer therapy.

An "anti-tumor response" or an "improved immune-mediated anti-tumor response" means an increase in the ability of one or more immune cells to recognize tumor cells. In some instances, the improved immune-mediated anti-tumor response results in an increased ability of one or more immune cells to target/recognize and kill cancer cells (e.g. CD8+ T cells). An improved immune-mediated anti-tumor response may be seen as a reduction in the number of cancer cells, inhibiting, retarding or slowing the growth of cancer cells, inhibiting, retarding or slowing the metastasis of cancer cells, increased infiltration of cytotoxic T cells into the tumor, or decreased inhibition of immune population within the tumor microenvironment.

In some embodiments, the anti-tumor response is a cell-mediated immune response. The terms "cell-mediated immune response" or "cell-mediated immunity" refer to an immune response mediated by immune cells and does not involve antibodies (humoral immune response). Specifically, cell-mediated immune response includes antigen-specific cytotoxic T-lymphocytes (CD8+ T cells) or activation of phagocytes. Phagocytes include white blood cells such as neutrophils, monocytes, macrophages, mast cells, and dendritic cells. In a preferred embodiment, the cell-mediated immune response is a cytotoxic T cell response or CD8+ T cell response.

In another embodiment, the present invention provides a method of sensitizing a tumor cell in a subject to immune checkpoint inhibitors, the method comprising administering tumor-derived EVs described herein, or the composition described herein, to a subject having cancer and subsequently administering one or more checkpoint inhibitors to the subject.

Suitable checkpoint inhibitors include, but are not limited to, for example, an inhibitor of PD-1, an inhibitor of PD-L1, an inhibitor of CTLA-4, or combinations thereof.

Suitable PD-1 inhibitors for use in the methods described herein are known in the art and include, but are not limited to, for example, anti-PD-1 antibodies. Preferred anti-PD-1 antibodies are PD-1 monoclonal antibodies. Suitable anti-PD-1 antibodies include, but are not limited to, for example, pembrolizumab (Keytruda, Merck), nivolumab (Opdivo, BMS-936559, Bristol-Myers Squibb), cemiplimab (Libtayo, Regeneron Pharmaceuticals Inc., Sanofi), Avelumab (Bavencio, Pfizer), durvalumab (Imfinzi, AstraZeneca), atezolizumab (Tecentriq, Genentech), pidilizumab (Cure Tech), AMP-224, (GlaxoSmithKline), AMP-514 (GlaxoSmithKline), PDR001 (Novartis), among others. Other suitable anti-PD-1 inhibitors include, but are not limited to, for example; MEDI0680 (MedImmune/AstraZeneca); MEDI4736 (Medlmmune/AstraZeneca); MPDL3280A (Genentech/Roche), MSB0010718C (EMD Serono), among others.

Suitable PD-L1 inhibitors are known in the art and include, but are not limited to, for example, atezolizumab (Roche), avelumab (Merck Serono and Pfizer), durvalumab (AstraZeneca), BMS-936559 (Bristol-Myers Squibb), CK-301 (Checkpoint Therapeutics), among others.

Suitable CTLA-4 inhibitors include, but are not limited to, for example, tremelimumab (anti-CTLA-4 antibody, AstraZeneca), ipilimumab (Bristol-Myers Squibb), AGEN1884 (Agenus Inc.), among others.

In some embodiments, the checkpoint inhibitor is an antibody. For example, in some embodiments, the checkpoint inhibitor is the monoclonal antibody pembrolizumab (marketed under the trade name "Keytruda®"). Pembrolizumab is a human programmed death receptor-1 (PD-1)-blocking antibody indicated for the treatment of patients with unresectable or metastatic melanoma. Accordingly, in some embodiments the same dose and schedule is used as has been used for the approved melanoma indication. For example, in some embodiments pembrolizumab is administered at 2 mg/kg (rounded to the nearest 50 mg) as an intravenous infusion over 30 minutes every 3 weeks (up to four maximum doses).

In other embodiments, the checkpoint inhibitor is the monoclonal antibody nivolumab (marketed under the trade name "Opdivo®"). Nivolumab is a human IgG4 anti-PD-1 monoclonal antibody that acts as an immunomodulator by blocking ligand activation of the programmed cell death 1 (PD-1) receptor on activated T cells. In particular, nivolumab acts by blocking a negative regulator of T-cell activation and response, thus allowing the immune system to attack the tumor. That is, nivolumab blocks PD-L1 from binding to PD-1, allowing the T cell to function in tumor attack.

Administration of the EVs and checkpoint inhibitor may be performed simultaneously (e.g., at the same time) or sequentially. The term "simultaneous administration," as used herein, means that the agents (e.g., the EVs and checkpoint inhibitor) are administered with a time separation of no more than about 1 day (e.g., each component is administered within 24 hours, for example, within 2, 4, 6, 8. 10 or 12 hours, or, in other examples, within 60, 50, 40, 30, 20, or 10 minutes). When the agents are administered simultaneously, the agents may be contained in the same composition or in separate compositions (e.g., the EVs are contained in one composition and the checkpoint inhibitor is contained in another composition).

In some embodiments, the agents are administered sequentially or intermittently. The term "sequential administration" as used herein means that the agents or compositions are administered with a time separation of more than about 1 day. In one embodiment, the EVs or compositions comprising them are administered first followed by daily or weekly administration of the checkpoint inhibitor. Alternatively, the checkpoint inhibitor may be administered first, followed by the EVs. The time between the administration of the EVs and checkpoint inhibitor can be adjusted for maximum efficacy, and may be in the order of minutes, hours, days or weeks. In some embodiments, the agents are administered intermittently. The term "intermittent administration" as used herein refers to administration that does not occur daily, for example, administration of a checkpoint inhibitor that occurs weekly, biweekly, etc. In some embodiments, the EVs may be administered daily or continuously and the checkpoint inhibitors are administered intermittently.

In another embodiment, the present disclosure provides a method of preventing, reducing, or inhibiting tumor growth in a subject comprising administering an effective amount of a vaccine composition comprising tumor-derived EVs to a subject in need thereof in order to prevent, reduce, inhibit tumor cell growth. In this method, the EVs substantially lack expression of an immune suppressive factor or miR-424. In some preferred embodiments, the tumor is a secondary tumor.

Use as Vaccine Compositions

The inventors have surprisingly found that the modified EVs described herein, when used as a vaccine composition, are able to inhibit and reduce the growth of secondary tumors within a subject. This use of EVs for tumor vaccination may result in the ability to reduce the re-occurrence or spread of tumors to secondary sites within a subject, prolonging remission and overall life expectancy. The compositions and modified EVs of the present invention provides additional benefits of other methods of trying to regulate anti-tumor T-cell responses. For example, not to be bound by any theory, but the present modified EVs provide benefits of CAR T cells to tumors in that they can express multiple antigens at the same time, providing a more robust immune response over CAR T cells that can only express one or two specific tumor antigens. The diversity of the antigens allows for an increase in the capability of providing an increase anti-tumor response. Further, different tumor cell lines or primary tumors can be used to derive the modified EVs described herein, making the compositions and methods applicable to a wide range of cancers.

As used herein, the term "vaccine" refers to any composition that is capable of eliciting an immune response against one or more antigens in a subject. The vaccines of the present invention comprise modified tumor-derived EVs, which comprise one or more cancer antigens derived from the tumor cell from which the EVs were produced. For example, if the EVs are produced from colorectal cancer cells, the EVs will comprise one or more antigens specific for colorectal cancer, etc. Thus, the EVs of the present invention can be as vaccines that elicit a tumor-specific immune response.

The present invention provides method of use of the vaccine composition comprising one or more modified tumor-derived EVs described herein for the treatment of secondary tumors. In some examples, the vaccine composition is administered after the resectioning or removal of the primary tumor. Not to be bound by any theory, but the vaccine compositions provided herein are believed to be able to reduce or inhibit the growth of secondary tumors after the removal of the primary tumor, but increasing the anti-tumor immune response (e.g., increasing tumor-specific CD8+ T cells) in the subject administered the vaccine composition. Further, the vaccine composition may be administered in combination with one or more checkpoint inhibitors after removal or treatment of the primary tumor. In some embodiments, the primary tumor is removed. In other embodiments, the primary tumor is treated using chemotherapy. In some embodiments, the vaccine composition, alone or in combination with a checkpoint inhibitor, is administered after the chemotherapy. The timing after administration of the chemotherapy is an amount of time that is sufficient to allow for the recovery of some immune cell (e.g., T cell) function within the subject. Suitable times would be determined by one skilled in the art and include, for example, at least one week, at least two weeks, after administration of the chemotherapeutic agent.

In some embodiments, the tumor cell is an adenoma (e.g., benign tumor), which is inhibited from forming adenocarcinoma, a more aggressive form of cancer. In other embodiments, the tumor cell is a cancer cell as described herein.

In some embodiments, the tumor is a secondary tumor, and the vaccine is administered to the subject after a primary tumor was resected from the subject. The term "secondary tumor," "metastasis," or "metastatic tumor" refers to cancer cells that have spread to a secondary site, e.g., outside of the primary (i.e., original or first) tumor tissue. Secondary sites include, but are not limited to, the lymphatic system, skin, distant organs (e.g., liver, stomach, pancreas, brain, etc.) and the like and will differ depending on the site of the primary tumor.

In another embodiment, the present disclosure provides a method for preventing the growth of a secondary tumor in a subject following resection of a primary tumor, the method comprising administering an effective amount of a vaccine comprising tumor-derived EVs to the subject. In these methods, the tumor-derived EVs lack expression of an immune suppressive factor (e.g., miR-424). In some embodiments, the methods further comprise administering a checkpoint inhibitor to the subject in need thereof.

In another embodiment, the present disclosure provides a method for reducing or inhibiting metastasis of a cancer, the method comprising administering an effective amount of a vaccine comprising one or more tumor-derived EVs to the subject. In these methods, the tumor-derived EVs lack expression of an immune suppressive factor (e.g., miR-424). In some embodiments, the methods further comprise administering a checkpoint inhibitor to the subject in need thereof.

It should be apparent to those skilled in the art that many additional modifications besides those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: Modified Tumor Exosomes Prevent Tumor Formation by Stimulating Anti-Tumor Immunity This Example demonstrates that reduction of miR-424 in EVs from tumor cells improves the anti-tumor response in the mouse model. This Example further demonstrates that T-cells and antigen presentation cells (APCs) isolated from nonimmunogenic, microsatellite stable (MSS) CRC have lower levels of CD28 and CD80 compared with normal tissues. Downregulation of CD28 in T-cells and CD80 in APCs significantly reduced T-cell priming. The inventors found that CRC tumors have an elevated level of miR-424 compared to the normal colon tissues. MiR-424 showed suppressive effects of CD28 and CD80 expression in immune cells. Further, the inventors demonstrated that miR-424 is present in EVs secreted by CRC cells, which are taken up by T-cells and APCs, thereby affecting their immune-stimulating function in the tumor microenvironment.

Blocking or genetically deleting miR-424 in tumor cells significantly improved the anti-tumor immunity in mouse models. Thus, the present invention provides tumor-derived extracellular vesicles (EVs) that lack or have reduced miR-424 expression that can be used to improve cancer treatment and increase the anti-tumor immune response in a subject.

The inventors further found that depleting the functional miR-424 in tumor cell-derived EVs unleashes the immune-stimulating function of tumor-derived EVs. Tumor cell-derived EVs without functional miR-424 were used to pre-condition tumor naïve mice. Mice pre-conditioned with the modified EVs generated tumor specific T-cells in the peripheral lymphatic organs and prevented tumor formation that was induced with the same tumor cells that generated the EVs. The protection efficacy was positively correlated with the vaccination dose. In contrast, pre-conditioning with PBS or control wild-type EVs did not protect the mice against tumors. In orthotopic models of CRC that mimic the advanced stage of human tumors, we tested a combination of modified EVs with current immune checkpoint inhibitor-based therapies (PD1/CTLA4). Mice treated with the combination showed better survival than those treated with the current immune checkpoint inhibitor-based therapies alone.

These results provide preclinical evidence that treating CRC tumors with modified EVs (lacking immunosuppressive miRNAs) with or without immune checkpoint inhibitor-based therapies will significantly improve antitumor immune response and reduce tumor burden. These results provide insights on how cancer cells modulate and suppress the immune response, provide novel targets, and form the basis for a new anti-cancer therapeutic strategy.

Results:

Reduced Expression of Expression of CD28 and CD80/86 on Immune Cells in CRC Results in Tumor Resistance to Immune Checkpoint Blockades.

Figures 1A, 1B, 1C, 1D:
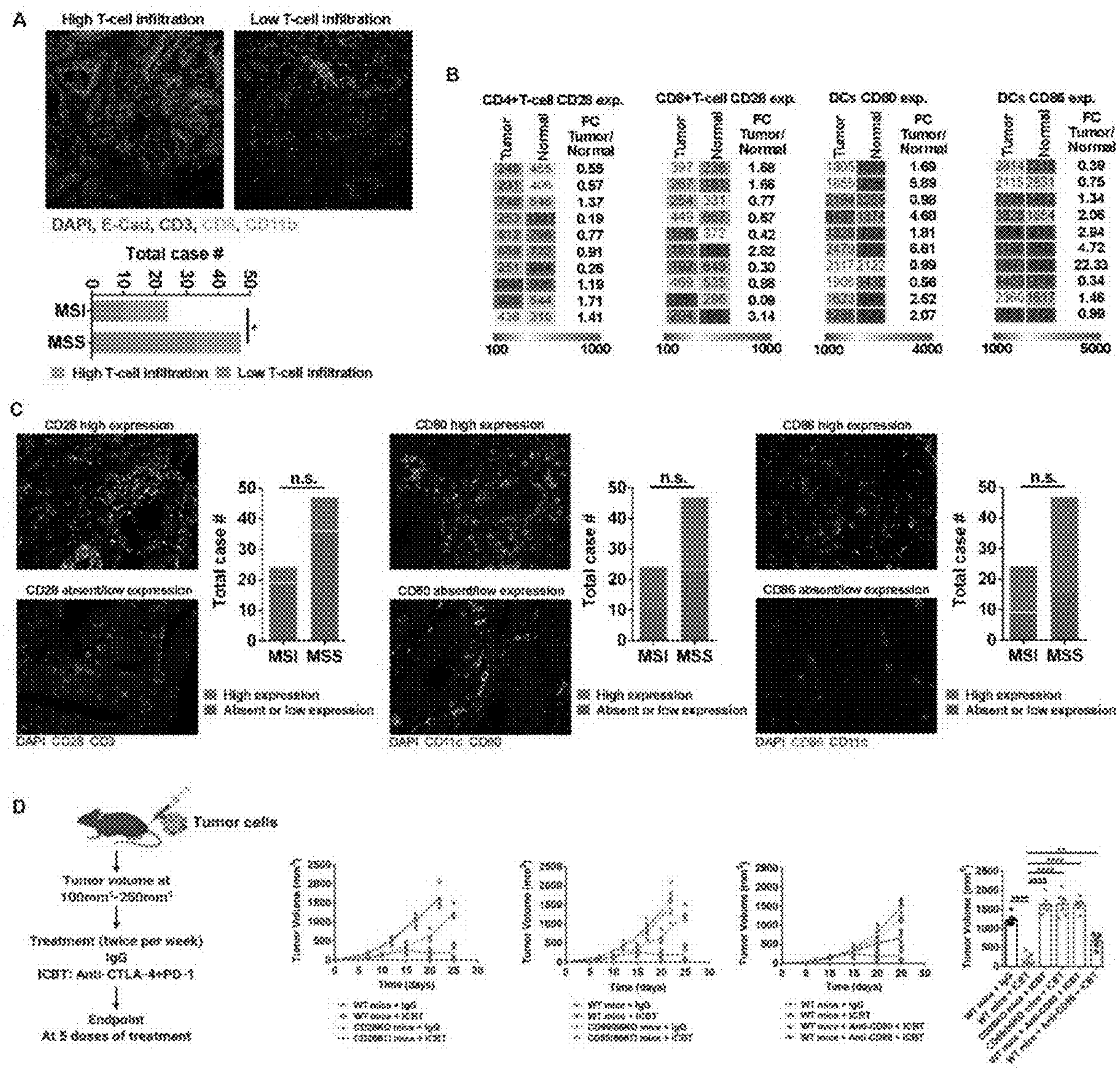
FIGS. 1A-1D.
Figure 2:
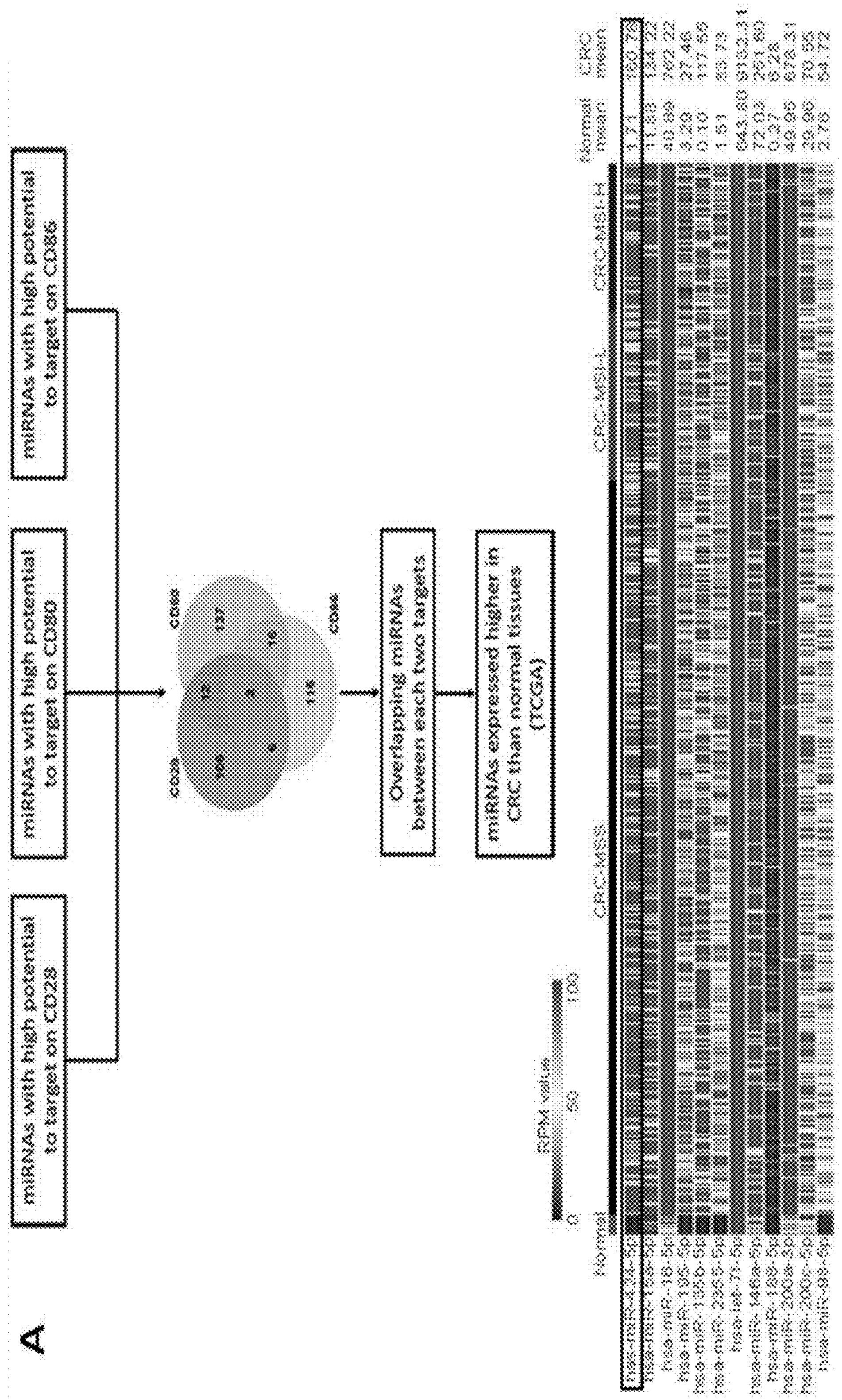
FIGS. 2A-2G.
Figures 2A, 2B, 2C, 2D, 2E, 2F, 2G:
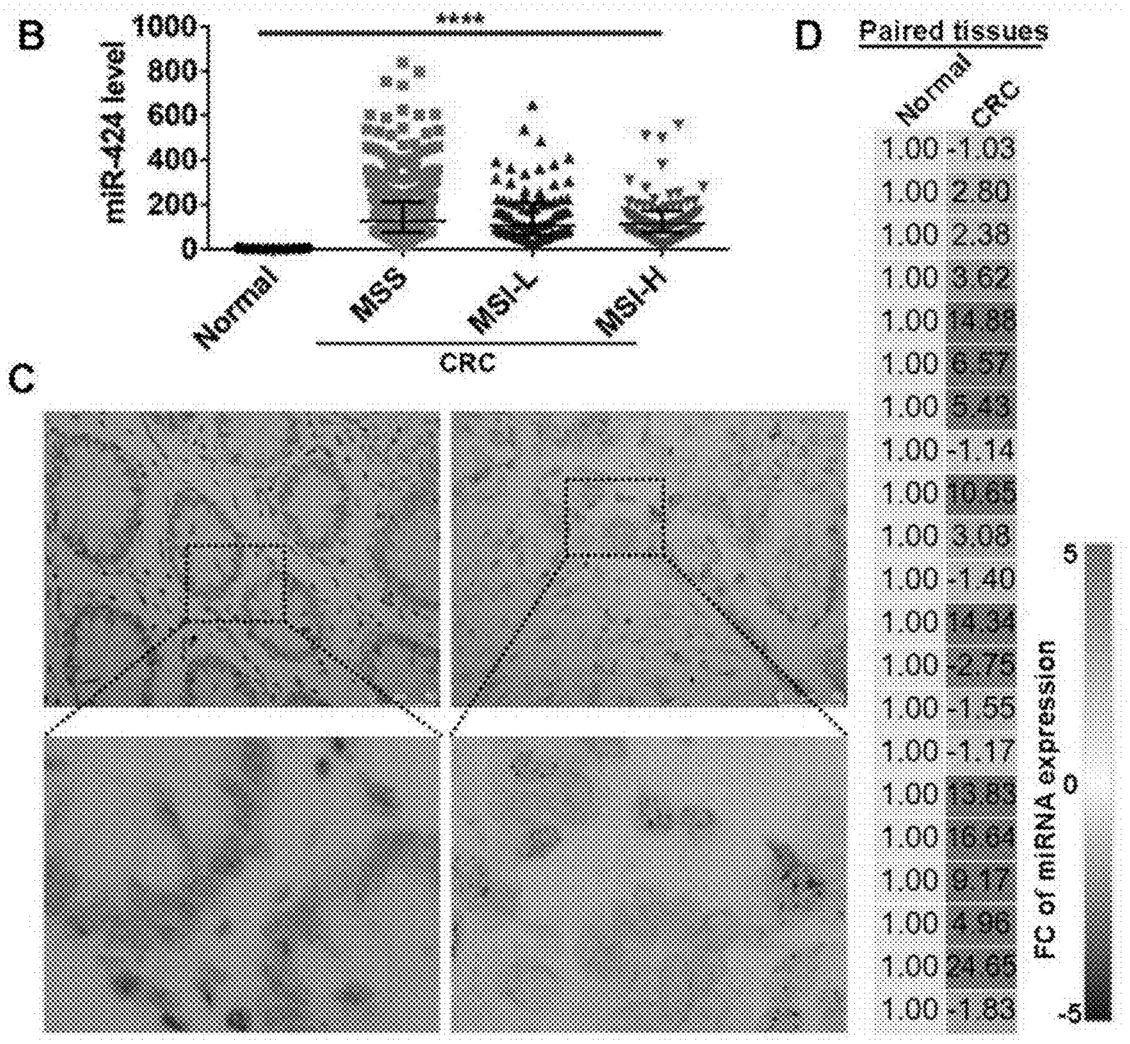
Figures 2A, 2B, 2C, 2D, 2E, 2F, 2G:
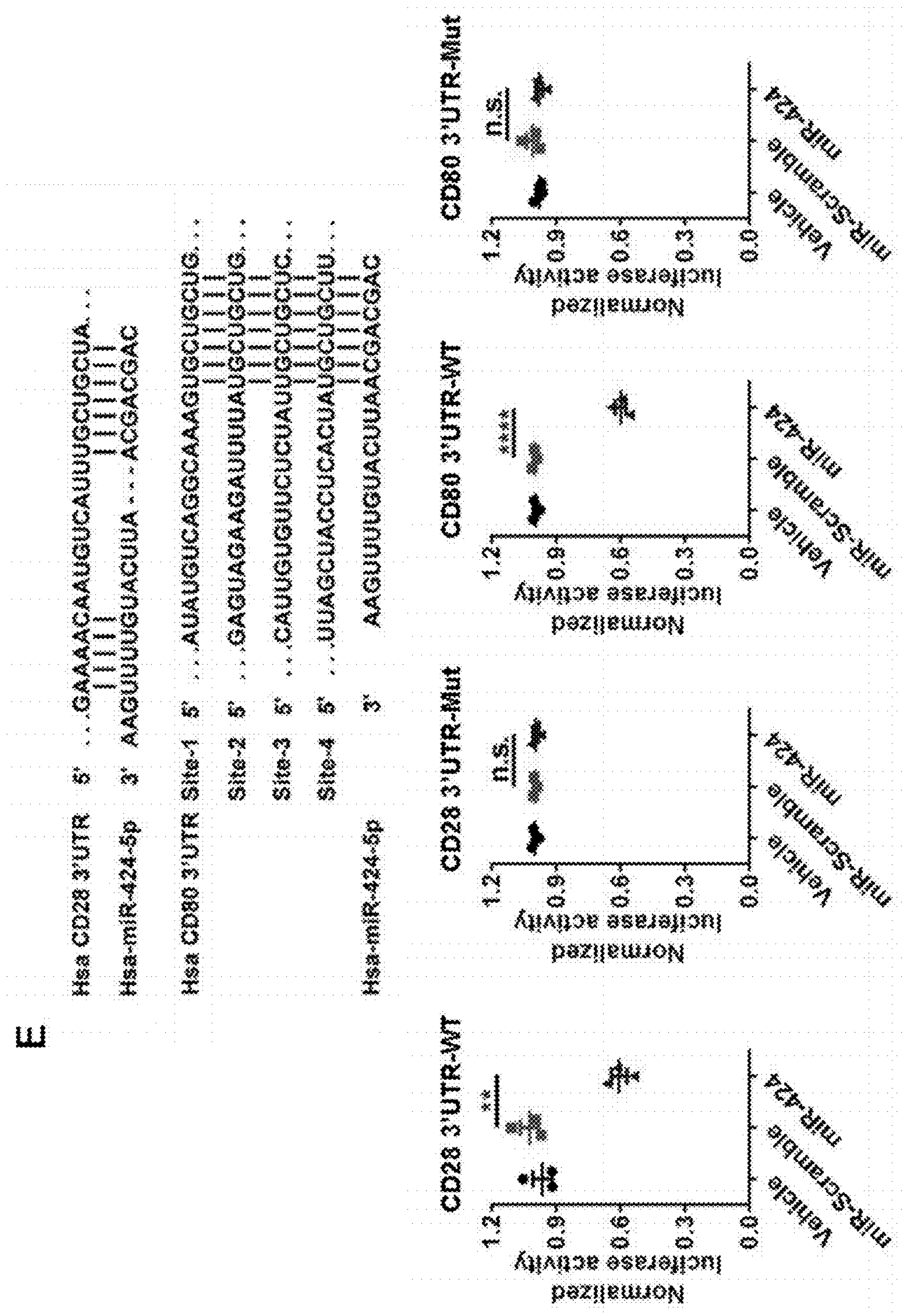
Figures 2A, 2B, 2C, 2D, 2E, 2F, 2G:
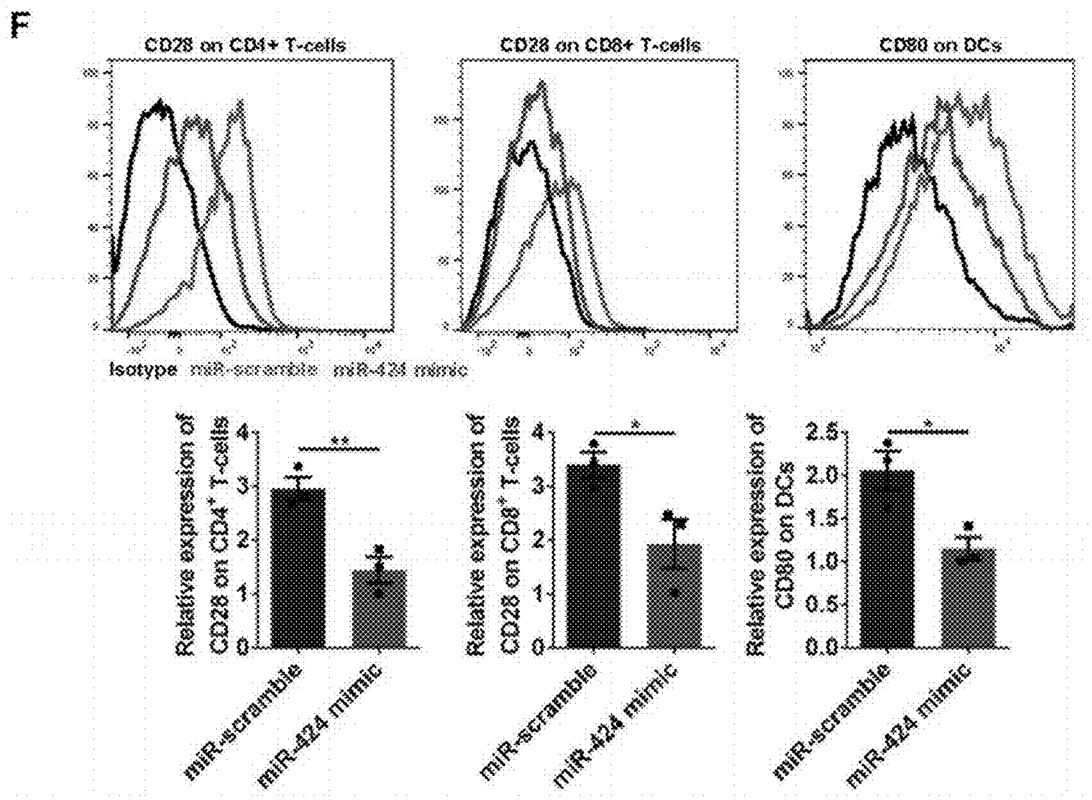
Figures 2A, 2B, 2C, 2D, 2E, 2F, 2G:
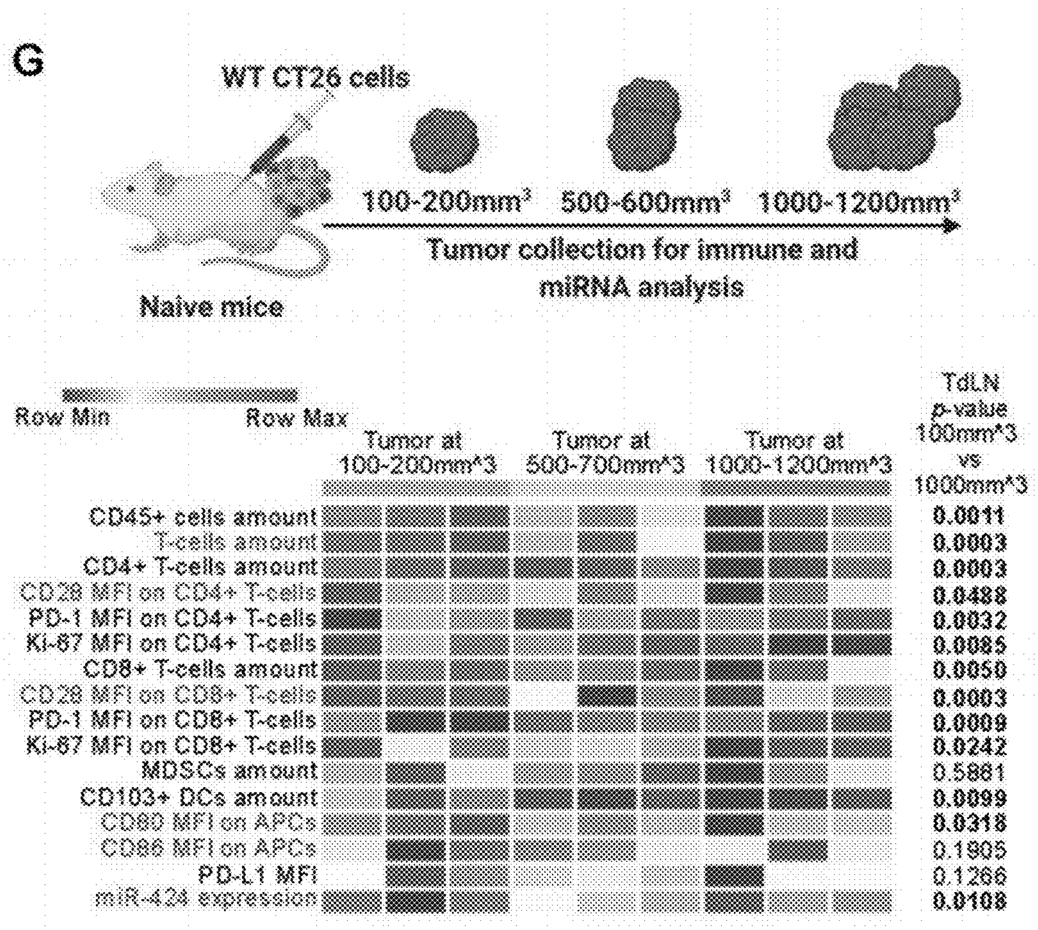

To determine whether the EVs secreted by human colorectal cancer (CRC) cells are taken up by T-cells and ACPs, we performed immunofluorescent staining of human CRC sections. T-cell infiltration was examined using CD3 staining. We found that the microsatellite stable (MSS) subtype CRC cases showed lower T-cell infiltration than the microsatellite instability (MSI) subtype CRC cases (FIG. 1A). Next, flow cytometry was performed on fresh human CRC colon tissues and paired normal colon tissues to detect the expression of CD28 on CD4+ and CD8+ T-cells and of CD80 and CD86 on DCs. Some CRC cases showed very low CD28, CD80, or CD86 expression levels (FIG. 1B), demonstrating that these markers are downregulated on immune cells in CRC. These results were confirmed by performing immunofluorescent staining on human CRC sections (FIG. 1C), which demonstrated that some CRC cases are characterized by high CD28 expression on CRC tumor infiltrating T-cells, while others showed low/absent CD28 expression. Finally, to evaluate the impact of immune cell CD28 and CD80/86 expression on tumor response to immune checkpoint blockades, mice were subcutaneously injected with tumor cells to generate a subcutaneous tumor model. The mice were then treated twice per week with either IgG (control) or with a combination of the checkpoint inhibitors anti-CTLA-4 and anti-PD-1 (ICBT). The results demonstrate that the ICBT treatment restricts early stage tumor development in wild-type mice, while CD28 knockout mice and CD80/86 knockout mice are resistant to this treatment (FIG. 1D). Further, antibody blocking of CD80 and CD86 also induced tumor resistance to the ICBT treatment.

miR-424 Expression is Associated with CD28/C80 Downregulation During Tumor Development We performed predictive analysis to identify potential miRNAs that target CD28, CD80, or CD86, and could be responsible for the downregulation observed in CRC. First, we identified miRNAs that can bind to more than one of the 3'UTRs of the CD28, CD80, or CD86 mRNAs (FIG. 2A). After selecting miR-424 as a promising candidate, we examined miR-424 expression in CRC and normal colon samples using data retrieved from the TCGA database. This analysis revealed that miR-424 expression is substantially higher in CRC tissues as compared to normal colon tissues (FIG. 2B). We confirmed this differential expression by performing in situ hybridization (ISH; FIG. 2C) and qPCR (FIG. 2D) on human CRC samples and normal colon tissues. To confirm that miR-424 can target the 3'UTR of CD28 and CD80, we performed a dual luciferase assay. This assay demonstrated that miR-424 significantly downregulates the expression of luciferase that comprises the 3'UTR sequence of CD28 and CD80 (FIG. 2E). To evaluate the ability of miR-424 to suppress CD28 and CD80 protein expression, we synthesized a miR-424 "mimic", an artificially synthesized functional miRNA. The miR-424 mimic was transfected into naïve T-cells and dendritic cells (DCs), and CD28 and CD80 protein expression was measured by flow cytometry. In this assay, the T-cells transfected with miR-424 mimic showed lower CD28 protein expression, and the DCs transfected with miR-424 mimic showed lower CD80 protein expression (FIG. 2F). Finally, to study the association between miR-424 and anti-tumor immune response, we generated a subcutaneous tumor model by inoculating mice with CT26-WT tumor cells. At various stages of tumor growth, we analyzed miR-424 levels by qPCR and determined immune profiles using flow cytometry. This analysis showed that during tumor growth, the miR-424 level increased gradually, while the CD28 expression on T-cells and CD80 expression on DCs decreased gradually (FIG. 2G).

Figures 3A, 3B, 3C, 3D, 3E, 3F, 3G:
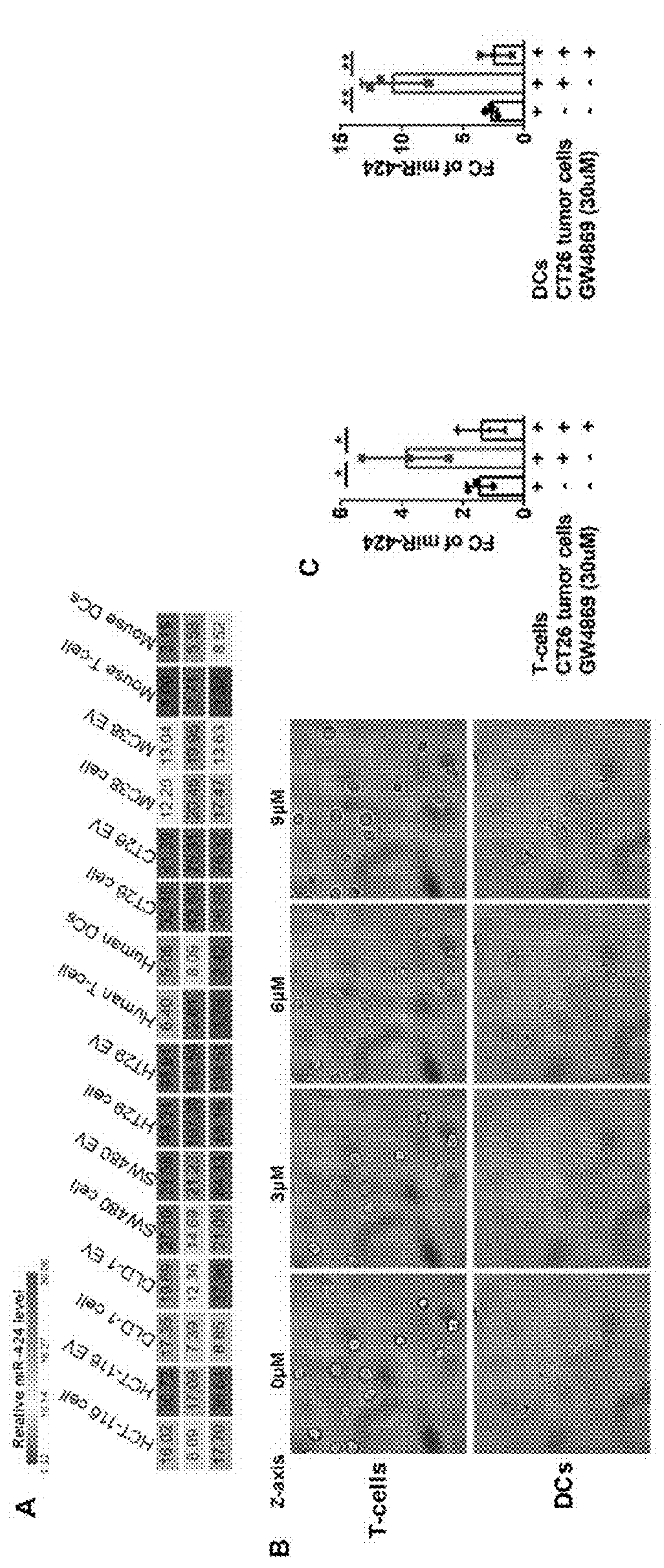
FIGS. 3A-3G.
Figures 3A, 3B, 3C, 3D, 3E, 3F, 3G:
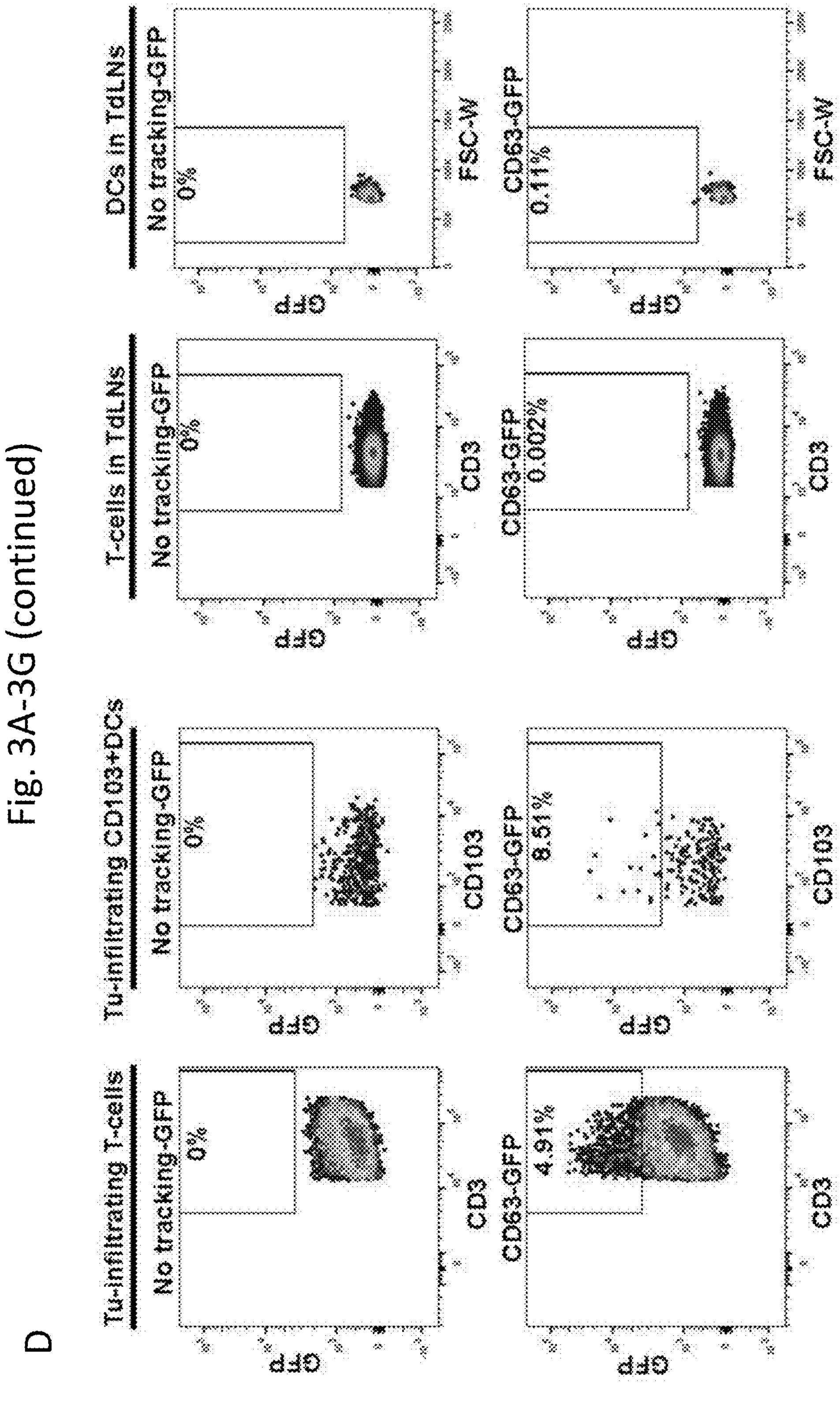
Figures 3A, 3B, 3C, 3D, 3E, 3F, 3G:
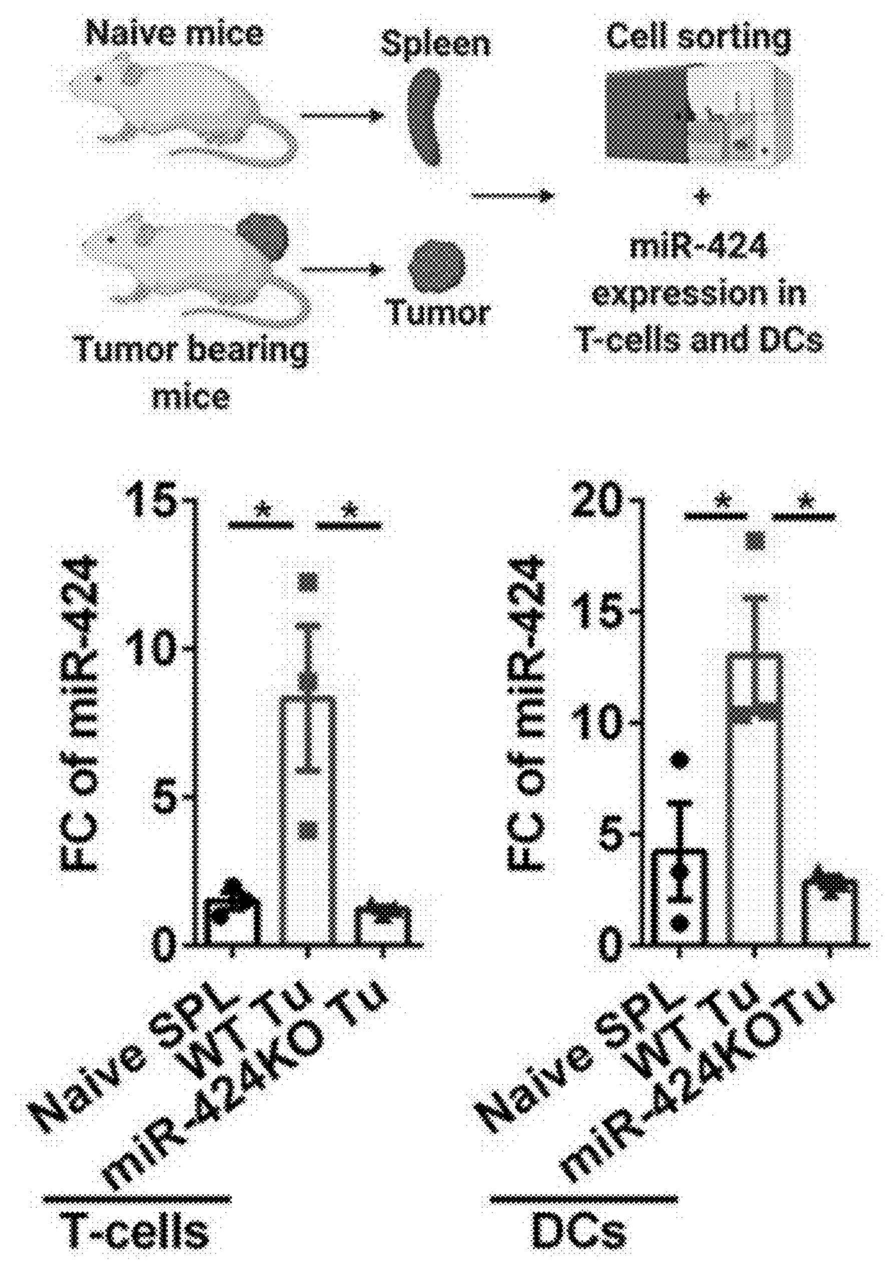
Figures 3A, 3B, 3C, 3D, 3E, 3F, 3G:
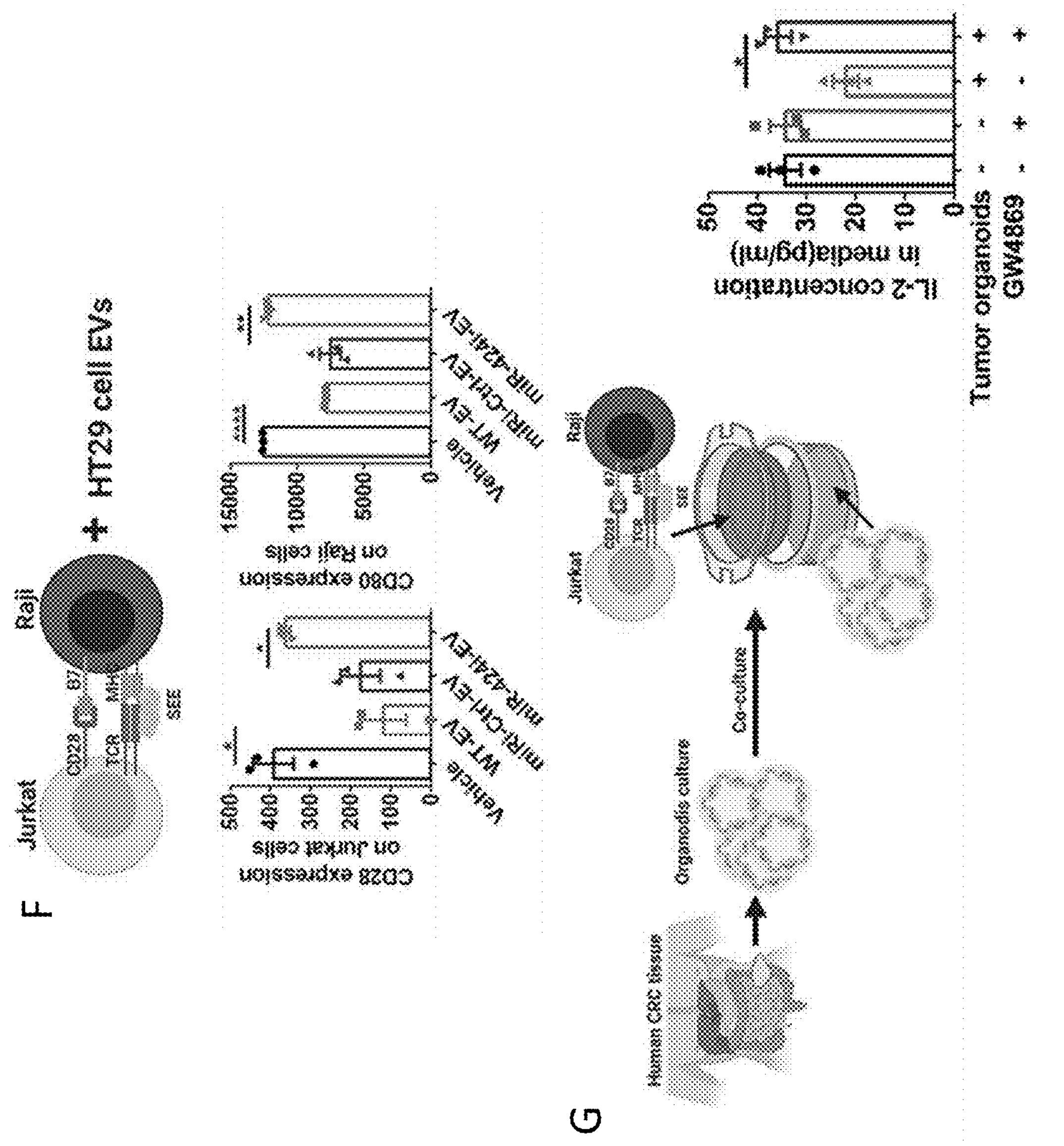

Tumor-Derived EVs are Engulfed by T-Cells and DCs, and Lead to Changes in Immune Cell Function.

miR-424 levels were analyzed across different samples, including tumor cells, immune cells, and EVs (FIG. 3A). To determine whether EVs can be up-taken by T-cells and DCs, CT26-WT cell line-derived EVs were stained with Dio dye and incubated with mouse naïve T-cells and DCs. Images taken using confocal microscopy confirmed the presence of Dio labeled EVs inside the T-cells and DCs (FIG. 3B). Next, CT26 tumor cells were co-cultured with naïve T-cells and DCs, which lead to a significant increase in miR-424 levels in both T-cells and DCs (FIG. 3C). Importantly, this increase in miR-424 could be neutralized by blocking the production of EVs in the co-culture system using GW4869 (FIG. 3C). To determine whether this tumor-derived EVs were being engulfed by the immune cells, CD63-GFP transfected CT26 tumor cells were injected into mice to establish a subcutaneous tumor model. Flow cytometry was then used to detect GFP signal in tumor infiltrating T-cells and DCs (FIG. 3D), demonstrating that that tumor cell-derived EVs were absorbed by T-cells and DCs surrounding the tumor cells. Next, we sought to determine whether these effects could be eliminated by knocking out miR-424 in tumors. To this end, T-cells and DCs were isolated from the spleens of healthy mice, and of mice with wild-type tumors or miR-424 knockout (KO) tumors using flow cytometry sorting. miR-424 level was measured in the sorted T-cells and DCs by qPCR. These results show that T-cells and DCs isolated from wild-type tumors showed higher miR-424 levels than T-cell and DCs isolated from naïve mouse spleen (FIG. 3E). However, T-cells and DCs isolated from miR-424KO tumors showed similar miR-424 levels as T-cell and DCs isolated from naïve mouse spleen (FIG. 3E). Next, to study the impact of EV miR-424 expression on T-cell co-stimulation, the Jurkat cell and Raji cell conjugation assays were used. The EVs added to these conjugation systems were all derived from HT29 cells. In addition to wild-type (WT) EVs, we generated control EVs that express a scrambled sequence (miRi-Ctrl-EV), and EVs that express an anti-miR-424 sequence (miR-424i-EV). While WT-EVs and miRi-Ctrl-EVs decreased CD28 expression on Jurkat cells and CD80 expression on Raji cells, the miR-424i-EVs did not change CD28 and CD80 expression (FIG. 3F). Further, we co-cultured human CRC derived organoids with the Jurkat cell and Raji cell conjugation systems, and demonstrated that the organoids suppressed IL-2 production from both the Jurkat cells and Raji cells (FIG. 3G). However, when GW4869 was used to block EVs secretion in the co-culture system, this effect was neutralized (FIG. 3G).

Characterization of Tumor-Derived EVs.

Figures 4A, 4B, 4C:
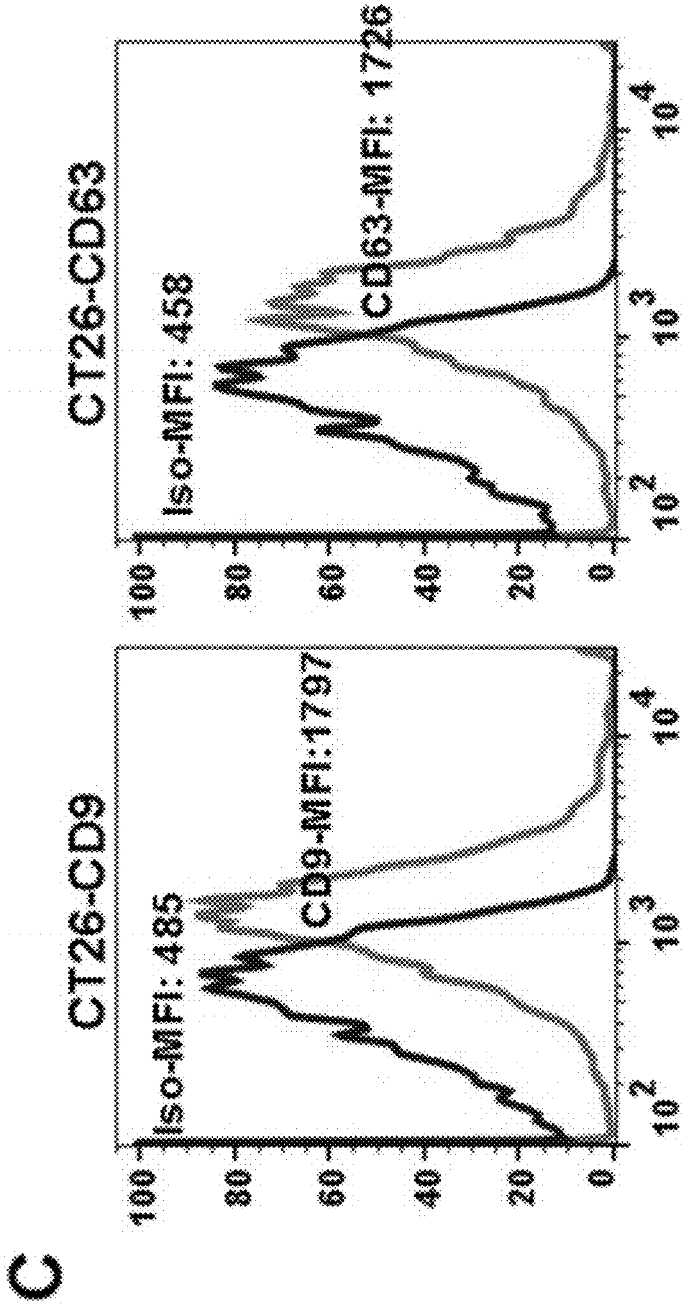
FIGS. 4A-4C.

Transmission electron microscopy was used to capture images of EVs isolated from CT26 tumor cells (FIG. 4A), and the Nanosight system was used to measure the size of the isolated EVs, which were found to range from 60 nm to 300 nm (FIG. 4B). Next, flow cytometry was used to detect CD9 and CD63 protein expression on the surface of the isolated EVs (FIG. 4C).

Inactivation of miR-424 in CT26 Tumor Cells Suppresses Tumor Development by Stimulating Anti-Tumor Immunity.

Figures 5A, 5B, 5C, 5D, 5E, 5F, 5G:
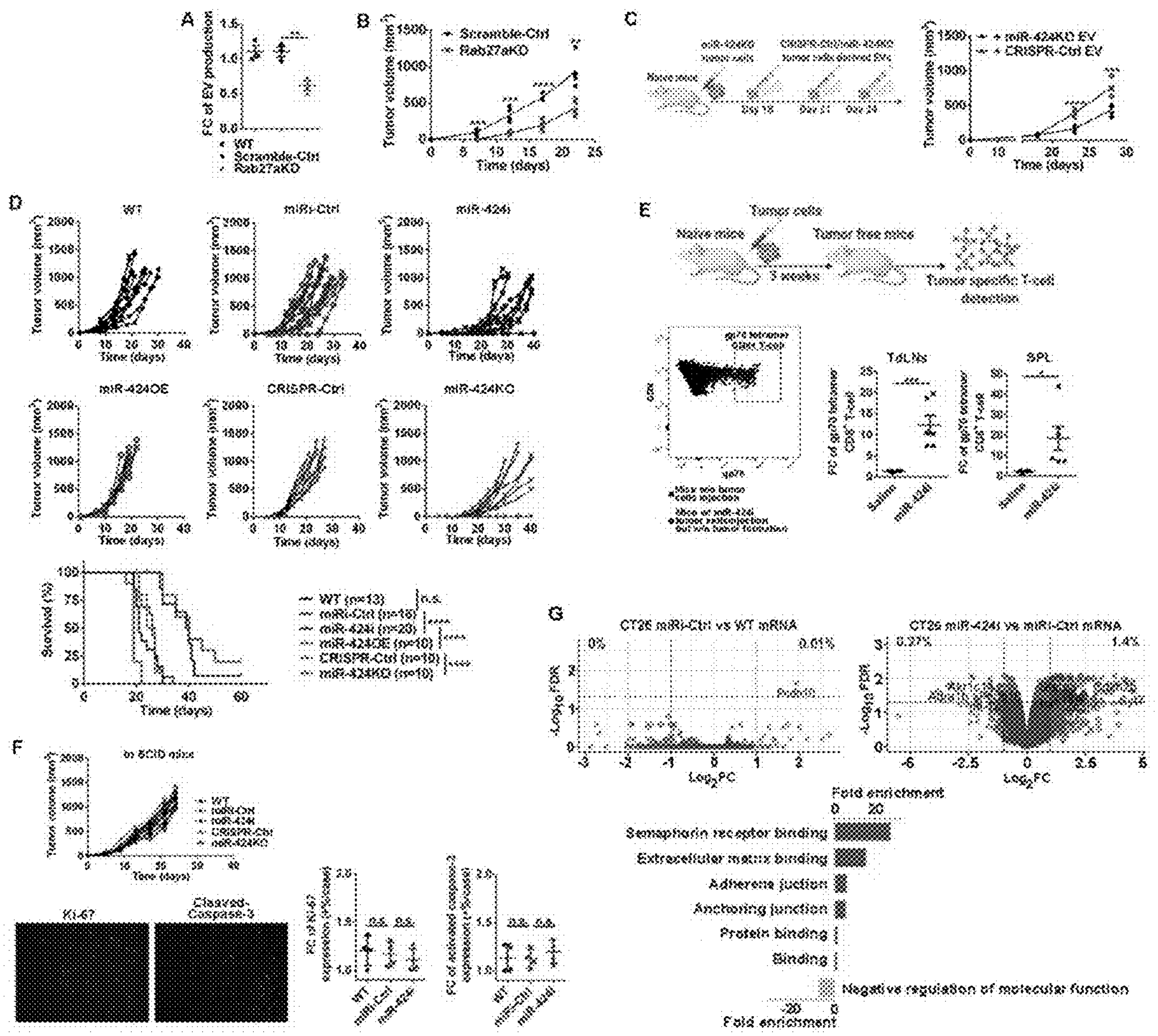
FIGS. 5A-5G.

Rab27a is a small GTPase that is known to play an important role in EV secretion. To study the effects of Rab27a knockdown on tumor growth, we inoculated naïve mice with MC38 cells, either with normal Rab27a expression (Scramble-Ctrl) or reduced Rab27a expression (Rab27aKD). We found that knock down of Rab27a significantly reduced tumor cell extracellular vesicle (EVs) production (FIG. 5A) and suppressed tumor growth in vivo (FIG. 5B). Next, we established a tumor model without endogenous miR-424 expression. We then intratumorally injected syngeneic tumor EVs with miR-424 (CRISPR-Ctrl EV) or without miR-424 (miR-424KO EV) into the tumor and measured tumor growth. We found that exogenously provided EVs with miR-424 enhanced the growth of tumors that do not express endogenous miR-424 (FIG. 5C). To study the effects of miR-424 on tumor growth, we inoculated the naïve mice with tumor cells expressing various forms/levels of miR-424, including: WT cells that express the natural level of miR-424, miRi-Ctrl cells that express a control sequence that doesn't bind to human/mouse miRNAs, miR-424i cells that express a sequence that binds to and blocks miR-424, miR-4240E cells that overexpress a miR-424 sequence, CRISPR-Ctrl cells that express a sequence that doesn't bind to the human/mouse genome, and miR-424KO cells that have miR-424 knocked out from cells' genome. We found that inactivation (miR-424i) or depletion (miR-424KO) of tumor-derived miR-424 suppressed CT26 tumor development and showed a better survival in immune competent mice (FIG. 5D). CD8+ T-cells were isolated from tumor free mice that were injected with miR-424i CT26 tumor cells using flow cytometry (FIG. 5E). The presence of these anti-tumor specific cells demonstrates that an immunological response was mounted against the miR-424i CT26 tumors. To study the effects of miR-424 on tumor growth in an immunodeficient condition, we inoculated SCID mice with tumor cells expressing different forms/levels of miR-424 (discussed above), and evaluated proliferation (Ki-67) and apoptosis (cleaved-caspas-3) in tumor tissues. We found that in immune deficient mice, inactivation or depletion of tumor derived miR-424 didn't influence CT26 tumor development at all, as the proliferative marker (Ki-67) and apoptotic marker (Cleaved-Caspase-3) were similarly expressed in control tumors and tumors with inactivated miR-424 (FIG. 5F). These data indicate that the tumor suppressive effect of eliminating tumor-derived miR-424 functions by stimulating anti-tumor immunity. Finally, we analyzed the effect of inactivation of miR-424 in tumor cells on gene expression by performing mRNA and miRNA sequencing on the WT, miRi-Ctrl, and miR-424i cell lines. Surprisingly, we found that inactivation of tumor cell-derived miR-424 did not stimulate extensive changes in gene expression in CT26 cells.

Figures 6A, 6B, 6C, 6D, 6E:
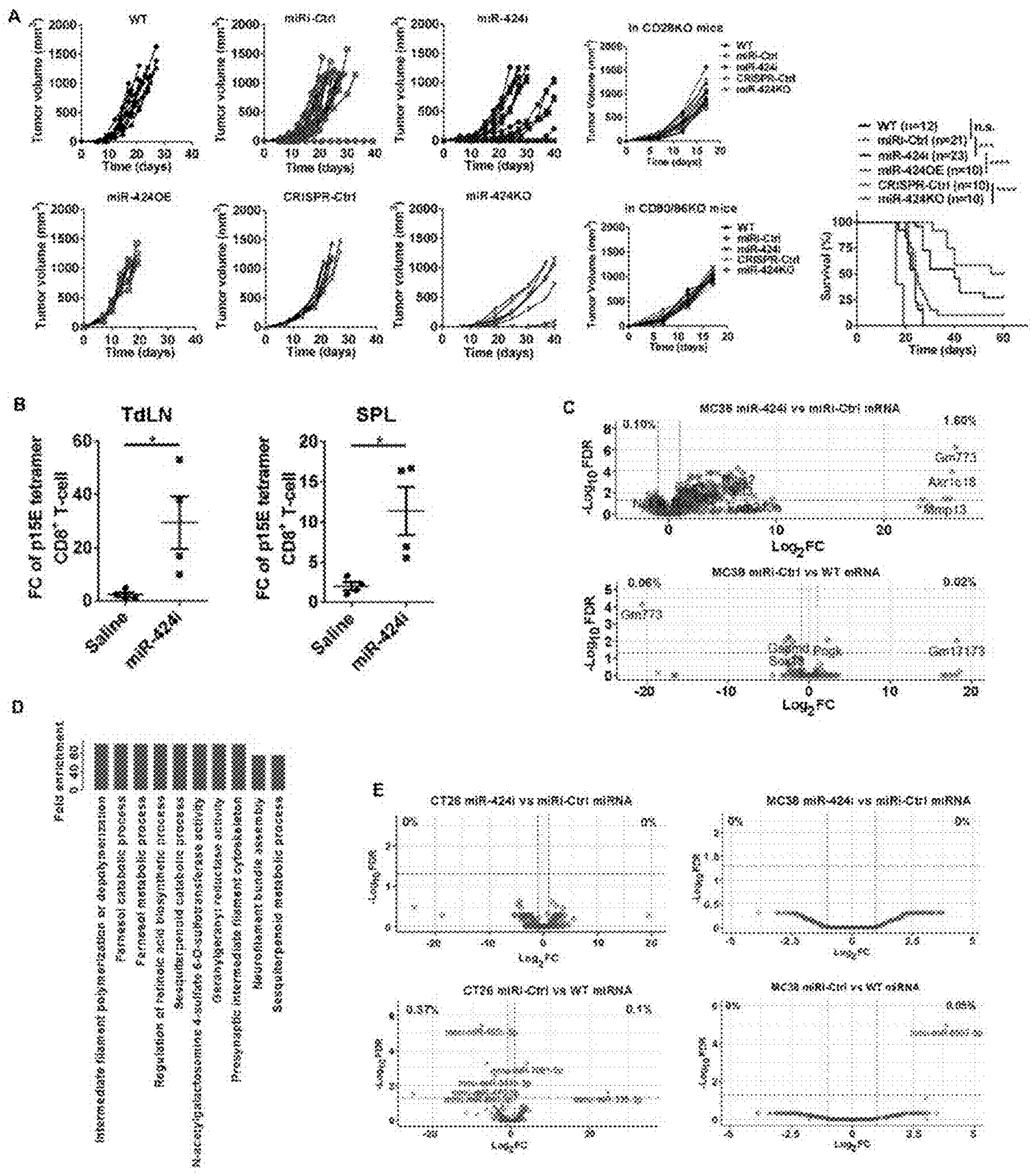
FIGS. 6A-6E.

Inactivation of miR-424 in MC38 Tumor Cells Suppresses Tumor Development by Stimulating Anti-Tumor Immunity We next confirmed that inactivation (miR-424i) or depletion (miR-424KO) of tumor derived miR-424 suppressed MC38 tumor development and resulted in better survival in immune competent mice (FIG. 6A). Importantly, in CD28 knockout and CD80/86 knockout mice, inactivation or depletion of tumor derived miR-424 didn't reduce tumor burden (FIG. 6A). Further, anti-tumor specific immunity was detected in tumor free mice that were injected with miR-424i MC38 tumor cells, indicating the immunological response was generated against the miR-424i MC38 tumors (FIG. 6B). However, inactivation of tumor cell-derived miR-424 did not stimulate extensive changes in the gene expression of MC38 cells, based on mRNA-seq data (FIGS. 6C-6E).

Inactivation of miR-424 in Tumor Cells Sensitizes Tumors to Immune Checkpoint Blockade Therapy.

Figures 7A, 7B, 7C, 7D, 7E:
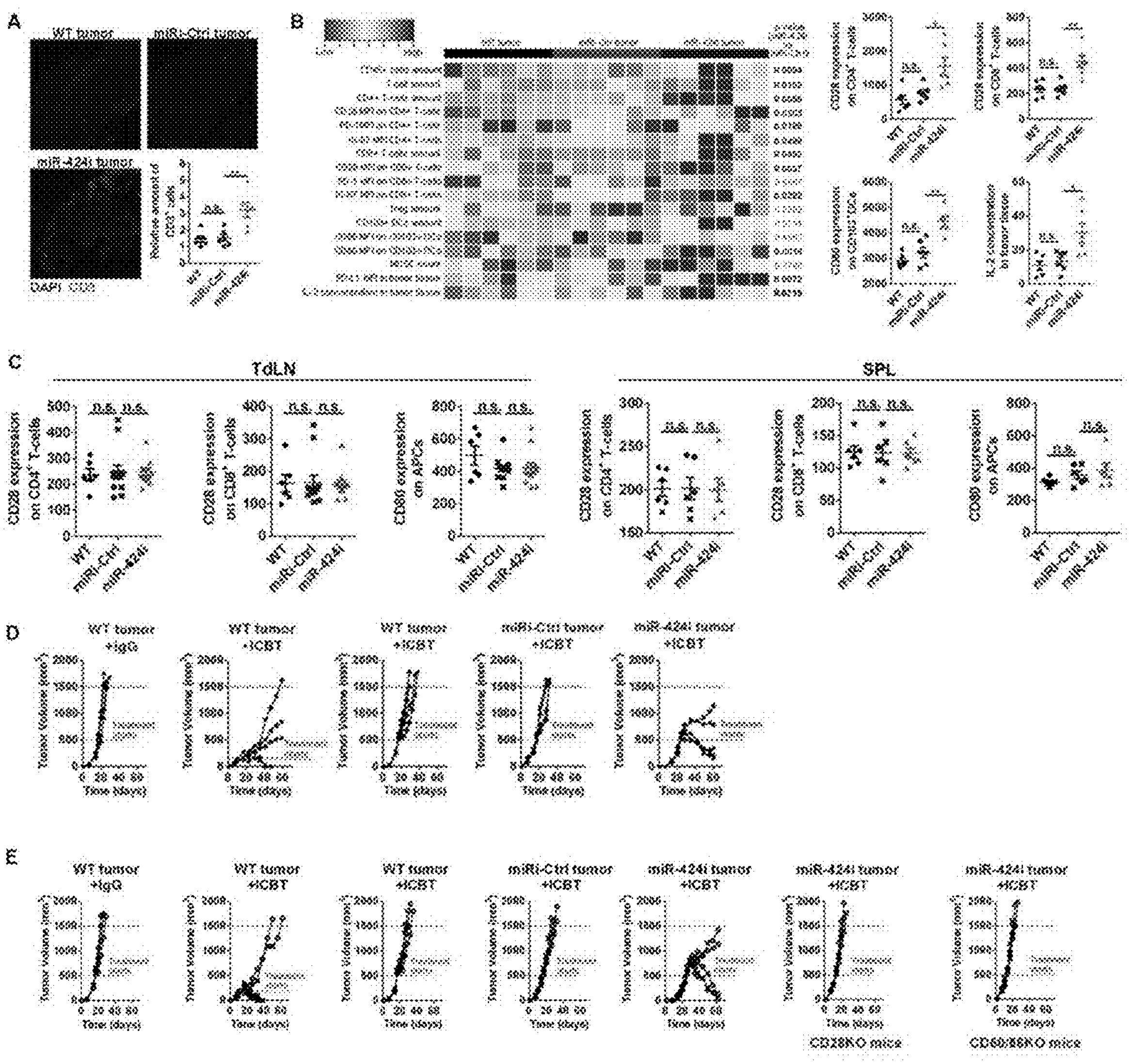
FIGS. 7A-7E.
Figures 8A, 8B, 8C, 8D:
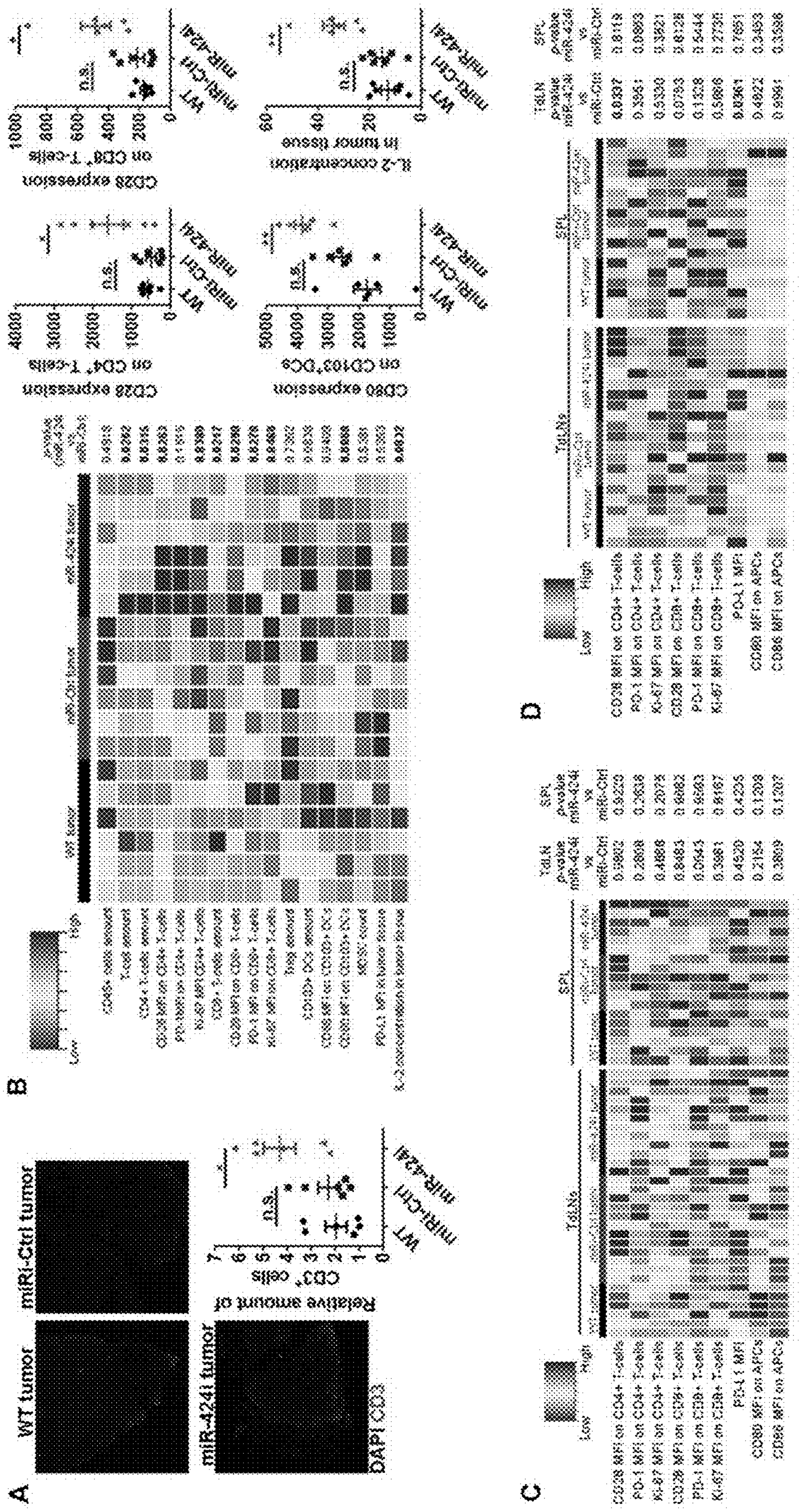
FIGS. 8A-8D.

We performed immunofluorescent staining on primary CT26 tumors (FIG. 7A) and MC38 tumors (FIG. 8A) to show that T-cell infiltration was much higher in tumors with inactivated miR-424 as compared to control tumors. Next, we analyzed the anti-tumor immune profiles in CT26 tumors (FIG. 7B) and MC38 tumors (FIG. 8B), and we observed that the CD28 and CD80 expression levels were significantly higher in tumors with inactivated miR-424 than in control tumors. However, the levels of these markers were not different between these groups in tumor draining lymph nodes (TdLNs) and spleen of tumor bearing mice (FIG. 7C, FIGS. 8C-8D), suggesting that tumor cell-derived miR-424 primarily regulates anti-tumor immunity in the tumor microenvironment, rather than in peripheral immune organs. Next, mice with primary tumors (WT, miRi-424, miR-424i) were treated with an immune checkpoint blockades therapy (ICBT: Anti-CTLA-4 (200 mg/kg)+Anti-PD-1 (200 mg/kg)), twice weekly to study their sensitivity to the treatment. Notably, in the CT26 tumor model, ICBT is effective for treating the small volume tumors but not for controlling the established, large volume tumors (FIG. 7D). Further, blocking the tumor cell-derived miR-424 could enhance the response of established tumors to ICBT (FIG. 7D). Similar results were obtained in the MC38 tumor model (FIG. 7E). Importantly, we showed that ICBT failed to control the miR-424i tumor development in CD28 and CD80/86 knockout mice (FIG. 7E). Thus, we hypothesize that inactivation or depletion of tumor derived miR-424 sensitized the tumors to immune checkpoint blockade therapy (ICBT) by unleashing CD28/CD80 regulated anti-tumor immunity in the tumor microenvironment.

Tumor-Derived EVs with Inactivated miR-424 Pre-Conditions Mice Against Tumor Formation.

Figures 9A, 9B, 9C:
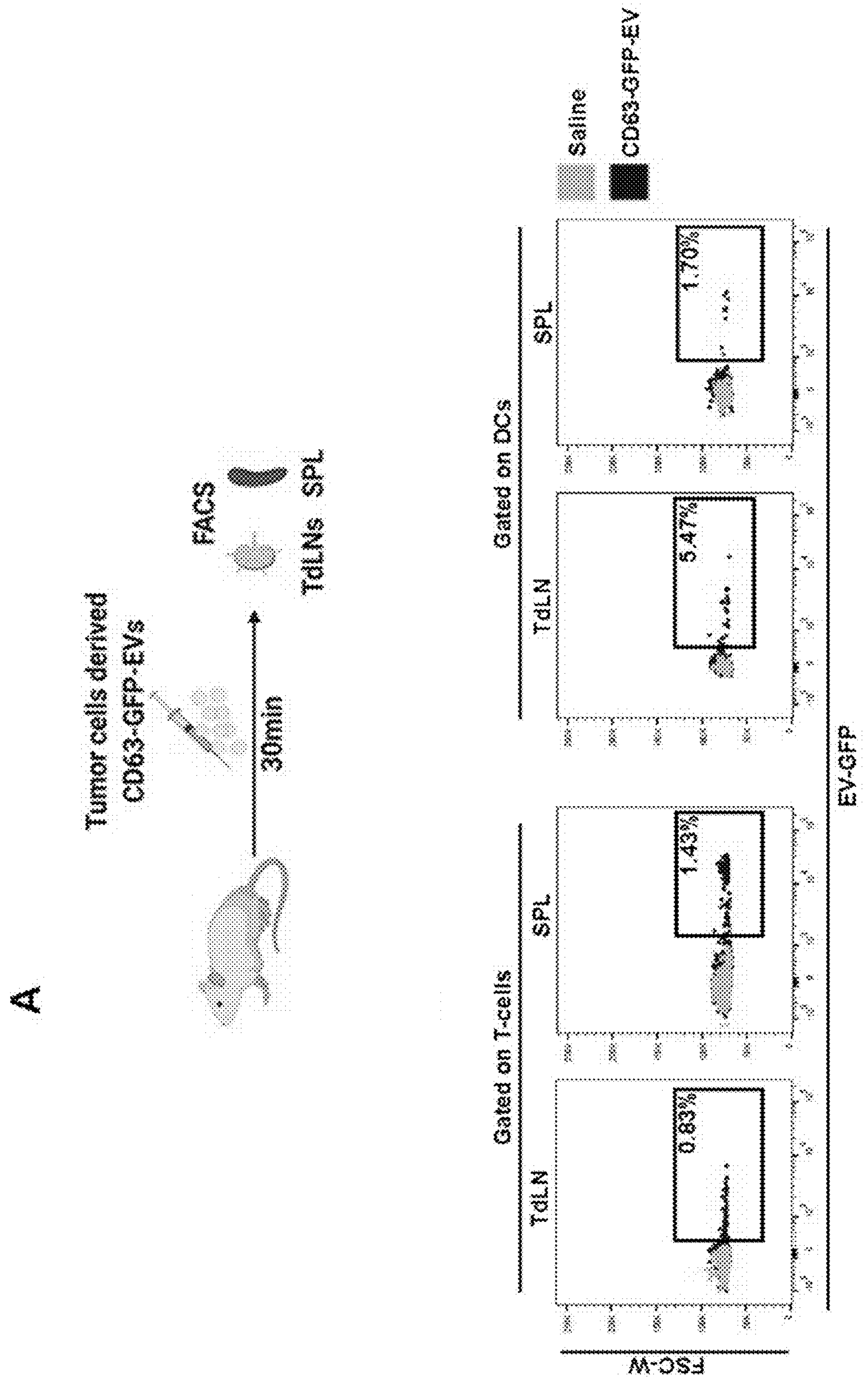
FIGS. 9A-9C.
Figures 9A, 9B, 9C:
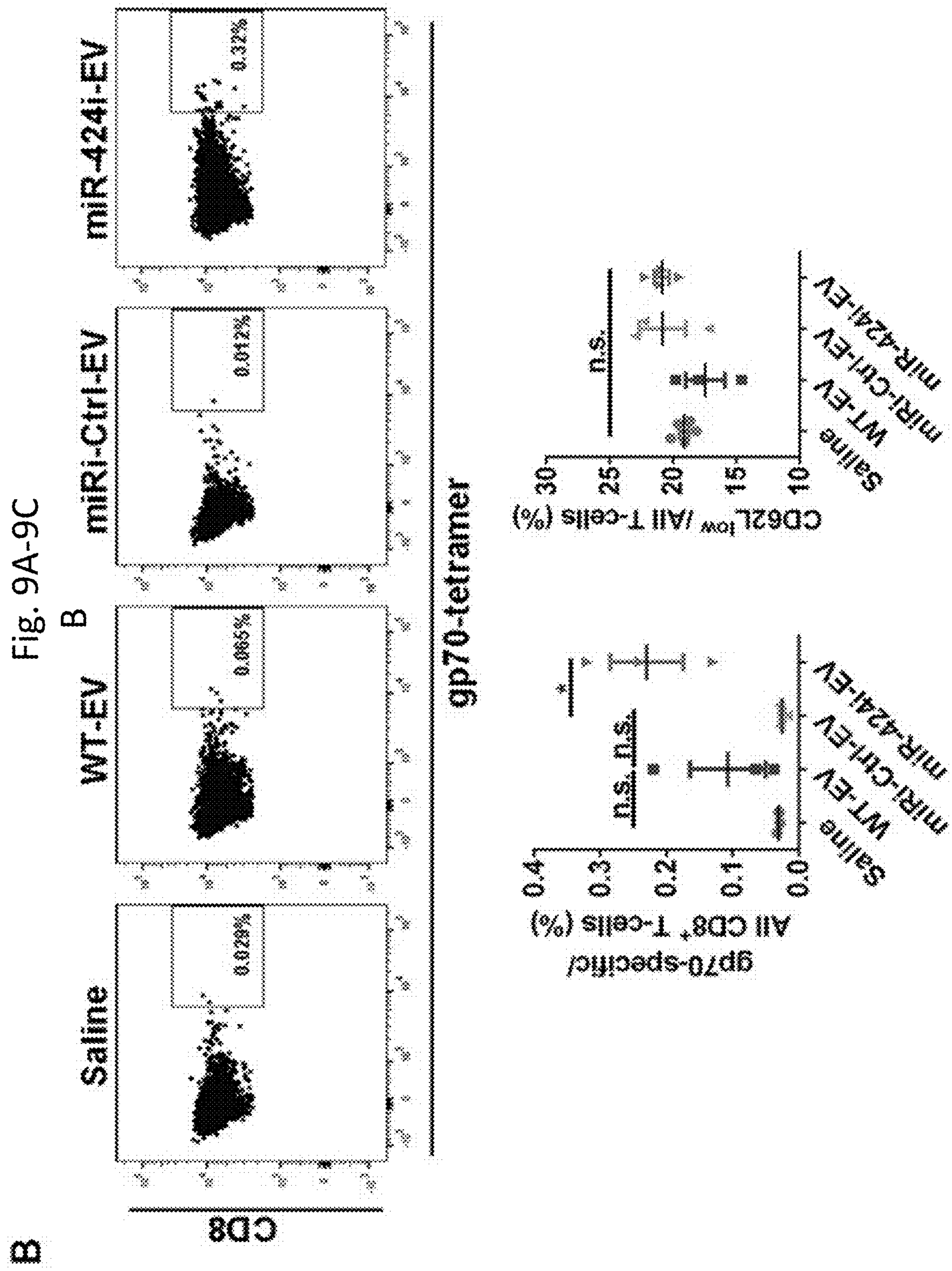
Figures 9A, 9B, 9C:
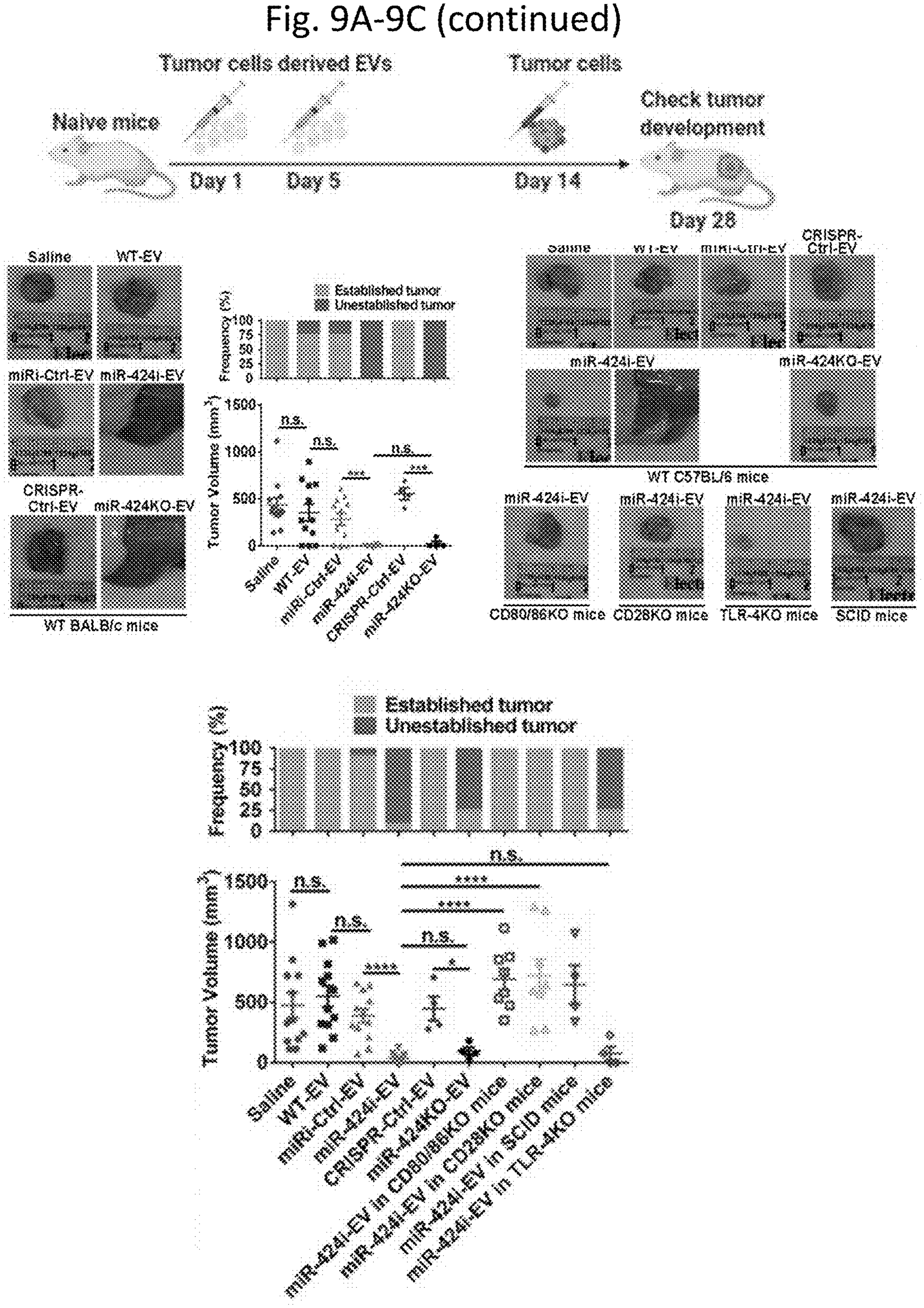

To study EVs biodistribution in immune cells, EVs isolated from different tumor cells (CT26-WT, CT26-miRi-Ctrl, CT26-miR-424i) were labeled with GFP as a fluorescent marker, and 10 ug of labeled EVs were injected intravenously through the tail vein of naïve mice. We first confirmed that the injected EVs were up taken by T-cells and dendritic cells in the peripheral lymphatic organs using flow cytometry (FIG. 9A). We also used flow cytometry to detect anti-tumor specific CD8+ T-cells in peripheral lymphatic organs, confirming that tumor cell-derived EVs with inactivated miR-424 stimulated a tumor specific T-cell expansion in the peripheral lymphatic organs (FIG. 9B). Next, to determine if the EVs could have a pre-conditioning effect, we again injected mice with EVs (10 ug) isolated from different tumor cells (as described above). Two weeks after injection, the mice were inoculated subcutaneously with syngeneic tumor cells to study tumor formation. We found that pre-conditioning naïve mice with tumor cell-derived EVs with inactivated (miR-424i-EV) or depleted (miR-424KO-EV) miR-424 prevented tumor formation and reduced tumor growth in the MC38 and CT26 models (FIG. 9C). Notably, these effects were seen in wild-type (WT) mice and TLR4-KO mice, but not in SCID mice, CD28KO mice, and CD80/86KO mice (FIG. 9C).

Treatment with Tumor-Derived EVs Injection does not Cause Observable Side Effects.

Figures 10A, 10B, 10C, 10D:
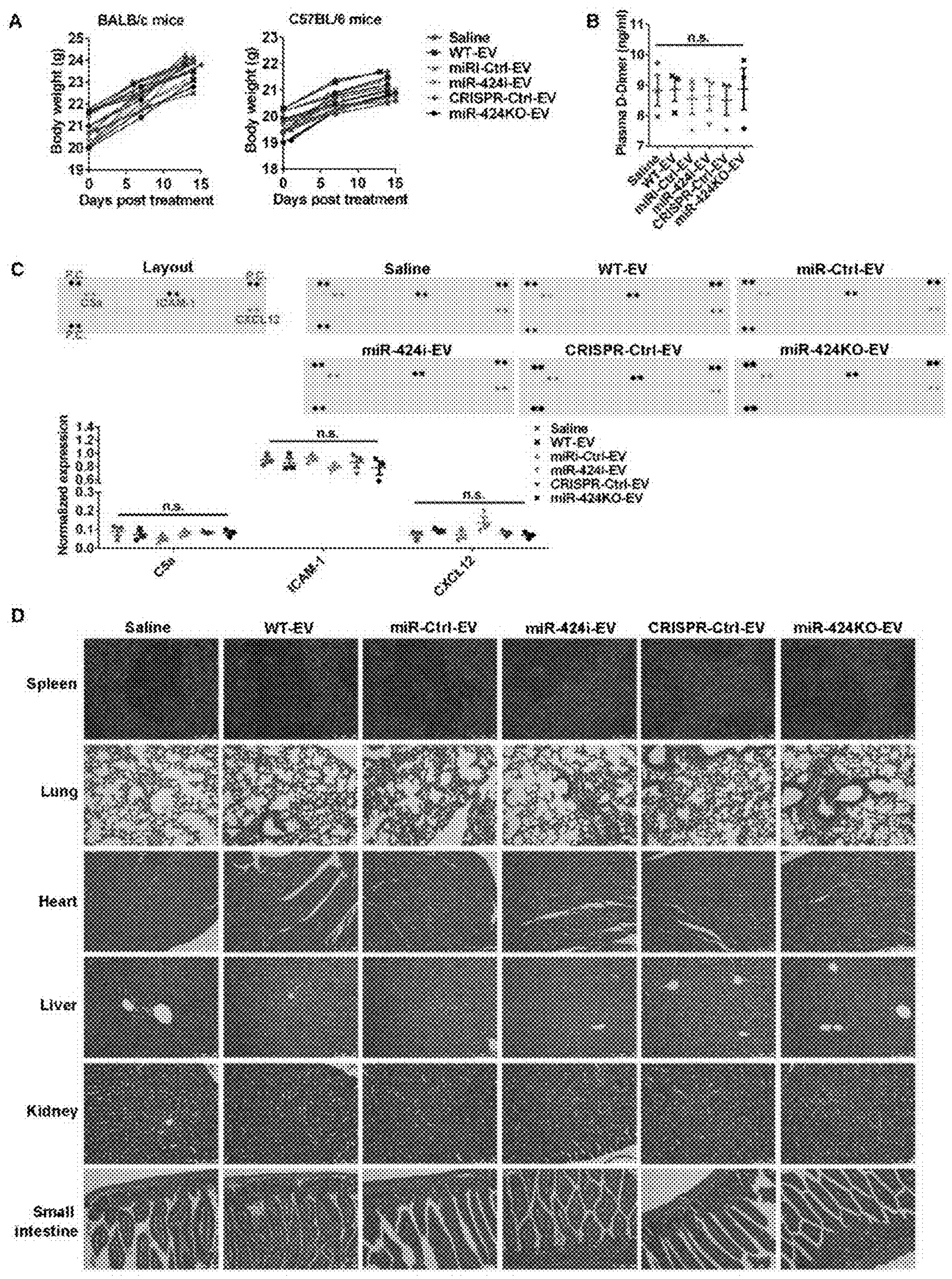
FIGS. 10A-10D.

We next sought to determine the side effects of tumor cell-derived EVs injection (2 doses). Mice that were injected with EVs (10 ug) isolated from different tumor cells and inoculated subcutaneously with syngeneic tumor cells (described in FIG. 9C) were monitored for any signs of side effects resulting from the EV treatment. We found that this treatment did not affect the growth of mice (FIG. 10A), nor did it stimulate extensive thrombosis, as indicated by low D-dimer levels in the serum (FIG. 10B) or non-specifically induce cytokine release, as indicated by cytokine levels in the serum (FIG. 10C). Organs (spleen, lung, heart, liver, kidney, and small intestine) were collected for histological analysis by hematoxylin and eosin staining, which confirmed that the treatment did not cause damage to the major organs (FIG. 10D). Further, no non-specific immune infiltration was observed in those organs (FIG. 10D).

Tumor-Derived EVs with Inactivated miR-424 Sensitize Advanced Orthotopic Tumors to ICBT.

Figures 11A, 11B, 11C, 11D:
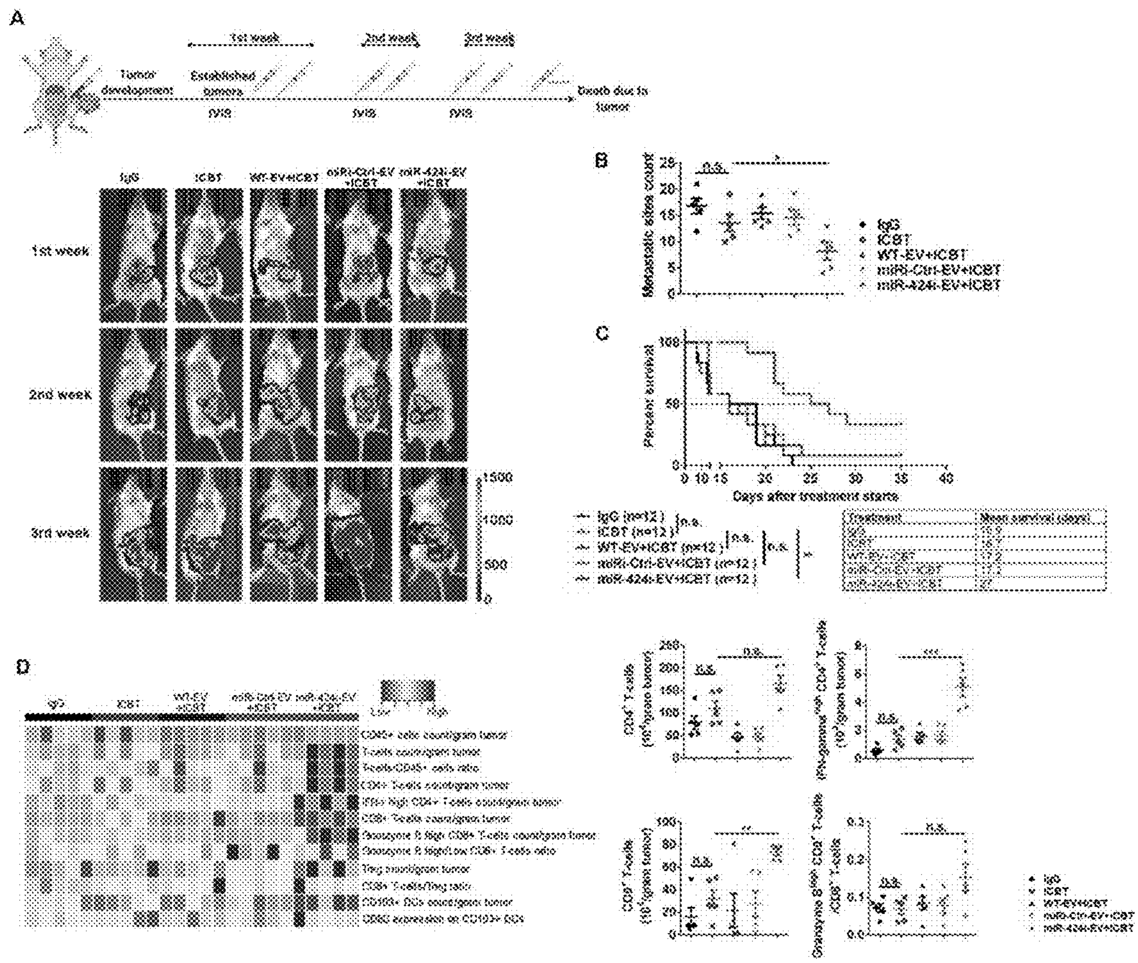
FIGS. 11A-11D.

To establish an orthotopic immunocompetent CRC model, CT26-Luc tumor cells were implanted in the cecum of naïve mice. Tumor development was monitored periodically by in vivo imaging (FIG. 11A). When the mice had established tumors, they were treated with one of five treatments: 1. IgG 400 mg/kg, twice weekly; 2. Anti-CTLA-4 (200 mg/kg)+Anti-PD-1 (200 mg/kg), twice weekly; 3. CT26-WT-EV (10 ug, twice weekly for one week)+ Anti-CTLA-4 (200 mg/kg)+Anti-PD-1 (200 mg/kg), twice weekly; 4. CT26-miRi-Ctrl-EV (10 ug, twice weekly for one week)+Anti-CTLA-4 (200 mg/kg)+Anti-PD-1 (200 mg/kg), twice weekly; 5. CT26-miR-424i-EV (10 ug, twice weekly for one week)+Anti-CTLA-4 (200 mg/kg)+Anti-PD-1 (200 mg/kg), twice weekly). Note: ICBT means Anti-CTLA-4 (200 mg/kg)+Anti-PD-1 (200 mg/kg), twice weekly. Mice were either sacrificed after two weeks of treatment and evaluated for disease burden and immune infiltration or were monitored until death due to the disease. We found that miR-424i-EV+ICBT treatment significantly reduced the metastatic tumor burden after two weeks treatment (FIG. 11B) and significantly improved survival (FIG. 11C) compared to the ICBT treatment. When we compared the immune profiles of tumors treated by the different therapies, we found that the miR-424i-EV+ICBT treatment increased the T-cell count and function in the tumor microenvironment (FIG. 11D).

Characterization of the Orthotopic Cecum Model

Figures 12A, 12B, 12C:
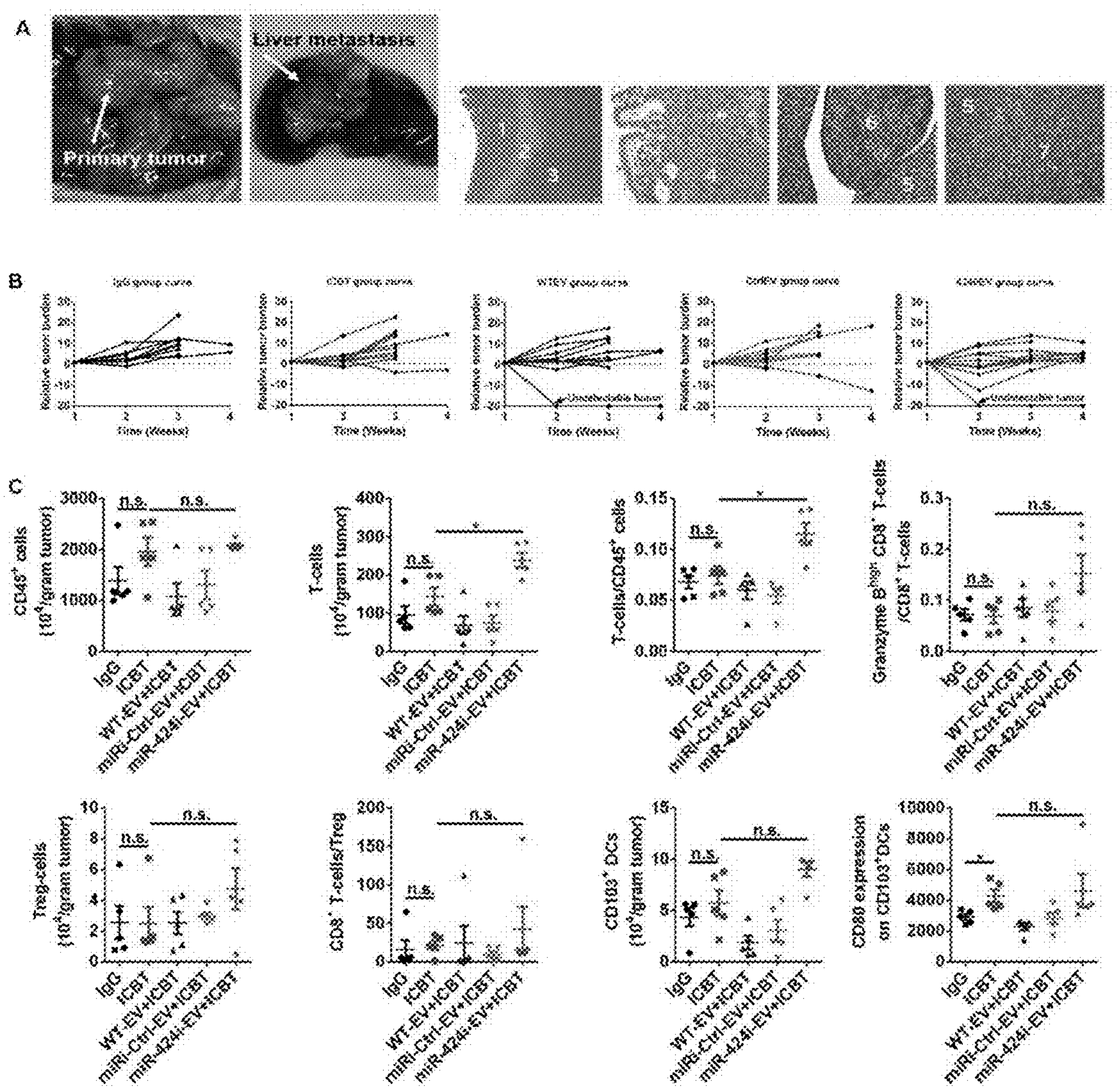
FIGS. 12A-12C.

We examined the morphology of the primary tumors and liver metastatic lesions as well as the histology of the primary tumors (FIG. 12A). Further, we analyzed the growth of individual tumors (FIG. 12B) and the expression of various immune markers (FIG. 12C) in mice from each treatment group.

Materials and Methods:

Experimental Model and Subject Details

Human Samples

Human colorectal cancer (CRC) biospecimens and cancer patients' peripheral blood were consented and collected through the Biological Materials Procurement Network (BioNet) of the University of Minnesota and the Cooperative Human Tissue Network, under an IRB approved protocol. Formalin-Fixed Paraffin-Embedded (FFPE) samples were used for immunofluorescent imaging studies and freshly excised samples were used for flow cytometry and qRT-PCR analyses. All freshly resected samples were placed in ice-cold PBS or RMPI-1640 medium in a 50 mL conical tube and immediately transported to the laboratory for processing. Healthy donor-derived peripheral blood was provided by the memorial blood centers with an approved IRB protocol. All human CRC tumors collected were treatment naïve.

Tumor Cell Lines

Human CRC cell lines HT116 (ATCC, CCL-247), HT29 (ATCC, HTB-38), DLD-1 (ATCC, CCL-221), and SW480 (ATCC, CCL-228) were purchased from the American Type Culture Collection (ATCC). Mouse CRC cell line CT26 (ATCC, CRL-2638) was purchased from the ATCC. Mouse CRC cell line MC38 was kindly provided by Dr. Nicholas Haining. Human Jurkat cells (ATCC, TIB-152) and Raji cells (ATCC, CCL-86) were purchased from ATCC. Jurkat cell, Raji cells, CT26 cells, and DLD-1 cells were maintained in complete RPMI-1640 medium (GIBCO BRL), supplemented with 10% heat-inactivated FBS (Thermo Fisher Scientific), 100 IU/mL penicillin, and 100 μg/mL streptomycin (Invitrogen Life Technologies). SW480 cells and MC38 cells were cultured in the complete DMEM medium (GIBCO BRL) and HCT116 and HT29 cells were cultured in McCoy's 5a Medium (Thermo Fisher Scientific) with the same supplements as the RPMI 1640 medium. All cells were routinely authenticated and tested for *mycoplasma.*

Derivatives of these parental cell lines were established for different experimental proposes. CT26-Luc, a derivative of CT-26, was created through transduction of CT26 with a firefly luciferase expression construct, for in vivo tumor imaging. The CT26/MC38-miR-424KO cell lines were constructed by the CRISPR/Cas9 technology and single clone selection. The guide RNA that flanking the miR-424 was shown in Table 1. The CT26/MC38-miR-424i and CT26/MC38-miR-424OE were established by transducing the wild-type cells with constructs that express anti-miR-424 sequence (miR-424i) or miR-424 sequence (miR-4240E). To knockdown the Rab27a expression (Rab27aKD), we transduced the MC38 cell line with a shRNA library that would express five different Rab27a-targeting siRNAs. Vectors that express scramble sequences were used to establish the control (Ctrl) cell lines for the genetically edited cell lines. The lentiviral system (HEK-293T cells (ATCC, CRL-3216), Lipofectamine™ 3000 Transfection Reagent (Invitrogen), and pPACKH1-XL packaging vector (SBI) was used for making stably edited cell lines. The manufacture information of each construct was listed in Table 1.

Mice

Animal studies were approved by the institutional animal care and use committee (IACUC) of the University of Minnesota. All mice were kept in a specific pathogen-free conditions with fully autoclaved cages to minimize non-tumor specific immune activation. The following mice were purchased from the Jackson Laboratory: BALB/cJ, B6.129S2-Cd28$^{tm1Mak}$/J, Mouse: B6.129S4-Cd80$^{tm1Shr}$ Cd86$^{tm2Shr}$/J, NOD.CB17-Prkdc$^{scid}$/J, B6.CB17-Prkdc$^{scid}$/SzJ, and B6 (Cg)-Tlr$^{4tm1.2Karp}$/J. The C57BL/6 mice were purchased from The Charles River Laboratories. Mice were bred in house and were used for experiments at age from 6-8 weeks.

Method Details

Immunofluorescence

Sections of FFPE tissues were deparaffinized with xylene, rehydrated with gradient ethanol, and subjected to antigen retrieval with heated antigen retrieval butters (AR6 Buffer or AR9 Buffer, PerkinElmer). After 30 min in 5% Bovine serum albumin (BSA) blocking buffer, permeabilization was performed for intracellular staining by incubating the sections for 10 min with PBS containing 0.25% Triton X-100. Primary antibodies were then applied and incubated overnight at 4° C. Then the sections were washed and incubated with secondary antibodies (1:1000 dilution) for 1 h at room temperature. Slides were then washed and mounted with ProLong Gold anti-fade mounting medium (Invitrogen) for imaging. For the multiplex immunofluorescent assays, we used the Opal 7-Color Automation IHC Kit (PerkinElmer). The assays were optimized and performed by following the instruction provided in the Kit.

The primary anti-human antibodies included CD3 (1:100, Clone CD3-12), CD8 (1:100, Clone 144B), E-cadherin (1:200, Clone M168), CD28 (1:50, Polyclonal), CD80 (1:100, Clone 2A2), CD86 (1:100, Clone EP1158Y), and CD11c (1:100, Clone EP1347Y and ITGAX/1242). Anti-mouse primary antibodies included Ki-67 (1:100, Polyclonal), cleaved-caspase-3 (1:50, Polyclonal), and CD3 (1:100, Clone CD3-12). Quantitative image analysis was performed by counting positive percentage and evaluating fluorescent signal intensity in at least three randomly selected fields of each section. The manufacture information of each antibody was included in the Table 1.

Mouse Subcutaneous Model $2*10^5$ CT26 tumor cells or $5*10^5$ MC38 cells resuspended in 100 μl matrigel (BD Biosciences) were injected to the right flank of BALB/c background or C57BL/6 background mice respectively. For tumor measurements, tumors were typically measured 2-3 times per week using an electronic caliper. Tumor volume was calculated through the formula Volume=(Width$^2$*Length)/2. Mice were considered as death when tumors exceeded the volume of 1000 mm$^3$ or 1500 mm$^3$ depending on the experimental setup.

Mouse Cecum Orthotopic Model

Mouse cecum orthotopic CRC model was established for evaluating the impacts of modified tumor cell-derived EVs on immune checkpoint blockades response. 2-4 hours before surgery, Buprenorphine (SR) 2 mg/kg is administered subcutaneously for pre-emptive analgesia. Then, mice are anesthetized with ketamine (100 mg/kg)/xylazine (10 mg/kg). We then position the mouse on its back on fix the forelegs in a V shape with tape. The abdomen of the mouse was shaved, and skin was prepared by wiping with Povidone-iodine prep pads and then alcohol prep pad. CT26 cells were resuspended in matrigel. The surgical area was isolated by placing the sterile drape around the incision area on top of the abdomen. A 15 mm vertical midline incision was made on the skin. We then incised the linea alba to separate the rectus abdominis muscles and opened the abdomen. The cecum was located and carefully placed horizontally on top of a histo-cassette. A matrigel drop containing the CT26 cells ($2*10^5$) was inoculated under the serosa layer. The inoculation site was carefully wiped by alcohol pad to remove any potential leaking. The cecum was placed back into the abdomen using cotton swabs drenched in PBS. The abdominal wall and skin opening were then closed. Mice were monitored for at least 7 days, more analgesics were given when needed.

Mouse Treatment

Mice were treated with IgG (10 mg/kg as an anti-CTLA-4 or anti-PD-1 control), anti-PD-1 (10 mg/kg, clone: RMP1-14), and anti-CTLA-4 (10 mg/kg, clone: UC10-4F10-11) for treatment purpose. For blocking the CD80 and CD86 signaling, we administrated anti-CD80 (40 mg/kg, clone: 16-10A1, twice per week) or anti-CD86 (40 mg/kg, clone: GL-1, twice per week) to the mice one day before anti-CTLA-4/anti-PD-1 treatment starts. All antibodies were given intraperitoneally and continued until the endpoint of study design. For EVs treatment, we injected 15 μg EVs through the tail vein injections. The treatment starting points and endpoint varied in different experimental setups for different purposes and were shown in the individual figure.

Enzyme-Linked Immunosorbent Assays (ELISAs) for IL-2 and D-Dimer

ELISA was performed to measure IL2 in tumor tissue using ELISA kits from Invitrogen according to manufacturer's protocol. All samples were normalized based on protein concentrations measured using a BCA protein assay (Pierce Chemical) before loading. To measure the intensity of coagulation upon EVs treatment, we collected mouse plasma and measured the D-dimer concentration according to manufacturer's instruction (Mouse fibrin degradation product D-Dimer ELISA Kit from LSBio).

Histology Analysis

The haematoxylin Eosin (H&E) staining was performed to analyze tissue histology.

The H&E staining kit was purchased (Abcam) and the manufacture's instruction was followed as the staining protocol.

Locked Nucleic Acids and In Situ Hybridization (LNA-ISH)

ISH for miRNAs was carried out on FFPE colon cancer and normal colon sections with Double-DIG labeled LNATM probe for miR-424 (Qiagen) using miRNA ISH optimization Kit (BioChain). Double-DIG labeled probe for U6 (Qiagen) was used as positive control. Double-DIG labeled scrambled microRNA (Qiagen) was used as negative control. We followed the manufacture's protocol for the ISH procedure. The temperature for probe incubation was optimized based on the probe's Tm. Counterstaining was performed with Nuclear Fast Red™ (Sigma) and mounted with Eukitt quick-hardening mounting medium (Sigma).

Human CRC Organoids Culture

Surgically resected human CRC tissue or biopsy samples were obtained from the BioNet, University of Minnesota. Fresh tumor tissue was processed as previously described (Long-term expansion of epithelial organoids from human colon, adenoma, adenocarcinoma, and Barrett's epithelium." Gastroenterology 141.5 (2011): 1762-1772) with few modifications. Briefly, the tissue was cut into small pieces and washed with ice-cold PBS several times until the solution appears clear with no connective tissues and debris. The tissue was subsequently digested with digestion buffer (DMEM, 2.5% FBS, Penicillin/streptomycin, 75U/mL collagenase IV) for 60 min at 37° C. on a shaker. The digested tissue was passed through 70 μM cell strainer to remove any debris and large fragments. The cells were centrifuged at 300 g for 3 mins at 4° C. The cell pellet was suspended in matrigel (growth factor reduced) at 3000 cells/well and 33 μL of the cell suspension was dispensed in a 24 well culture plate. The matrigel was allowed to polymerize in the incubator at 37° C. The organoids were cultured in advanced ADMEM supplemented with penicillin/streptomycin, 10 mM HEPES, 1× Glutamax, 1×B27, 1×N2, 1 mM N-acetylcysteine, 100 ug/mL Primocin and 10 nM Gastrin. The following niche factors were used: 10 μM SB202190, 10 μM Y-27632, 50 ng/ml human EGF, 0.5 mM A83-01, 10 nM Prostaglandin E2, 10 mM Nicotinamide and 50% L-WRN conditioned media (Wnt, R-spondin and Noggin). The organoids were passaged every week by incubating in TrypLE Express for 5 mins at 37° C. and plated in a new 24 well plate. Fresh complete medium was supplemented every 2 days.

Cytokine Array

We purchased the Proteome Profiler Mouse Cytokine Array Kit (Panel A) to detect cytokines in mouse serum. Serum was isolated from the whole blood drawn from the mice treated with either wild-type or modified tumor cell-derived EVs. 100 ul of mouse serum was used for each membrane (determined by preliminary experiments). We followed the manufacture's instruction for all experimental steps.

Isolation of Extracellular Vesicles (EVs)

For EVs isolation from cell culture supernatants, cells were cultured in media supplemented with 10% exosome depleted FBS (Gibco). Supernatants were collected from 24 h cell cultures and EVs were purified by a standard differential centrifugation protocol. In brief, culture supernatants were centrifuged at 300 g for 10 min to remove cells. The supernatant was then centrifuged at 3,000 g for 10 min to remove dead cells. Debris was pelleted after centrifugation at 10,000 g for 30 min. Supernatants were then centrifuged at 100,000 g for 70 min at 4° C. (Beckman Coulter). The pelleted EVs were suspended in PBS and collected by ultracentrifugation at 100,000 g for 70 min at 4° C. again to minimize protein. The similar method was used to isolate human CRC organoid-derived EVs. To block the EVs production from tumor cells and tumor organoids, 30 μM GW4869 was added to the culture medium.

Characterization of Isolated EVs

For verification of purified EVs using electron microscopy, purified EVs were suspended in PBS were dropped on formvar carbon-coated nickel grids. After staining with 2% uranyl acetate, grids were air-dried and visualized using a Tecnai G2 Spirit BioTWIN transmission electron microscope.

The size and concentration of EVs isolated from cell culture supernatants were determined using a NanoSight LM-10 instrument (Malvern Instruments), which is equipped with fast video capture camera and particle-tracking software. Five independent fields were captured and analyzed for each sample. The data was then merged to a single histogram plot.

The isolated EVs were also tested for protein markers. Aldehyde/sulfate beads (10 μl, Life Technologies) were added to 200 μl EVs (10 μg). The beads and EVs mixture were mixed using a benchtop rotator for 15 minutes at room temperature. 600 μl PBS was then added to the solution and mixing was continued overnight at 4° C. Then 400 μl glycine (1M) was added, mixed, and incubated for 1 h at room temperature. The solution was then spun down and the pellet was resuspended in 100 μl of 10% BSA in PBS and incubated for 1 h at room temperature. The beads were pelleted down again and resuspended in 100 μl of FACS staining buffer and stained for CD63, CD9, or an isotype control for 30 min at room temperature. The beads were washed 3 times with PBS before analyzing by a BD FACSCanto analyzer.

Mouse In Vivo Imaging

To monitor orthotopic CRC tumors established by CT26-Luc cells, we used the IVIS Spectrum in vivo imaging system (PerkinElmer, Waltham, MA). We injected mice with D-Luciferin, GoldBio (150 mg/kg, intraperitoneally) 10 minutes before imaging. The mice were then anesthetized with isoflurane. For all mice, we set exposure time of imaging as 60 sec and used the 540 nm filter for signal collection.

Dual Luciferase Assay

The 3'UTR of human and mouse CD28 and CD80 genes were cloned with sticky ends (XhoI and NotI) on both sides. The dual luciferase backbone plasmid (with its original multiple cloning site linker sequence) were purchased from Promega. Successful insertion of the cloned 3'UTR DNA into backbone plasmids was validated by enzyme digestion and sequencing. To construct the mutated 3'UTR (3'UTR-mut) vector, the binding sequences of miR-424 were replaced by sequences that are not complementary to the miR-424 in the wild-type 3'UTR vector. Finally, the new constructions' concentration was measured by NanoDrop 2000 (Thermo Scientific).

1 μg of constructed dual luciferase vectors and 100 nM synthesized miR-424 mimic (ThermoFisher Scientific) were co-transfected into HEK-293T cells in twenty-four-well plates using lipofectamine 3000 for 24 h. Triplicates were used in each cell experiment. Scramble mimic with none target in human/mouse genome served as negative control for miRNA. Cells treated with transfection vehicle only were applied for the mock group. After transfection, protein in each well was harvested using passive lysis buffer and detected for luciferase activity using Dual-Luciferase® Reporter Assay System (Promega) by a plate reader. The relative luciferase activity value was achieved using firefly luciferase signal intensity against the renilla luciferase control. The result was further expressed as a fold change of the vehicle group.

T-Cells and APCs In Vitro Assays

Primary human T-cells were purified from healthy human peripheral blood monocellular cells (PBMCs). Briefly, the human PBMCs were isolated by gradient centrifugation. Then the Dynabeads™ Untouched™ Human T Cells Kit (Invitrogen) was used to purify naïve T-cells from PBMCs. We followed the manufactures' protocol for detail procedures. To activate the isolated naïve T-cells, the recombinant IL-2 (30 U/mL) and Dynabeads™ Human T-Activator CD3/CD28 (25 μl per $1\times10^6$ T-cells) were added to the cell culture. The activated human T-cells were cultured for up to seven days.

Primary human dendritic cells (DCs) were induced from PBMCs. PBMCs were culture in complete RPMI medium, supplemented with 250 IU/mL IL-4 and 800 IU/mL GM-CSF, and incubated at 37° C. and 5% $CO_2$ for two days. Then the cells were centrifuged and resuspended in complete RPMI medium supplemented with fresh 2000 IU/mL IL-4 and 2000 IU/mL GM-CSF. On day 6, cells are resuspended in complete medium supplemented with 2000 IU/mL IL-6, 400 IU/mL IL-1B, 2000 IU/mL TNF-α, and 100 ng/mL LPS, and cultured for another 24 hours. On day 7, viability, yield, and absolute cell count of induced DCs is determined by flow cytometry (CD14, CD1a, HLA-DR, CD80) and used for further experiments.

Mouse PBMCs were isolated from mouse spleen and inguinal, axillary, and brachial lymph nodes with the similar method. Mouse T-cells and DCs were purified or induced from PBMCs with the similar methods as used in human. To transfect T-cells and DCs with synthesized miR-424, we performed electroporation (Neon, Invitrogen). 100 nM miR-424 was used and a standard protocol was followed.

To study the impacts of tumor cell-derived EVs on the interaction between T-cells and APCs, we used the Jurkat and Raji cell co-culture system. For cell conjugation assay, Raji cells were pre-incubated with 30 ng/ml SEE superantigen (Toxin Technology) alone in RMPI medium for 30 min at 37° C. Cells were then washed by PBS for twice to remove free SEE. After antigen loading, 0.3 million antigen-loaded Raji B cells and 0.3 million Jurkat T-cells were mixed in one well of a 12-well plate. At the same time, 2 ug of tumor cell-derived EVs were added. Then the plate was centrifuged at 300 g for 1 min to initiated cell-cell contact. Cells were incubated at regular cell culture conditions for 24 h before further analyses.

The Jurkat-Raji cells conjugation system was used for understanding the impacts of human tumor organoid-derived EVs on co-stimulation as well. 0.1 million antigen-loaded Raji B cells and 0.1 Jurkat T-cells were mixed and loaded to one insert of a 12 well transwell co-culture system (Costar, 3.0 μm). $10^5$ human CRC organoids cells were seeded on the bottom of the transwell co-culture system to produce tumor-derived EVs. To block the EVs production, 30 μM GW4869 was added to the co-culture assay. Concentration of IL-2 was quantified in the co-culture system.

Western Blotting

Cells were incubated in low oxygen (1%) condition for 24 h to induce hypoxia. For western blotting, total cellular protein (30 μg) from each sample was separated by SDS-PAGE, transferred to PVDF membranes and subjected to primary antibody incubation. Antibodies for Western blot analysis include anti-HIF-1α (Abcam), anti-Rab27a (Abcam), and anti-Beta-Actin (Cell Signaling Technology). All primary antibodies were incubated at 4° C. overnight. Peroxidase-linked anti-mouse IgG and peroxidase-linked anti-rabbit IgG were used as secondary antibodies. All secondary antibodies were incubated for 1 h at room temperature. Pierce ECL western blotting substrate (Thermo Scientific) was used for image development.

Tissue Digestion and Flow/Mass Cytometry

Mouse and human fresh tumor tissues were cut into small pieces (2 mm*2 mm) and digested by collagenase I and IV (0.5 mg/ml for each) and deoxyribonuclease (50 units/ml) for 1 h at 37° C. Digested tissues were loaded on a cell strainer with 70 μm holes. Then the tissues were fully meshed and flushed through the cell strainer into a 50 ml conical tube. Red blood cells (RBC) were removed by RBC lysis buffer and the remaining cells were counted for further steps. For flow cytometry, diluted Zombie fixable viability dye (Biolegend) was used to differentiate live and dead cells. Cells were then stained with antibody cocktails for cell surface markers. Cells were subjected to cytoplasm staining or intranuclear staining after cell surface staining when needed. The Cyto-Fast Fix-Perm Buffer Set (BioLegend) and True-Nuclear Transcription Factor Buffer Set (BioLegend) were used. We followed the manufactures' instructions for all steps. To avoid signal decay, we analyzed all samples right after the staining steps. For lymphatic tissue staining, the enzyme digestion was omitted and 40 μm cell strainer was used to replace the 70 μm cell strainer used for tumor tissues.

We performed mass cytometry to measure the tumor immune landscape after immunotherapies. Details on antibodies and reagents used are listed in Table 1. Metal pre-labeled antibodies were purchased from Fluidigm Corporation and unlabeled antibodies were purchased (MaxPar® Ready purified) from Biolegend. We performed antibody-metal tag conjugation by using the MaxPar X8 antibody labeling kit (Fluidigm Corporation) according to the manufacturer's instructions. All manually labeled antibodies were validated and titrated in positive control and negative control samples.

Single cells were isolated from mouse tumor tissues and used for mass cytometry staining. We followed the public protocol from Fluidigm Corporation for detail procedures. After antibody staining, EQ Four Element Calibration Beads with the reference EQ passport P13H2302 were added to each staining tube right before data acquisition by a CyTOF 2 mass cytometer. The mass cytometry data were normalized cross all cases before analysis. A t-SNE analysis was performed on all alive cells in tumor samples.

DNA, mRNA and miRNA Analyses

For all DNA analyses, DNA was extracted with a DNA Extraction kit from Qiagen. The size of DNA sequences was analyzed by electrophoresis. Total RNA extraction from tissues, cells, and EVs, was performed with a mirVana Total RNA Isolation kit (Life Technologies). Extractions were carried out according to the manufacturer's instructions. 500 ng of total RNA was used for establishing the cDNA library with the miScript II RT Kit (Qiagen). qRT-PCR was performed with SYBR Green I Master kit (Roche Applied Science) in a LightCycler 480. miRNA sequence specific forward primer and universal reverse primers were used for mature miRNA analysis. U6 small nuclear RNA was used as internal controls.

The total RNA isolated by the mirVana Total RNA Isolation kit (Life Technologies) was also used for high throughput mRNA and miRNA expression quantification.

Statistical Analysis

All other statistical analyses were carried out using GraphPad Prism v.6.0. Normality of distribution was determined by D'Agostino-Pearson omnibus normality test. Levene's Test was used for assessing the equality of variances. For normally distributed data with homogeneity of variance, significance of mean differences was determined using two-tailed unpaired or paired Student's t-tests. Non-parametric Mann-Whitney U-tests or Wilcoxon matched-pairs tests were used for unpaired and paired analysis of non-normally distributed data, respectively. One-way ANOVA was used when more than two groups for comparisons were needed. Lifespan curves were plotted with the Kaplan-Meier method and P values were obtained using a log-rank (Mantel-Cox) test. Error bars shown in graphical data represent Mean±SEM. A two-tailed value of $P<0.05$ was considered statistically significant.

TABLE 1

Key materials

| REAGENT or RESCOURCE | SOURCE | IDENTIFIER |
|---|---|---|
| Anti-human/mouse CD3 | Abcam | Cat #: ab11089 |
| Anti-human CD28 | Biorbyt | Cat #: orb10295 |
| Anti-human CD80 | Abcam | Cat #: ab86473 |
| Anti-human CD86 | Abcam | Cat #: ab53004 |
| Anti-human E-cadherin | Abcam | Cat #: ab76055 |
| Anti-human CD11c | Abcam | Cat #: ab52632 |
| Anti-human CD11c | Abcam | Cat #: ab212508 |
| Anti-mouse Ki-67 | Abcam | Cat #: ab15580 |
| Anti-mouse Cleaved-caspase 3 | R&D systems | Cat #: AF835 |
| Anti-human CD8 | Abcam | Cat #: ab17147 |
| Goat anti-Rabbit Secondary Antibody, Alexa Fluor 488 | Invitrogen | Cat #: A11008 |
| Goat anti-Mouse Secondary Antibody, Alexa Fluor 488 | Invitrogen | Cat #: A11001 |
| Goat anti-Rabbit Secondary Antibody, Alexa Fluor 568 | Invitrogen | Cat #: A11011 |
| Goat anti-Rat Secondary Antibody, Alexa Fluor 568 | Invitrogen | Cat #: A11077 |
| Donkey anti-Rat Secondary Antibody, Alexa Fluor 488 | Invitrogen | Cat #: A21208 |

TABLE 1-continued

| Key materials | | |
|---|---|---|
| REAGENT or RESCOURCE | SOURCE | IDENTIFIER |
| Goat anti-Mouse Secondary Antibody, Alexa Fluor 568 | Invitrogen | Cat #: A11004 |
| Anti-human CD63-FITC (H5C6) | BioLegend | Cat #: 353006 |
| Anti-human CD9-FITC (HI9a) | BioLegend | Cat #: 312104 |
| Anti-mouse CD63-PE (NVG-2) | BioLegend | Cat #: 143904 |
| Anti-mouse CD9-FITC (MZ3) | BioLegend | Cat #: 124808 |
| Anti-human HLA-DR-PE (L243) | BioLegend | Cat #: 307606 |
| Anti-human CD14-Pacific Blue (63D3) | BioLegend | Cat #: 367122 |
| Anti-human CD1a-FITC (HI149) | BioLegend | Cat #: 300104 |
| Anti-human CD80-BV 510 (2D10) | BioLegend | Cat #: 305234 |
| Anti-human CD45-APC/Cy7 (HI30) | BioLegend | Cat #: 304014 |
| Anti-human CD56-Pacific Blue (5.1H11) | BioLegend | Cat #: 362519 |
| Anti-human CD45-Pacific Blue (2D1) | BioLegend | Cat #: 368539 |
| Anti-human CD19-Pacific Blue (HIB19) | BioLegend | Cat #: 302224 |
| Anti-human CD8a-APC/Cy7 (HIT8a) | BioLegend | Cat #: 300926 |
| Anti-human CD3-PE/Cy7 (HIT3a) | BioLegend | Cat #: 300316 |
| Anti-human CD4-PE (A161A1) | BioLegend | Cat #: 357404 |
| Anti-human CD28-PerCP/Cy5.5 (CD28.2) | BioLegend | Cat #: 302922 |
| Anti-human CD11b-PE/Cy5 (ICRF44) | BioLegend | Cat #: 301308 |
| Anti-human CD3-Pacific Blue (UCHT1) | BioLegend | Cat #: 300417 |
| Anti-human CD86-PE/Cy7 (IT2.2) | BioLegend | Cat #: 305422 |
| Anti-human CD11c-APC (3.9) | BioLegend | Cat #: 301614 |
| Anti-mouse/human FOXP3-PE (150D) | BioLegend | Cat #: 320008 |
| Anti-mouse CD25-APC (PC61) | BioLegend | Cat #: 102012 |
| Anti-mouse Ki-67-Pacific Blue (16A8) | BioLegend | Cat #: 652422 |
| Anti-mouse CD3-FITC (17A2) | BioLegend | Cat #: 100204 |
| Anti-mouse CD28-PE (37.51) | BioLegend | Cat #: 102106 |
| Anti-mouse PD-1-PerCP/Cy5.5 (29F.1A12) | BioLegend | Cat #: 135208 |
| Anti-mouse CD62L-PE/Cy7 (MEL-14) | BioLegend | Cat #: 104418 |
| Anti-mouse CD8a-APC/Cy7 (53-6.7) | BioLegend | Cat #: 100714 |
| Anti-mouse LAG-3-BV421 (C9B7W) | BioLegend | Cat #: 125221 |
| Anti-mouse/human CD44-PE (IM7) | BioLegend | Cat #: 103008 |
| Anti-mouse CD19-Pacific Blue (6D5) | BioLegend | Cat #: 115523 |
| Anti-mouse CD4-BV510 (GK1.5) | BioLegend | Cat #: 100449 |
| Anti-mouse CD86-PE (GL-1) | BioLegend | Cat #: 105007 |
| Anti-mouse F4/80-PE/Cy5 (BM8) | BioLegend | Cat #: 123111 |
| Anti-mouse CD80-PE/Cy7 (16-10A1) | BioLegend | Cat #: 104734 |
| Anti-mouse/human CD11b-APC (M1/70) | BioLegend | Cat #: 101212 |
| Anti-mouse I-A/I-E-APC/Cy7 (M5/114.15.2) | BioLegend | Cat #: 107628 |
| Anti-mouse CD11c-BV510 (N418) | BioLegend | Cat #: 117338 |
| Anti-mouse CD45-Pacific Blue (30-F11) | BioLegend | Cat #: 103126 |
| Anti-mouse CD45-FITC (30-F11) | BioLegend | Cat #: 103108 |
| Anti-mouse CD3-PerCP/Cy5.5 (17A2) | BioLegend | Cat #: 100218 |

TABLE 1-continued

| Key materials | | |
|---|---|---|
| REAGENT or RESCOURCE | SOURCE | IDENTIFIER |
| Anti-mouse CD3ε-PE/Cy7 (145-2C11) | BioLegend | Cat #: 100320 |
| Anti-mouse CD103-Pacific Blue (2E7) | BioLegend | Cat #: 121418 |
| Anti-mouse Gr-1-PE/Cy7 (RB6-8C5) | BioLegend | Cat #: 108416 |
| Anti-mouse CD45-BV510 (30-F11) | BioLegend | Cat #: 103138 |
| Anti-mouse Podoplanin-APC/Cy7(8.1.1) | BioLegend | Cat #: 127418 |
| Anti-mouse CD31-Pacific Blue (390) | BioLegend | Cat #: 102422 |
| Rat IgG1, κ Isotype Ctrl-Pacific Blue (RTK2071) | BioLegend | Cat #: 400419 |
| Rat IgG1, κ Isotype Ctrl-PE/Cy7 (RTK2071) | BioLegend | Cat #: 400415 |
| Mouse IgG1, κ Isotype Ctrl-PE/Cy7 (MOPC-21) | BioLegend | Cat #: 400125 |
| Mouse IgG1, κ Isotype Ctrl-PE (MOPC-21) | BioLegend | Cat #: 400111 |
| Mouse IgG1, κ Isotype Ctrl-BV510 (MOPC-21) | BioLegend | Cat #: 400171 |
| Mouse IgG1, κ Isotype Ctrl-PerCP/Cy5.5 (MOPC-21) | BioLegend | Cat #: 400149 |
| Rat IgG2a, κ Isotype Ctrl-PerCP/Cy5.5 (RTK2758) | BioLegend | Cat #: 400531 |
| Anti-mouse CD45-89Y (30-F11) | Fluidigm | Cat #: 3089005B |
| Anti-mouse Ly-6G-41Pr (1A8) | Fluidigm | Cat #: 3141008B |
| Anti-mouse CD11c-142Nd (N418) | Fluidigm | Cat #: 3142003B |
| Anti-mouse CD4-145Nd (RM4-5) | Fluidigm | Cat #: 3145002B |
| Anti-mouse F4/80-146Nd (BM8) | Fluidigm | Cat #: 3146008B |
| Anti-mouse Gr-1-147Sm (RB6-8C5) | BioLegend/ Fluidigm | Cat #: 108449/201147B |
| Anti-mouse CD11b-148Nd (M1/70) | Fluidigm | Cat #: 3148003B |
| Anti-mouse CD19-149Sm (6D5) | Fluidigm | Cat #: 3149002B |
| Anti-mouse CD25-150Nd (3C7) | Fluidigm | Cat #: 3150002B |
| Anti-mouse CD28-151Eu (37.51) | Fluidigm | Cat #: 3151005B |
| Anti-mouse CD3e-152Sm (145-2C11) | Fluidigm | Cat #: 3152004B |
| Anti-mouse CD274-153Eu (10F.9G2) | Fluidigm | Cat #: 3153016B |
| Anti-mouse CD152-154Sm (UC10-4B9) | Fluidigm | Cat #: 3154008B |
| Anti-mouse CD279-155Gd (RMP1-30) | BioLegend/ Fluidigm | Cat #: 109113/201155A |
| Anti-mouse CD335-156Gd (29A1.4) | BioLegend/ Fluidigm | Cat #: 137625/201156B |
| Anti-mouse Foxp3-158Gd (FJK-16s) | Fluidigm | Cat #: 3158003A |
| Anti-mouse RORgt-B2D-159Tb (B2D) | Fluidigm | Cat #: 3159019B |
| Anti-mouse CD62L-160Gd (MEL-14) | Fluidigm | Cat #: 3160008B |
| Anti-mouse Ki-67-161Dy (B56) | Fluidigm | Cat #: 3161007B |
| Anti-mouse Ly-6C-162Dy (HK1.4) | Fluidigm | Cat #: 3162014B |
| Anti-mouse CD197-164Dy (4B12) | Fluidigm | Cat #: 3164013A |
| Anti-mouse IFNg-165Ho (XMG1.2) | Fluidigm | Cat #: 3165003B |
| Anti-mouse IL-4-166Er (11B11) | Fluidigm | Cat #: 3166003B |
| Anti-mouse CD103-167Er (2E7) | BioLegend/ Fluidigm | Cat #: 121402/ 201167B |
| Anti-mouse CD8a-168Er (53-6.7) | Fluidigm | Cat #: 3168003B |

TABLE 1-continued

| Key materials | | |
|---|---|---|
| REAGENT or RESCOURCE | SOURCE | IDENTIFIER |
| Anti-mouse CD49b-170Er (HMa2) | Fluidigm | Cat #: 3170008B |
| Anti-mouse CD80-171Yb (16-10A1) | Fluidigm | Cat #: 3171008B |
| Anti-mouse CD86-172Yb (GL1) | Fluidigm | Cat #: 3172016B |
| Anti-mouse Granzyme B-173Yb (GB11) | Fluidigm | Cat #: 3173006B |
| Anti-mouse CD127-174Yb (A7R34) | Fluidigm | Cat #: 3174013B |
| Anti-mouse CD44-176Yb (IM7) | BioLegend/ Fluidigm | Cat #: 103051/201176B |
| Anti-mouse I-A/I-E-209Bi (M5/114.15.2) | Fluidigm | Cat #: 3209006B |
| Cell-ID ™ Intercalator-Ir | Fluidigm | Cat #: 201192B |
| Cell-ID ™ Cisplatin | Fluidigm | Cat #: 201064 |
| H-2Ld MuL V gp70 Tetramer-APC | MBL International | Cat #: TB-M521-2 |
| IFN gamma Mouse ELISA Kit | Thermo Fisher Scientific | Cat #: BMS606 |
| Zombie Violet ™ Fixable Viability Kit | BioLegend | Cat #: 423113 |
| Zombie Aqua ™ Fixable Viability Kit | BioLegend | Cat #: 423101 |
| Zombie Green ™ Fixable Viability Kit | BioLegend | Cat #: 423111 |
| Cyto-Fast ™ Fix/Perm Buffer Set | BioLegend | Cat #: 426803 |
| True-Nuclear ™ Transcription Factor Buffer Set | BioLegend | Cat #: 424401 |
| IL-2 Mouse ELISA Kit | Invitrogen | Cat #: 88-7024-22 |
| Mouse Fibrin Degradation Product D-Dimer ELISA Kit | LSBio | Cat #: LS-F6179 |
| Proteome Profiler Mouse Cytokine Array Kit, Panel A | R&D systems | Cat #: ARY006 |
| Dynabeads ™ Untouched ™ Human T Cells Kit | Invitrogen | Cat #: 11344D |
| Dynabeads ™ Untouched ™ Mouse T Cells Kit | Invitrogen | Cat #: 11413D |
| Dynabeads ™ Human T-Activator CD3/CD28 for T Cell Expansion and Activation | Invitrogen | Cat #: 11161D |
| Dynabeads ™ Mouse T-Activator CD3/CD28 for T-Cell Expansion and Activation | Invitrogen | Cat #: 11452D |
| SEE highly purified STA 100UG | Toxin Technologies Inc | Cat #: ET404100UG |
| Mouse: BALB/cJ | The Jackson Laboratory | Stock No: 000651 |
| Mouse: B6.129S2-Cd28$^{tm1Mak}$/J | The Jackson Laboratory | Stock No: 002666 |
| Mouse: B6.129S4-Cd80$^{tm1Shr}$ Cd86$^{tm2Shr}$/J | The Jackson Laboratory | Stock No: 003610 |
| Mouse: NOD.CB17-Prkdc$^{scid}$/J | The Jackson Laboratory | Stock No: 001303 |
| Mouse: B6.CB17-Prkdc$^{scid}$/SzJ | The Jackson Laboratory | Stock No: 001913 |
| Mouse: B6(Cg)-Tlr$^{4tm1.2Karp}$/T | The Jackson Laboratory | Stock No: 029015 |
| Mouse: C57BL/6 | The Charles River Laboratories | Stock No: 027 |
| InVivoMAb anti-mouse CD80 | Bio X Cell | Cat #: BE0024 |
| InVivoMAb anti-mouse CD86 | Bio X Cell | Cat #: BE0025 |
| InVivoPlus anti-mouse PD-1 | Bio X Cell | Cat #: BP0146 |
| InVivoPlus anti-mouse CTLA-4 | Bio X Cell | Cat #: BP0032 |
| InVivoPlus rat IgG2a isotype control | Bio X Cell | Cat #: BP0089 |
| InVivoPlus polyclonal Armenian hamster IgG | Bio X Cell | Cat #: BP0091 |
| D-Luciferin, Potassium Salt | GOLDBIO | Cat #: LUCK-1G |
| Matrigel ™ Membrane Matrix | Corning | Cat #: 354234 |
| psiCHECKTM-2 Vectors | Promega | Cat #: C8021 |
| pPACKH1-XL packaging mix | SBI | Cat #: LV510A-1 |

TABLE 1-continued

| Key materials | | |
|---|---|---|
| REAGENT or RESCOURCE | SOURCE | IDENTIFIER |
| Lipofectamine ™ 3000 Transfection Reagent | Invitrogen | Cat #: L3000001 |
| mirVana ™ miRNA Isolation Kit | Invitrogen | Cat #: AM1560 |
| mirVana Total RNA Isolation Kit | Life Technologies | Cat #: A27828 |
| miScript II RT Kit | Qiagen | Cat #: 218161 |
| LightCycler ® 480 SYBR Green I Master | Roche | Cat #: 04707516001 |
| PureLink ™ Genomic DNA Mini Kit | Invitrogen | Cat #: K182001 |
| Phusion ® High-Fidelity DNA Polymerase | New England Biolabs | Cat #: M0530S |
| Q5 ® Site-Directed Mutagenesis Kit | New England Biolabs | Cat #: E0554S |
| PRIMERS/GUIDE RNA | SEQUENCE (5'-3') | IDENTIFIER |
| hsa-miR-424-5p | CAGCAGCAATT CATGTTTTGAA (SEQ ID NO:19) | NA |
| mmu-miR-322-5p | CAGCAGCAATT CATGTTTTGGA (SEQ ID NO: 20) | NA |
| U6 snRNA | AAGGATGACAC GCAAATTCG3 (SEQ ID NO: 21) | NA |
| In situ hybridization Kit | BioChain | Cat #: K2191020 |
| Nuclear Fast Red ™ | Sigma Aldrich | Cat #: N3020 |
| Eukitt ® Quick-hardening mounting medium | Sigma Aldrich | Cat #: 03989 |
| SCRAMBLE-MIR MIRCURY LNA Probe | Qiagen | Cat #: YD00699004-BCG |
| U6, HSA/MMU/RNO MIRCURY LNA Probe | Qiagen | Cat #: YD00699002-BCG |
| HSA-MIR-424-5P MIRCURY LNA Probe | Qiagen | Cat #: YD00619854-BCG |
| H&E Staining Kit | Abcam | Cat #: ab245880 |
| ProLong ™ Gold Antifade Mountant | Invitrogen | Cat #: P36934 |
| AR6 Buffer | PerkinElmer | Cat #: AR600250ML |
| AR9 Buffer | PerkinElmer | Cat #: AR900250ML |
| Advanced DMEM F/12 | Thermo Fisher Scientific | Cat #: 12634-010 |
| Glutamax | Life Technologies | Cat #: 35050-061 |
| N-Acetylcysteine | Sigma Aldrich | Cat #: A9165-SG |
| Growth factor reduced Matrigel | BD | Cat #: 354230 |
| Y-27632 (Rho Kinase inhibitor) | EMD Millipore | Cat #: 688001 |
| EGF | Invitrogen | Cat #: PMG8043 |
| L-WRN cells | ATCC | Cat #: CRL-3276 |
| SB202190 | Sigma Aldrich | Cat #: S7067 |
| B27 supplement | Invitrogen | Cat #: 17504-044 |
| N2 Supplement | Invitrogen | Cat #: 17502-048 |
| TrypLE Express | Invitrogen | Cat #: 12605-036 |
| Primocin | Invivogen | Cat #: ant-pm-1 |
| Gastrin | Sigma Aldrich | Cat #: G9145 |
| Nicotinamide | Sigma Aldrich | Cat #: N0636 |
| A-83-01 | Tocris | Cat #: 2939 |
| Prostaglandin E2 | Cayman Chemicals | Cat #: 14010-1 |

Example 2: Chemotherapy but not the Tumor Draining Lymph Nodes Determine the Immunotherapy Response in Secondary Tumors Immunotherapies are used as adjuvant therapies for cancers. However, knowledge of how traditional cancer treatments affect immunotherapies is limited. In the following Example, the inventors use mouse models to demonstrate that tumor-draining lymph nodes (TdLNs) are critical for tumor antigen-specific T-cell response. However, they found that removing TdLNs concurrently with established primary tumors did not affect the immune checkpoint blockade (ICB) response on localized secondary tumor due to immunotolerance in TdLNs and distribution of antigen-specific T cells in peripheral lymphatic organs. Notably, treatment response improved with sequential administration of 5-fluorouracil (5-FU) and ICB compared to concurrent administration of ICB with 5-FU. Immune profiling revealed that using 5-FU as induction treatment increased tumor visibility to immune cells, decreased immunosuppressive cells in the tumor microenvironment, and limited chemotherapy-induced T-cell depletion. The inventors show that the effect of traditional cytotoxic treatment, not TdLNs, influences immunotherapy response in localized secondary tumors, and postulate essential considerations for successful immunotherapy strategies in clinical conditions.

Introduction:

Immune checkpoint blockade therapies (ICBT) such as anti-CTLA-4 and anti-PD-1/PD-L1, have transformed the therapeutic landscape of cancers, including melanoma and tumors with microsatellite instability (Le et al., 2017; Robert et al., 2011; Topalian et al., 2012).

Nonetheless, as with more traditional forms of systemic chemotherapy options, many patients manifest either intrinsic or acquired resistance leading to treatment failure (Gide et al., 2018; Sharma et al., 2017; Zhao and Subramanian, 2017). Multiple mechanisms that influence tumor response to ICBTs have been identified—the mutational load in tumor cells, degree of T-cell exhaustion, tumor microenvironmental functions, and intestinal microbiota (Gide et al., 2018; Sharma et al., 2017; Zhao and Subramanian, 2017). In most cases, ICBT is used for treating patients with heavily pretreated tumors. The interactions between first-line therapy may influence tumor response to subsequently administered ICBTs due to tumor evolution and heterogeneity. In most patients with solid tumors, common interventions before ICBT include resection of primary tumors with concurrent resection of draining lymph nodes followed by administration of chemotherapies and/or targeted therapies (Le et al., 2017; Lee et al., 2017; Rizvi et al., 2015). However, minimal information is known about whether these interventions will impact tumor response to ICBT.

Tumor-draining lymph nodes (TdLNs), which are usually resected concurrently with the primary tumors, have shown dual impacts on tumor development and treatment. On the one hand, TdLNs are critical peripheral lymphatic organs where tumor antigens are presented by dendritic cells to naïve T cells to elicit antitumor immunity (Fisher and Fisher, 1971; Shu et al., 2006; Toki et al., 2020). Thus, loss of TdLNs weakens immunosurveillance mechanisms and increases the likelihood of tumor initiation and progression (Fisher and Fisher, 1971; Karlsson et al., 2010; Shu et al., 2006; Toki et al., 2020). On the other hand, TdLNs are affected by immunosuppressive factors released by tumor cells during tumor progression. These immunosuppressive factors can suppress the function of TdLNs, making them immune-privileged sites (Cochran et al., 2001; Ito et al., 2006; Munn and Mellor, 2006; Murthy et al., 2019; Watanabe et al., 2008). Based on these facts, we hypothesize that TdLN resection is an essential factor which influences long-term tumor immunity and response to ICBT. In this study, we used tumor models representing different disease stages to elucidate the impacts of TdLN resection on ICBT efficacy and understand the underlying mechanisms of those effects.

The immunoregulatory effects of chemotherapies have been investigated in multiple cancer models with different chemotherapy drugs. Chemotherapy drugs such as oxaliplatin, paclitaxel, and 5-fluorouracil (5-FU) have shown positive effects in antitumor immunity either by eliciting a tumor-specific T-cell response or by reducing immunosuppressive factors in the tumor microenvironment (Khosravianfar et al., 2018; Pfirschke et al., 2016; Zhang et al., 2008). Bone marrow suppression, which is a common side effect of chemotherapies, causes leukopenia that affects antitumor immunity. Because chemotherapies have dual effects on regulating antitumor immunity, we hypothesize that combining chemotherapy with ICBT has diverse effects on antitumor immune response and consequently, an appropriate combinatory strategy will be critical in determining tumor response. In this study, we used 5-FU, which blocks DNA replication, as a representative chemotherapeutic drug to study the factors that influence the effects of chemotherapy on ICBT.

Mouse models are critical for pre-clinical cancer studies; most published studies have been performed on primary tumor models. To better represent the clinical conditions in which most immunotherapies are administered, we established a mouse tumor model that allows evaluation of the immunotherapeutic response in secondary tumors after primary tumor resection with or without concurrent TdLN removal. We also included anti-PD-1 (antagonist to inhibitory immune checkpoints) and anti-4-1BB (agonist to stimulatory immune checkpoints) to better represent ICBT with different mechanisms (Buchan et al., 2018; Chester et al., 2016).

Figures 19A, 19B, 19C:
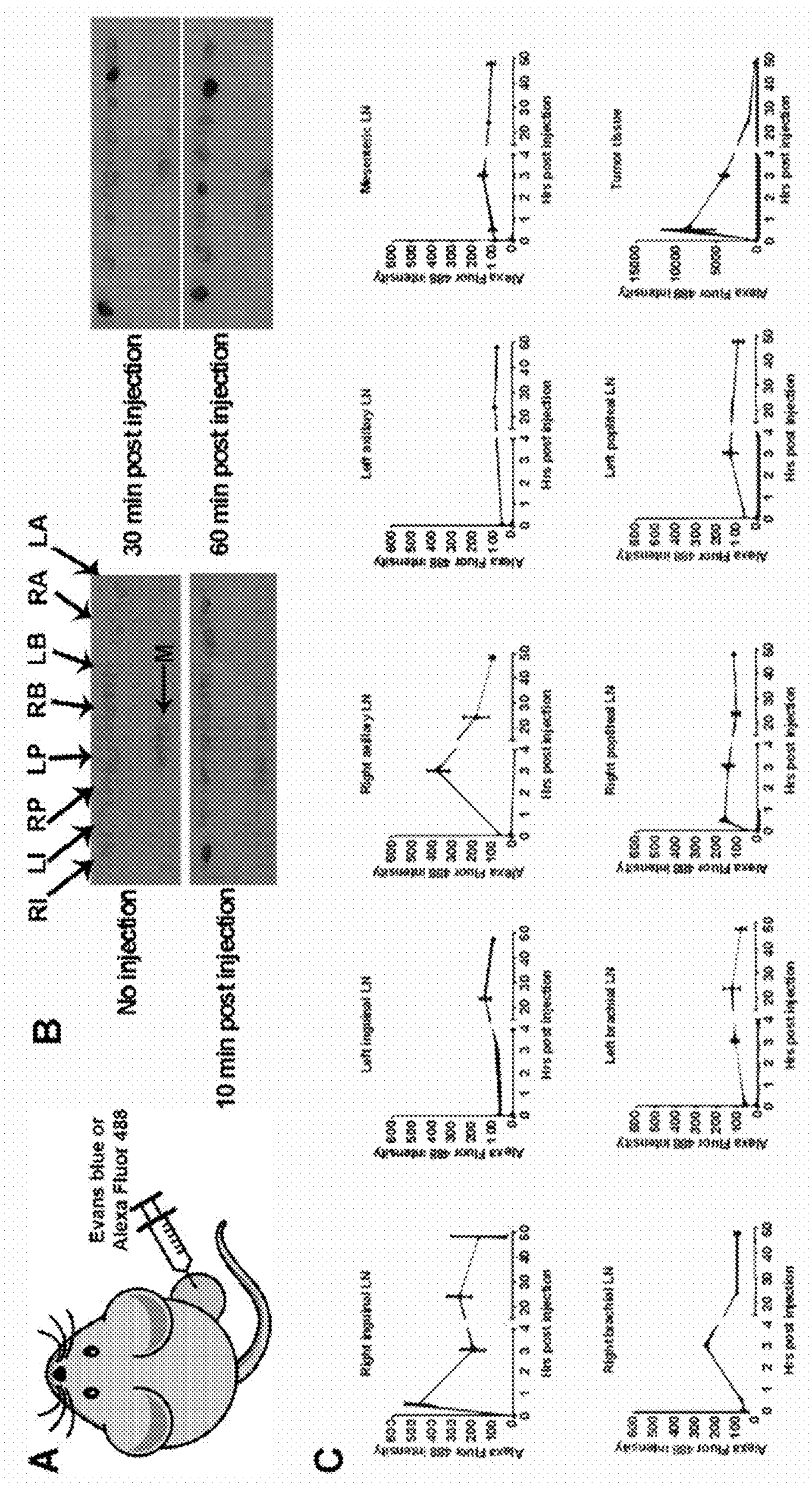
FIGS. 19A-19C depict the identification of tumor-draining lymph nodes (TdLNs) in mouse. Related to FIGS. 13-15.

Results:

TdLNs are Essential for Antitumor Immune Activation and Immunotherapy Response in Early-Stage Disease We first needed to identify TdLNs in the subcutaneous tumor model. We injected Evans blue and Alexa Fluor 488 into tumors established in the right flank of the mice to trace lymphatic drainage (FIG. 19A). Evans blue staining was detected in the right inguinal and axillary lymph nodes 10 min after injection (FIG. 19B). To develop a more sensitive method for detection, we used flow cytometry to trace the Alexa Fluor 488 drainage in lymphatic organs for up to 48 hr. Again, the right inguinal and right axillary lymph nodes showed the highest fluorescence intensity (FIG. 19C). Other lymph nodes, such as right brachial and right popliteal lymph nodes, also showed increased fluorescence signal after injection, but the signal intensity was significantly lower than in the right inguinal and right axillary lymph nodes (FIG. 19C). Also, increased weight was observed in the spleen, and right inguinal and axillary lymph nodes during tumor development, suggesting an immune response occurred in these lymphatic organs (FIG. 20A-J). Collectively, these results indicated that the right inguinal and right axillary lymph nodes are the sentinel TdLNs in our tumor model.

Figures 13A, 13B, 13C:
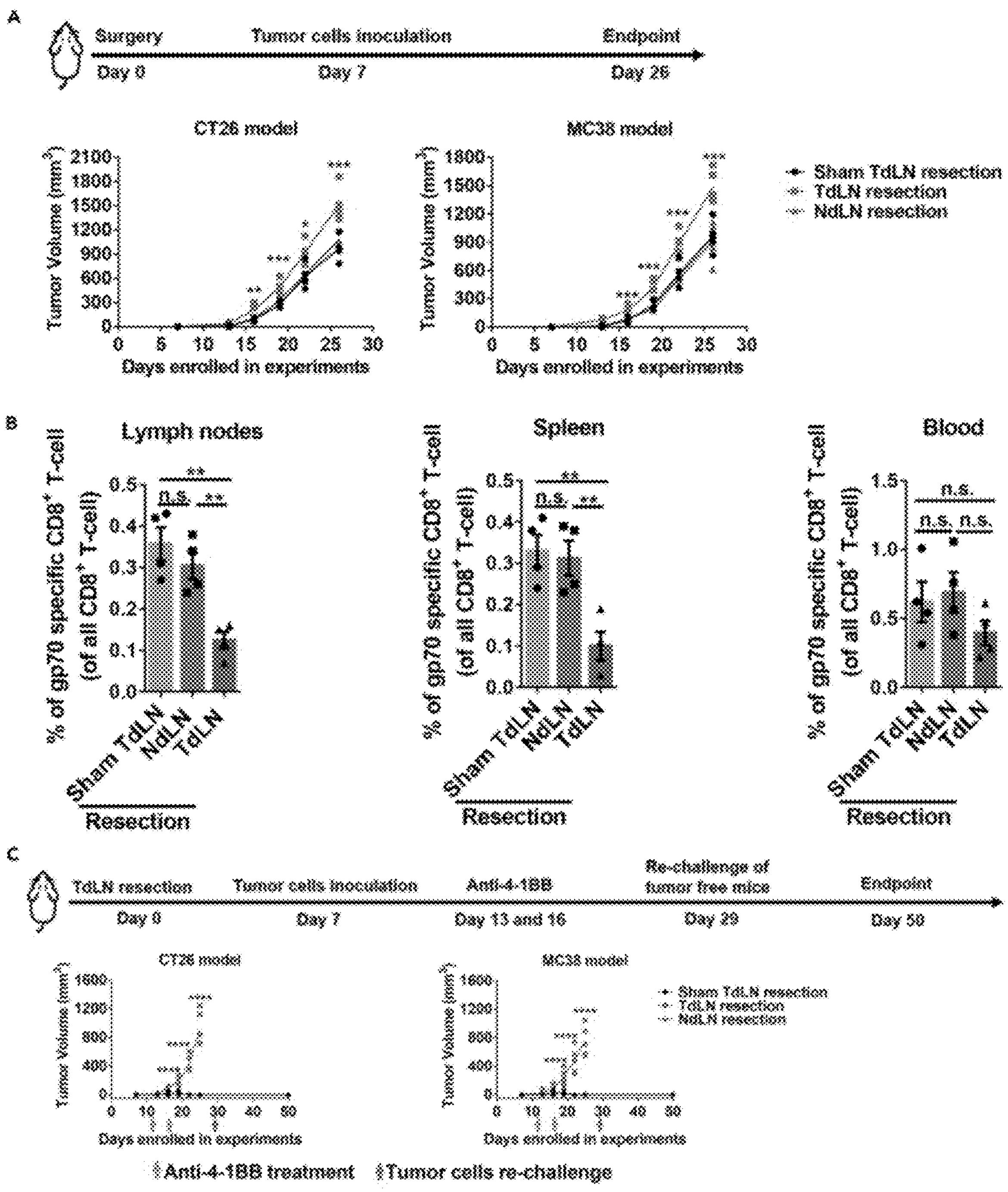
FIGS. 13A-13C show the impact of TdLNs on tumor initiation and immunotherapy response in early-stage tumor models.
Figures 21A, 21B:
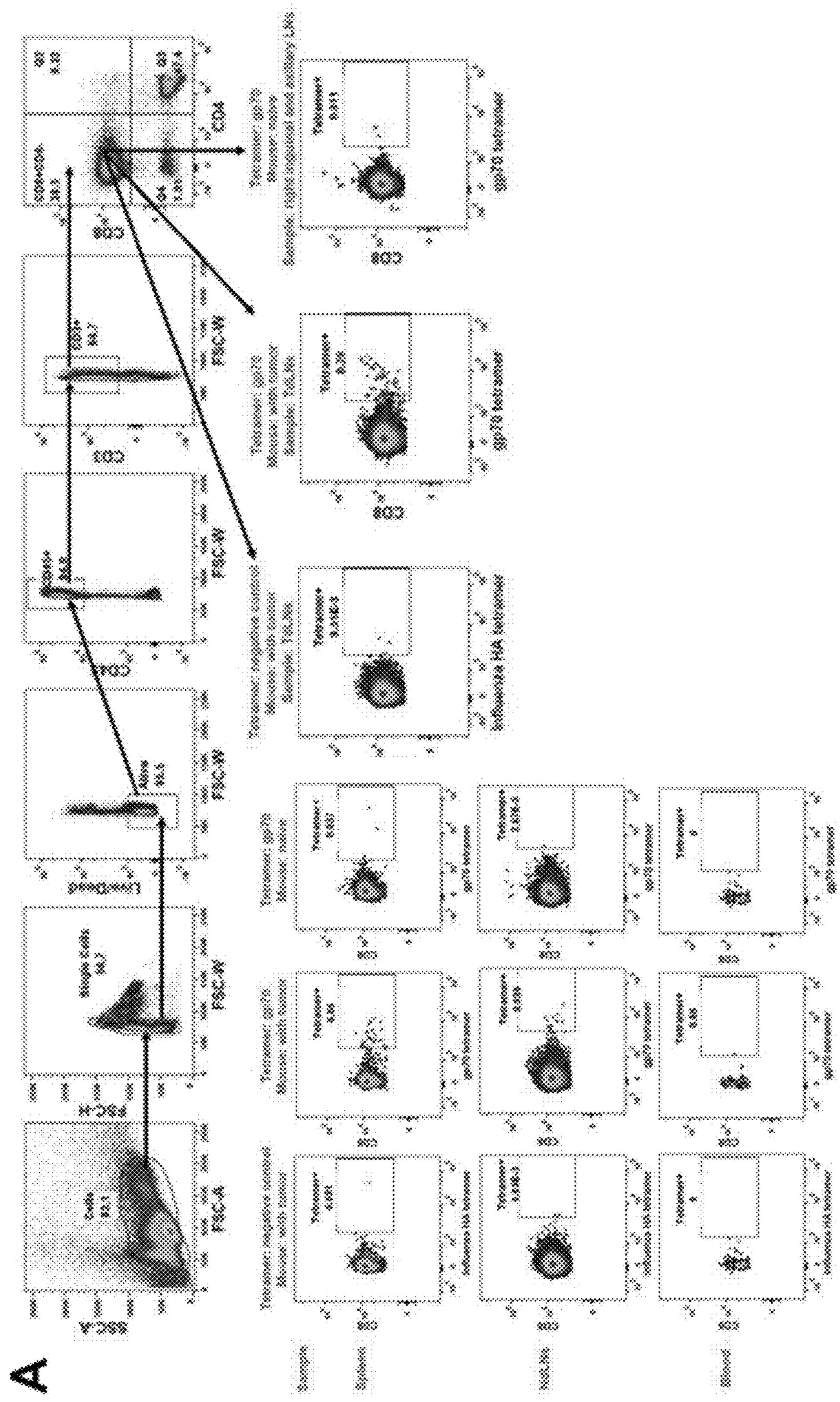
FIGS. 21A-21B show gating of tumor antigen-specific CD8+ T cells. Related to FIGS. 13-15.
Figures 21A, 21B:
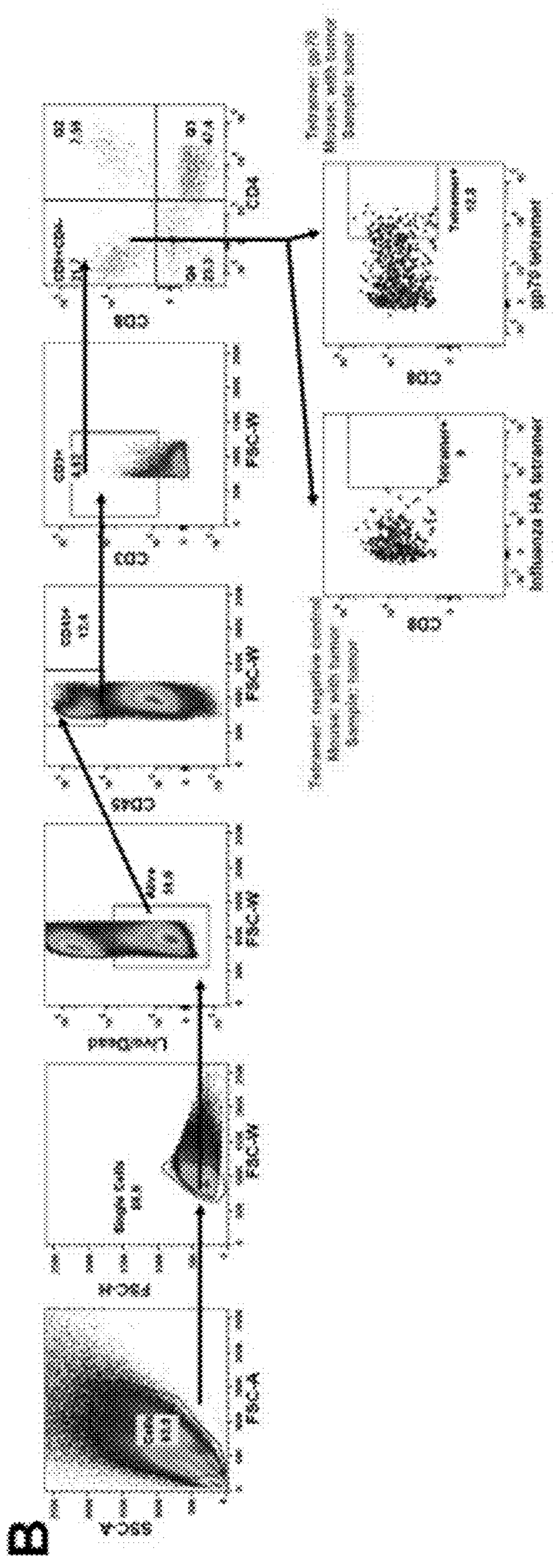

Next, we evaluated the impact of TdLNs on tumor initiation and antitumor immune response stimulation. Resection of TdLNs, but not non-draining lymph nodes (NdLNs), before tumor cell inoculation significantly accelerated tumor development in both CT26 and MC38 tumor models (FIG. 13A). We then analyzed the stimulation of antitumor immunity with and without TdLNs. We used the frequency of tumor antigen-specific $CD8^+$ T cells (10 days after tumor cells inoculation) as an indicator of antitumor immune response stimulation (FIG. 21). More tumor antigen-specific $CD8^+$ T cells were detected in the right and left brachial lymph nodes and spleen of tumor-bearing mice with intact TdLNs (FIG. 13B). 4-1BB (CD137) provides important co-stimulatory signaling for T cells, and its agonist has shown tumor-eliminating effects in mice (Chester et al., 2016). To test the effects of TdLNs on the immunotherapeutic response, we administered two injections of anti-4-1BB shortly after tumor cell inoculation to simulate patients with minimal disease burden. The prophylactic anti-4-1BB treatments successfully prevented tumor development in mice with intact TdLNs, and anti-tumor immunity memory was established as evidenced by their rejection of secondary tumors. These effects were not seen in mice with resected TdLNs (FIG. 13C). These data demonstrated that TdLNs are critical for anti-tumor immunity activation and loss of TdLNs leads to rapid early-stage tumor growth even with the potent T-cell co-stimulatory agonist.

Figures 14A, 14B, 14C:
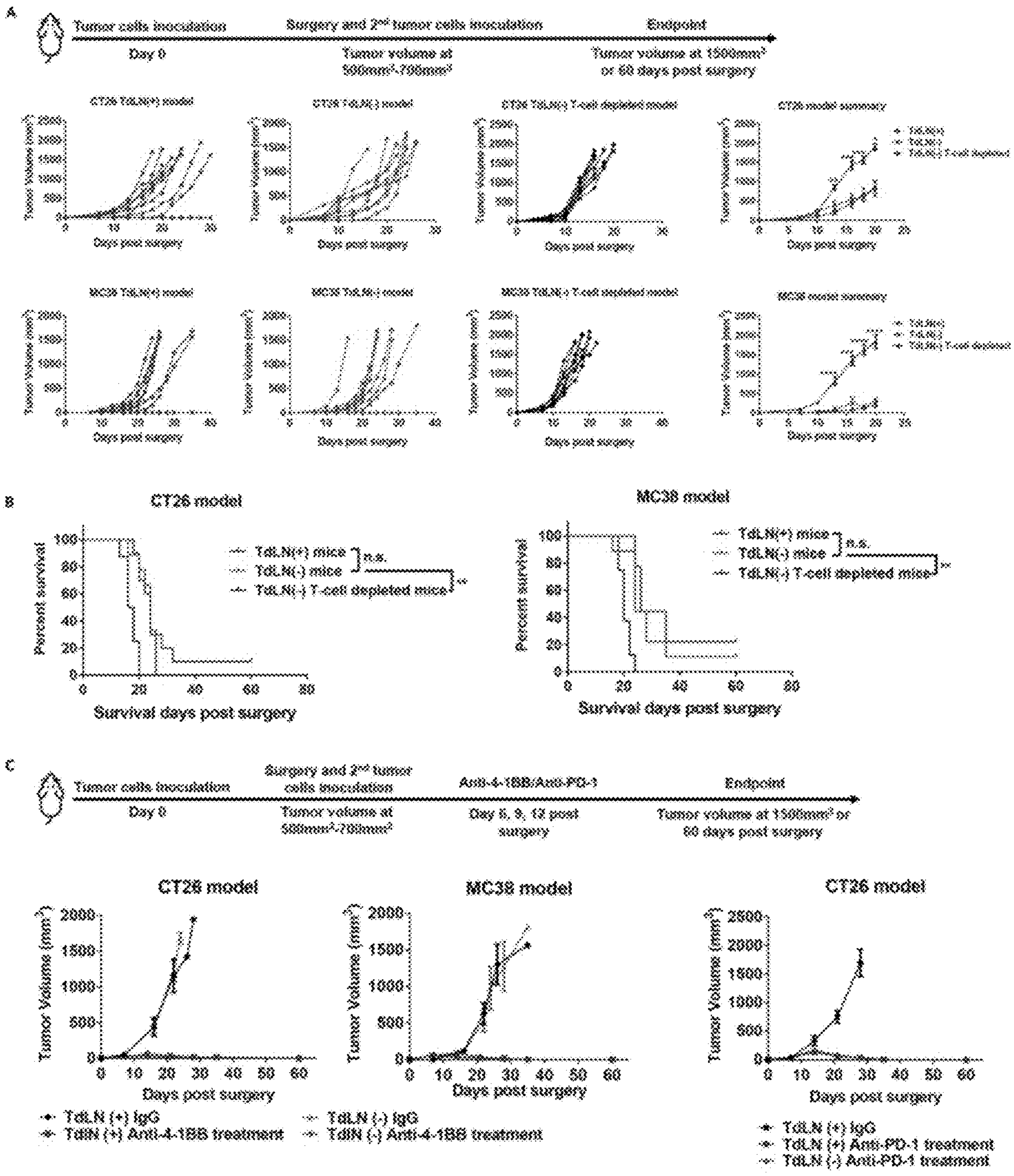
FIGS. 14A-14C show the impact of TdLNs on tumor recurrence and immunotherapy response in advanced stage tumor models.
Figures 20A, 20B, 20C, 20D, 20E, 20F, 20G, 20H, 20I, 20J, 20K:
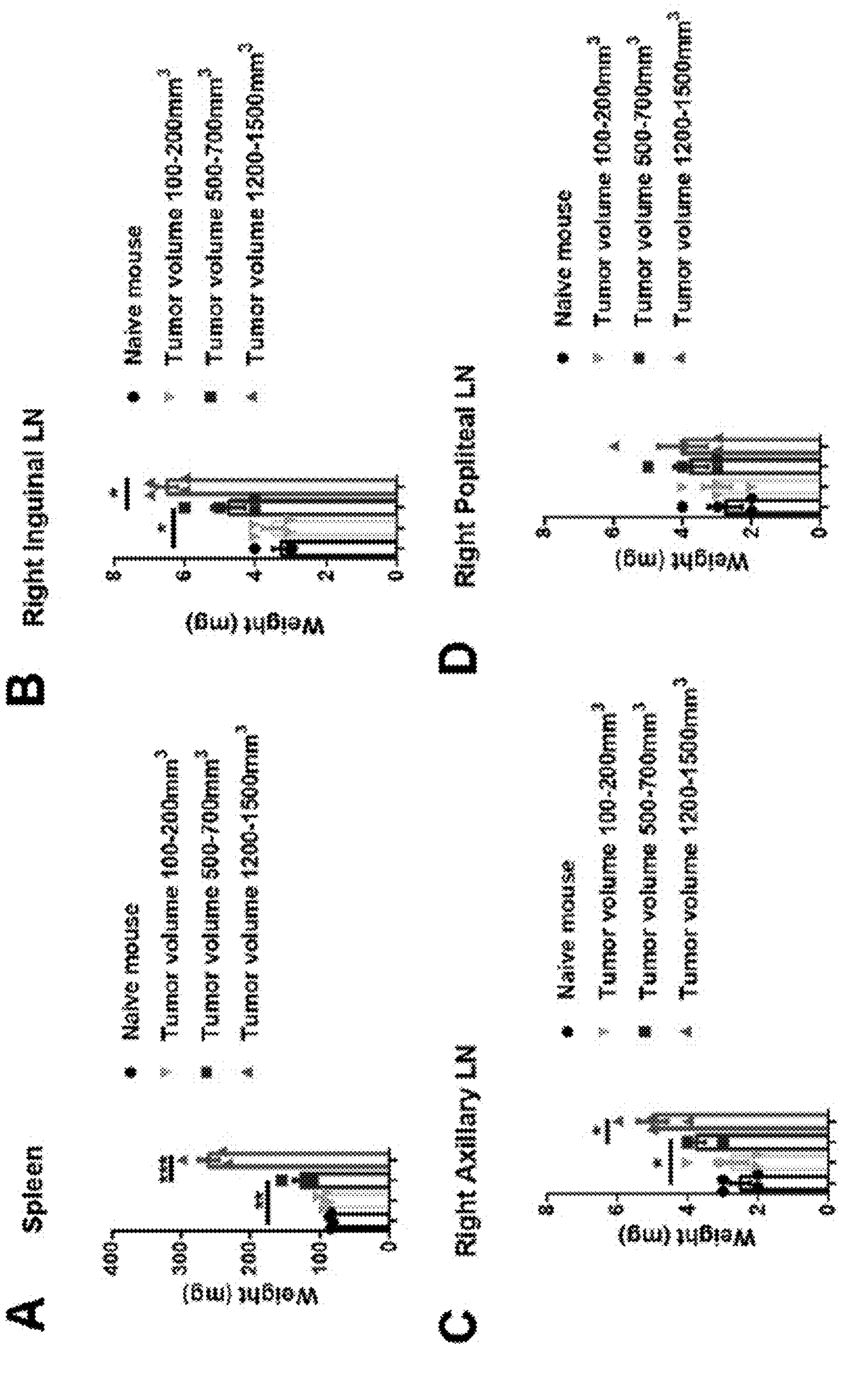
FIGS. 20A-20K show physical changes and histology of TdLNs, NdLNs, and spleen of tumor-bearing mice. Related to FIGS. 13-15.
Figure 20:
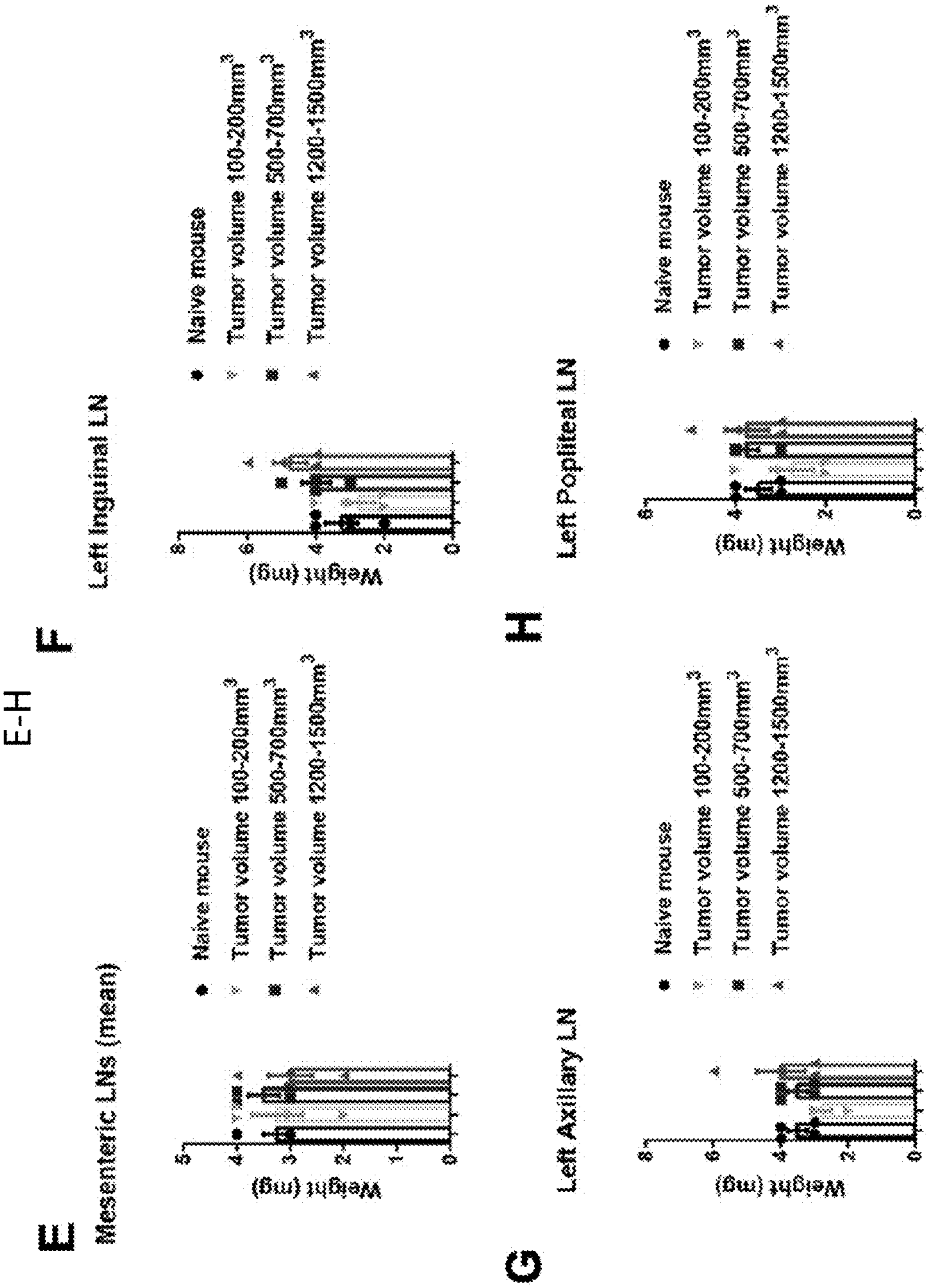

TdLNs are not Necessary for Immunotherapy Response in Advanced Disease Tumor Models Since recurrence after primary tumor resection is one of the major causes for treatment failure, we evaluated the impact of TdLNs on tumor recurrence and the response to immunotherapy in mouse models after advanced primary tumor resection. We allowed the primary tumor to grow to a relatively large volume and then resected the primary tumor with and without concurrent TdLN resection. Secondary tumors were then inoculated to mimic localized tumor recurrence (FIG. 14A). We confirmed a clean primary tumor resection margin in our models (Table 2), allowing all secondary tumors to start with a comparable baseline. TdLNs were also subjected to histological analysis to confirm that no metastasis developed in TdLNs (FIG. 20K). Notably, in our well-controlled model, the secondary tumor growth rate was similar in mice with and without TdLNs FIG. 14A, B). In another group of TdLNs resected mice, we depleted T cells to study the impact of systemic immunity on subsequent tumor development. As predicted, the secondary tumor developed rapidly in mice with impaired systemic immunity (FIG. 14A, B). Together, these results indicate that tumor recurrence is accelerated by impaired systemic immunity but not by impaired regional immunity (TdLNs resection).

TABLE 2 gp70 mRNA expression in different tissues. Related to FIGS. 13-15.

| Model | Tumor tissue | Tuamor marginal skin & connective tissues post-surgery | Normal skin tissue |
|---|---|---|---|
| CT26 (Babl/c) | Positive | Negative | Negative |
| MC38 (C57BL/6) | Positive | Negative | Negative |

Figures 22A, 22B:
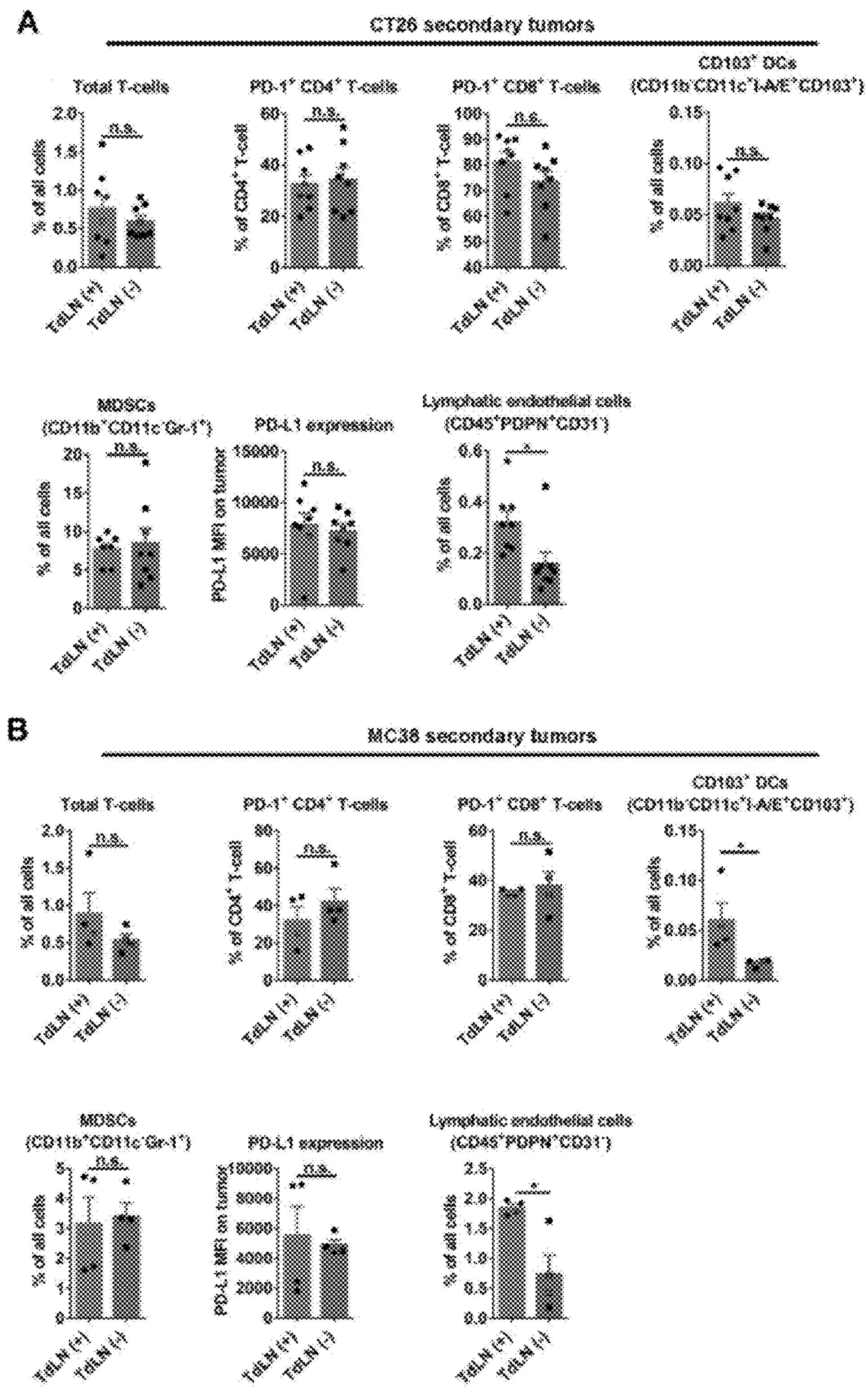
FIGS. 22A-22B show immune features in secondary tumors with or without TdLNs. Related to FIG. 14.

Next, we asked whether TdLNs resection altered immune infiltration in secondary tumors. The major immune cell types were evaluated in secondary tumors (FIG. 22). Total tumor-infiltrating T cells, PD-1 high expression T cells, and MDSCs were not altered in secondary tumors either with or without TdLNs. PD-L1 expression was similar. The frequency of $CD103^+$ DCs and lymphatic endothelial cells were significantly higher in the secondary MC38 tumors with TdLNs (FIG. 22). However, in the CT26 model, only the lymphatic endothelial cell frequency was statistically higher in secondary tumors with TdLNs than without TdLNs. The frequency of $CD103^+$ DCs showed a similar trend but did not reach statistical significance (FIG. 22).

Immunotherapies are typically prescribed to patients who have undergone advanced primary tumor resection. In another pre-clinical model, we administrated anti-4-1BB and anti-PD-1 to study whether TdLN resection will lead to immunotherapy resistance. To mimic clinical conditions, we resected the established primary tumor both with and without concurrent TdLN resection. We then inoculated the secondary tumor to mimic localized tumor recurrence. A 6-day gap was allowed between the secondary tumor inoculation and any treatment (FIG. 14C). This allows the tumor to connect with systemic circulation and to establish the tumor microenvironment. Then, the mice were treated with anti-4-1BB or anti-PD-1 (FIG. 14C). Notably, both anti-4-1BB and anti-PD-1 treatments were efficient in controlling secondary tumor initiation. Secondary tumor control was maintained after TdLN resection (FIG. 14C), suggesting that TdLN resection may not be a major influencing factor on the efficacy of ICBT when used as adjuvant therapy in late-stage disease.

Figures 15A, 15B, 15C, 15D, 15E:
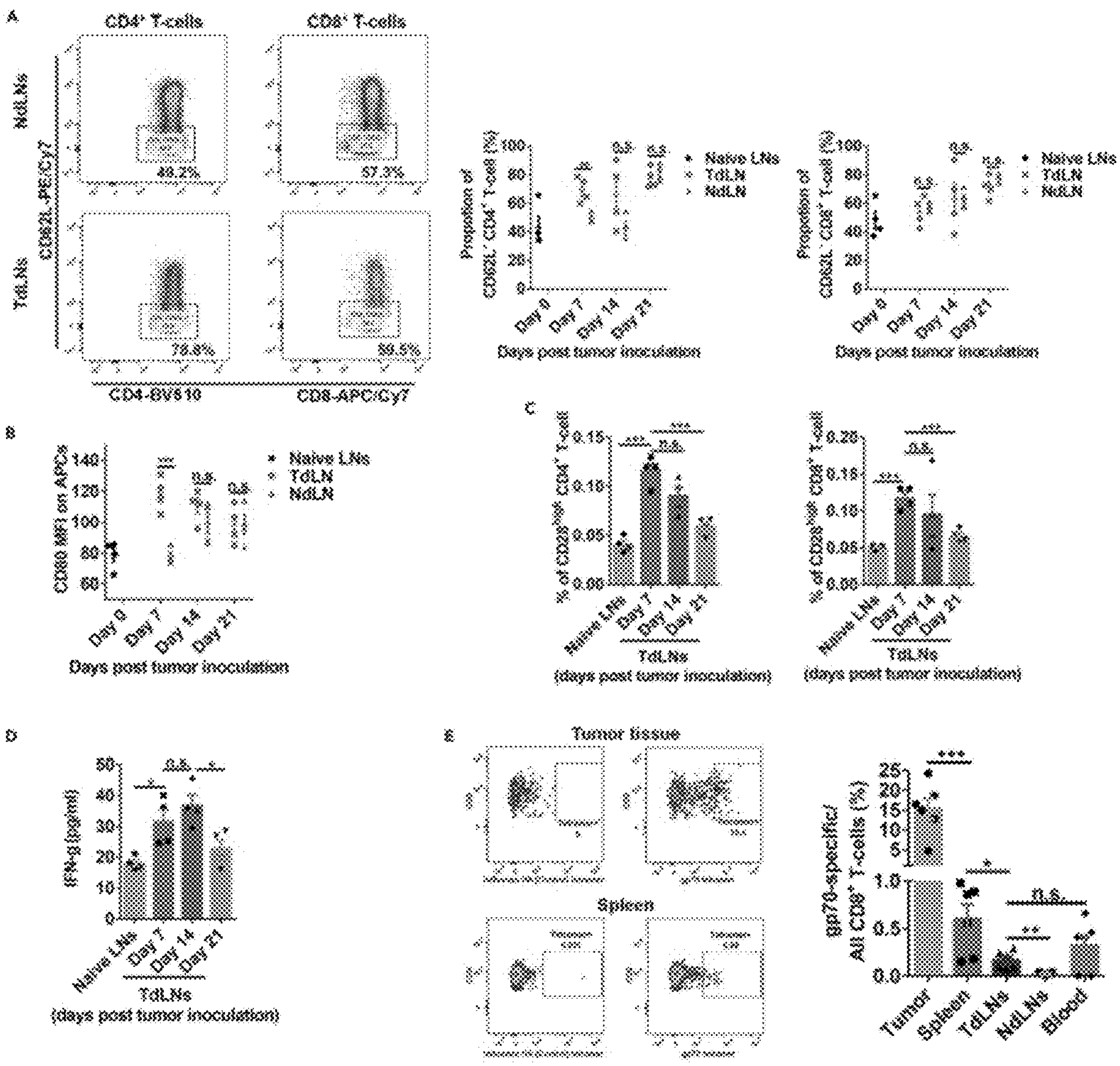
FIGS. 15A-15E show the functional status of TdLNs and tumor antigen-specific T-cell distribution in tumor-bearing mice with advanced disease.

TdLNs shift from an immunoactive to an immunotolerant environment and tumor-antigen specific T cells disseminate during tumor development Based on the above results, we then hypothesized that immunosuppression in TdLNs and systemic spreading of tumor antigen-specific T cells during tumor development make the TdLNs less important for late-stage tumors compared with early-stage tumors. We collected the TdLNs and NdLNs at different stages of tumor development for analysis and compared them with the naïve LNs. The frequency of $CD62L^-$ $CD4^+$ T cells was significantly higher in TdLNs than in NdLNs when tumors were small. However, the differences disappeared once the tumors became large (FIG. 15A). CD80, a crucial co-stimulatory molecule was higher on APCs in TdLNs than in NdLNs and naïve LNs at early-stage disease (FIG. 15B). However, with tumor development, the CD80 level on APCs in TdLNs dropped (FIG. 15B). As the receptor of CD80, CD28 is highly expressed on CD4+ and CD8+ T cells in TdLNs of early-stage tumors but decreased dramatically during tumor development (FIG. 15C). Previous studies showed that CD28 is downregulated in T cells which are repetitively exposed to antigens (Lake et al., 1993; Vallejo et al., 1999). Therefore, high numbers of T cells with lower CD28 levels may be the product of repeated activation in the TdLNs of late-stage tumors. However, recent studies indicated that sustained CD28 expression after T-cell priming is required for T-cell function and response to further stimulations, including immune checkpoint inhibitors (Kamphorst et al., 2017; Linterman et al., 2014). IFN-γ is highly produced by functional T cells. However, decreased IFN-γ concentration was observed in TdLNs during tumor development (FIG. 15D). These data suggested that immune cells in TdLNs of late-stage tumors may not function as properly as in the TdLNs of early-stage tumors, shifting the TdLNs from an immunoactive to the immunotolerant environment during tumor development.

The amount and distribution of tumor antigen-specific T cells also influence antitumor immunity and immunotherapy response (Liu et al., 2016). We measured the distribution of tumor antigen-specific T cells in mice with established tumors (volume 500-700 $mm^3$) (FIG. 21). As expected, the frequency of gp70 specific $CD8^+$ T cells was highest in the tumor-infiltrating CD8+ T cells population. The gp70 specific $CD8^+$ T cells were detected in all major peripheral lymphatic organs, including spleen, TdLNs, NdLNs, and blood (FIG. 15E). The proportion of $CD4^+$ (around 55%-65% of all T cells) and $CD8^+$ (around 25%-35% of all T cells) T cells in TdLNs was comparable with that in the naïve mice LNs (data not shown). Considering that TdLNs are only a very small proportion of the lymphatic system, our data suggested that in advanced tumor conditions, TdLNs are not the primary reservoir of tumor antigen-specific T cells. The widely distributed tumor antigen-specific T cells in peripheral lymphatic organs could be the responders of immunotherapies for controlling localized residual tumor (minimal secondary tumors in our model) recurrence.

Figures 16A, 16B, 16C:
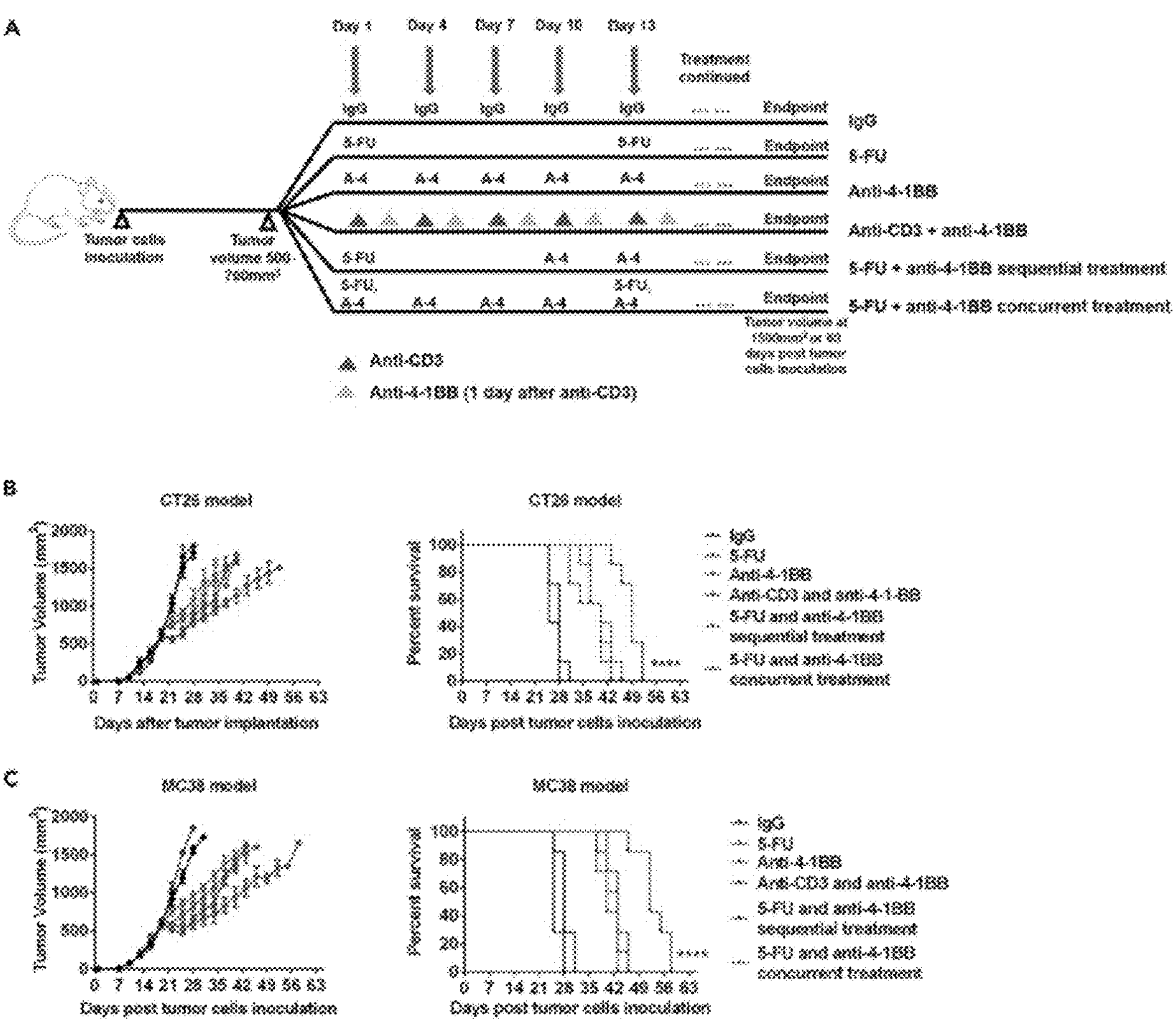
FIGS. 16A-16C show that 5-FU and anti-4-1BB sequential treatment elicits strong antitumor activity.
Figures 23A, 23B, 23C, 23D:
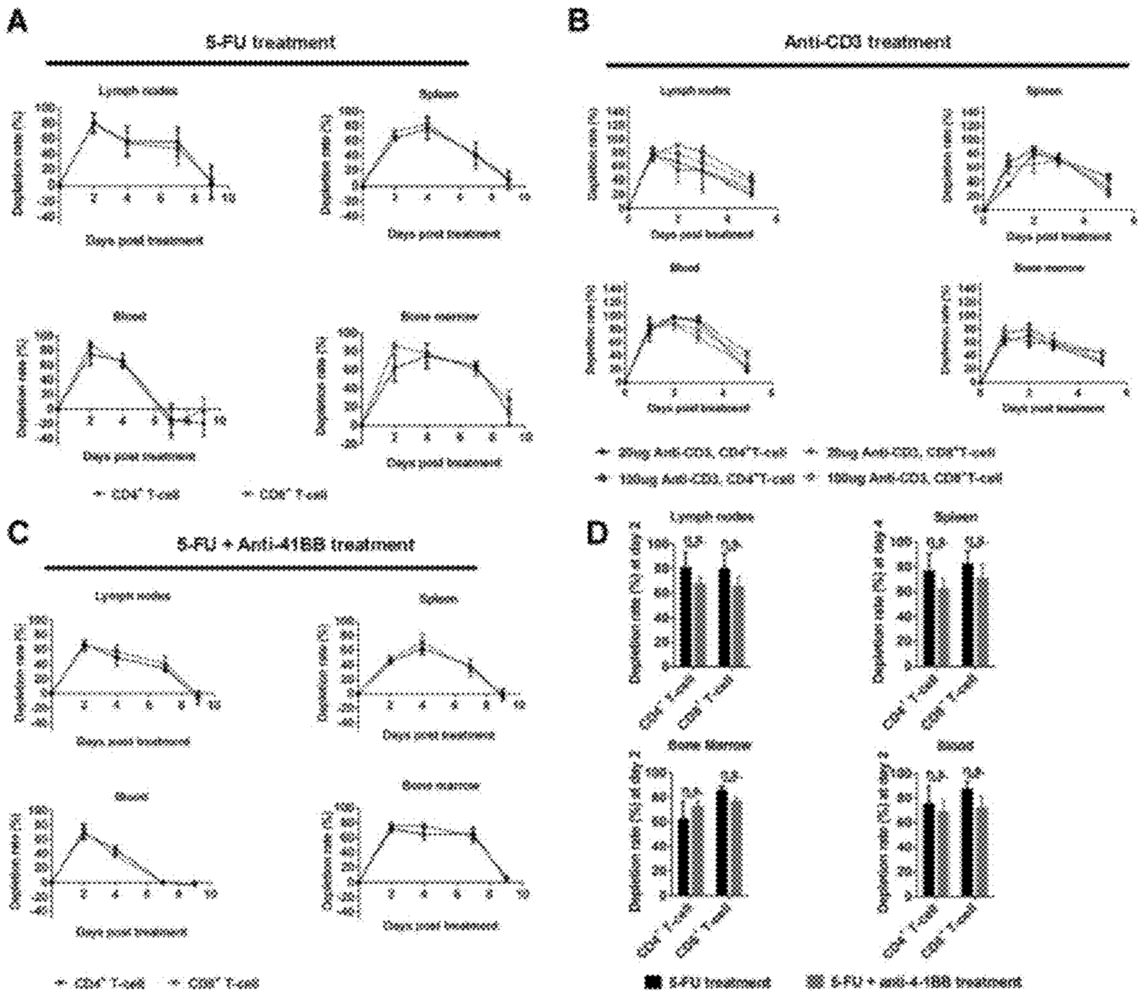
FIGS. 23A-23D show the T cell depleting effects of 5-FU and anti-CD3 treatment. Related to FIGS. 14 and 16-18.

Sequential Treatment of 5-FU and Anti-4-1BB or Anti-PD-1 Leads to Better Responses than Concurrent Treatment In addition to the primary tumor and TdLN resection, chemotherapy is a critical factor potentially affecting the efficacy of immunotherapies. Since our preceding data showed that TdLN resection may not affect the immunotherapeutic response, we then focused on the impacts of chemotherapy on immunotherapies. Several mechanisms by which chemotherapies regulate anti-tumor immunity have been identified (Emens and Middleton, 2015; Fend et al., 2017; Galluzzi et al., 2017; Pfirschke et al., 2016). However, no study has analyzed whether the schedule of combining chemotherapies with immunotherapies influences their synergetic effects. To investigate the impact of different combination therapy schedules on tumor response, we compared sequential versus concurrent 5-FU and anti-4-1BB or anti-PD-1 therapy in mouse models. The IgG and anti-4-1BB monotherapy in immunocompetent and T-cell depleted mice served as control groups (FIG. 16A). In mice with established tumors, anti-4-1BB monotherapy delayed tumor growth and prolonged mice survival time (FIG. 16B, C). Anti-CD3 impaired systemic immunity by suppressing T-cell populations (FIG. 23). In an established tumor model, anti-CD3 preconditioning nullified the anti-tumor effects of anti-4-1BB (FIG. 16B, C), indicating that intact systemic immunity was required for anti-4-1BB response. 5-FU also delayed tumor development in established tumor models (FIG. 16B, C). We then combined anti-4-1BB with the 5-FU treatment and found no noticeable improvement in mice survival time (FIG. 16B, C). In another cohort of mice, the 5-FU treatment was used as induction, and then later, anti-4-1BB was added as the maintenance treatment (FIG. 16B, C). To determine an appropriate sequential treatment strategy, we tested the dynamics of 5-FU induced T-cell depletion (FIG. 23). In the sequential treatment, anti-4-1BB was given when the T-cell population had almost recovered from the 5-FU treatment. Mice treated with sequential combination therapy had the longest survival time and the most effective tumor control of all cohorts (FIG. 16B, C).

Figures 17A, 17B, 17C:
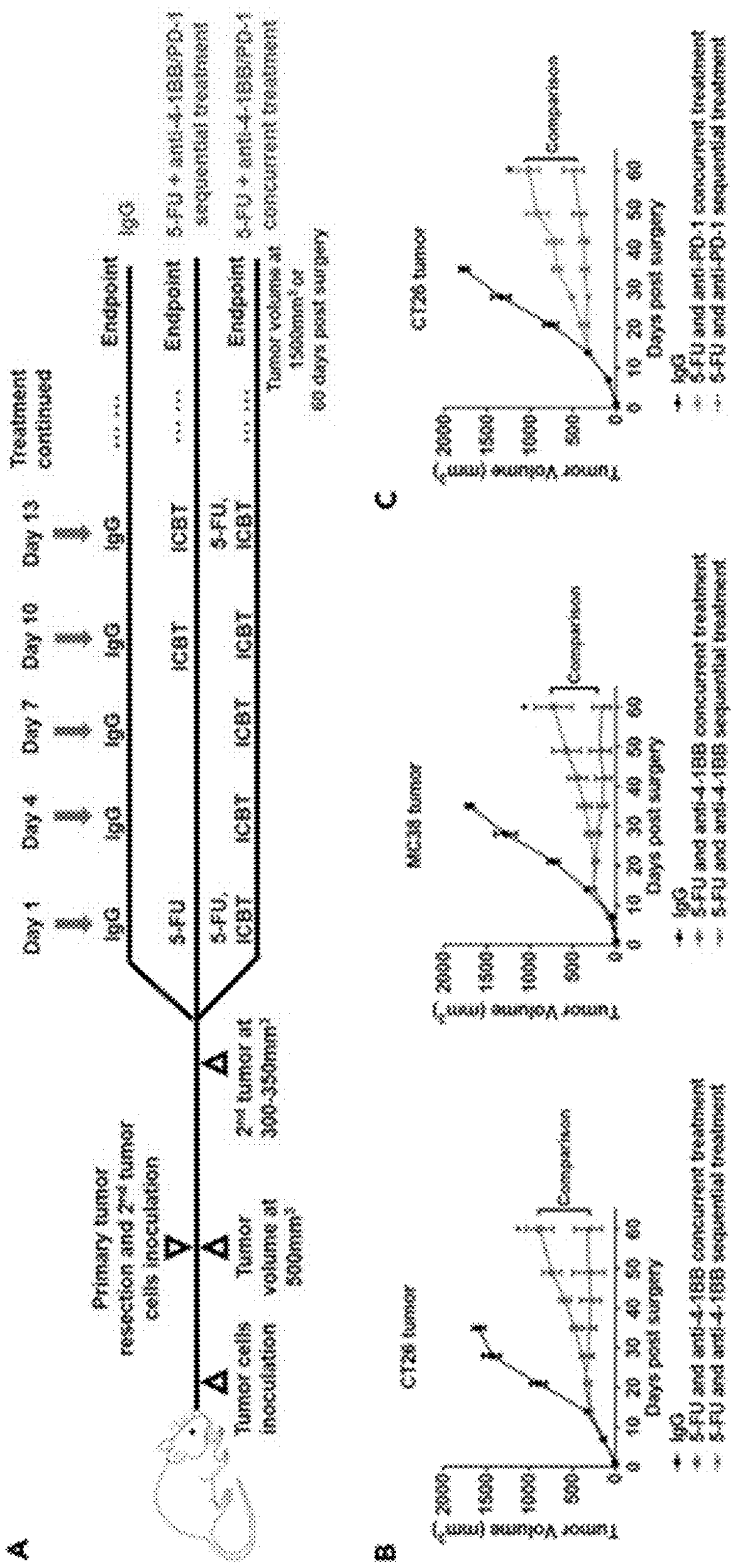
FIGS. 17A-17C shows that 5-FU and anti-4-1BB sequential treatment on secondary tumors mimic tumor recurrence.

Next, we compared the 5-FU and anti-4-1BB sequential and concurrent treatments in a more clinically relevant model. In this model, we performed resection of the established primary tumor together with its TdLNs and induced localized secondary tumors for treatment (FIG. 17A). Over 60 days of the experiment, the sequential treatment showed better tumor suppression than concurrent treatment (FIG. 17B). Anti-PD-1 is an FDA-approved class of cancer-directed immunotherapy with different mechanisms than anti-4-1BB. To test whether the conclusion from the anti-4-1BB treatment was generalizable to the anti-PD-1 treatment, we combined 5-FU and anti-PD-1 in concurrent and sequential schedules. Again, the 5-FU and anti-PD-1 given in sequence showed better tumor control than when administered concurrently (FIG. 17C).

Figures 24A, 24B, 24C, 24D:
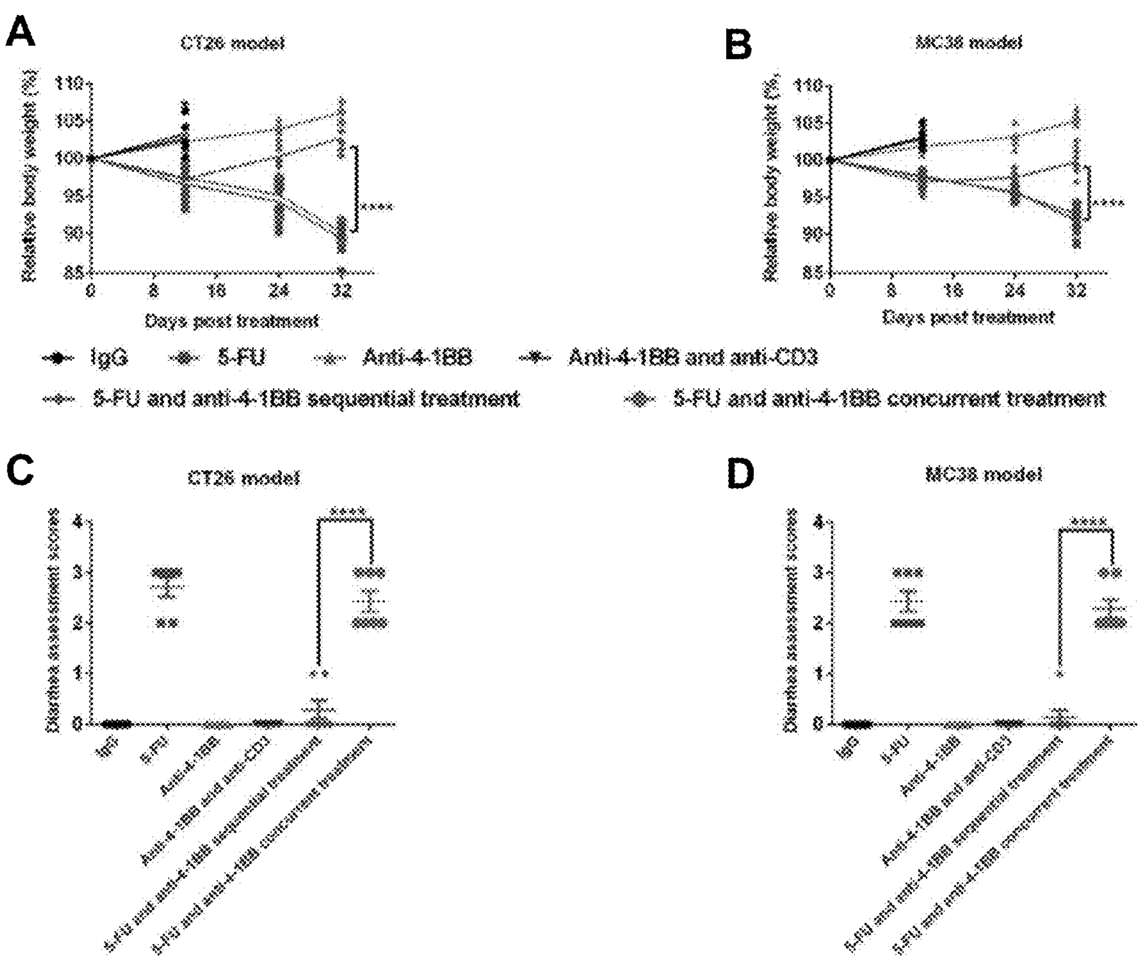
FIGS. 24A-24D show the side effects of different treatments. Related to FIG. 16.

Toxicity is a primary concern for cancer treatments, especially in combination therapy. We took this into account by evaluating the side effects of each treatment. 5-FU monotherapy and 5-FU and anti-4-1BB concurrent combination therapy caused severe body weight loss and diarrhea during the treatment (FIG. 24). In contrast, the 5-FU and anti-4-1BB sequential combination therapy showed slight or no side effects for the duration of the experiment (FIG. 24).

Figures 18A, 18B, 18C, 18D, 18E, 18F, 18G, 18H, 18I:
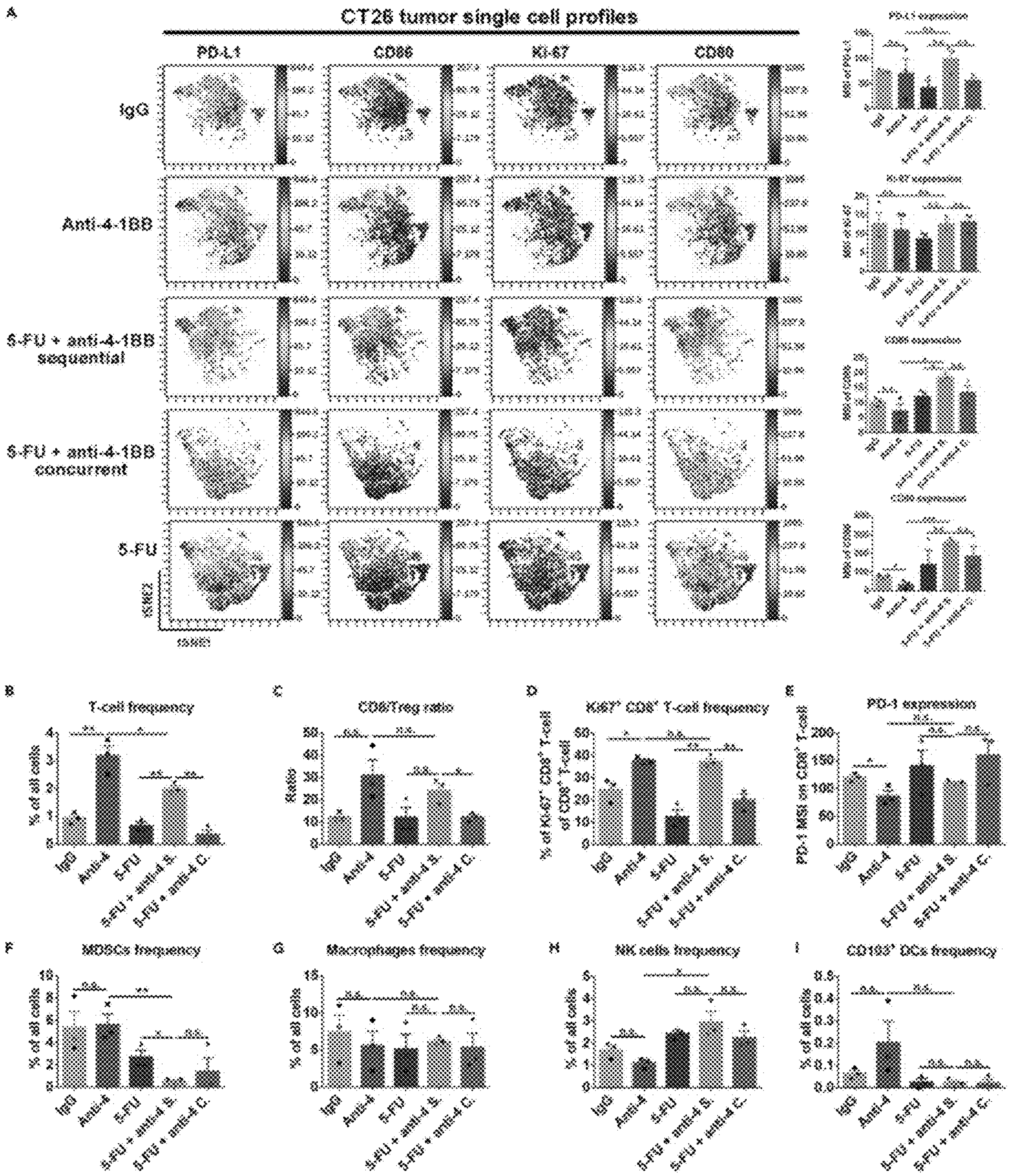
FIGS. 18A-18I show the tumor immunological response to 5-FU and anti-4-1BB treatments in CT26 tumors.
Figures 25A, 25B:
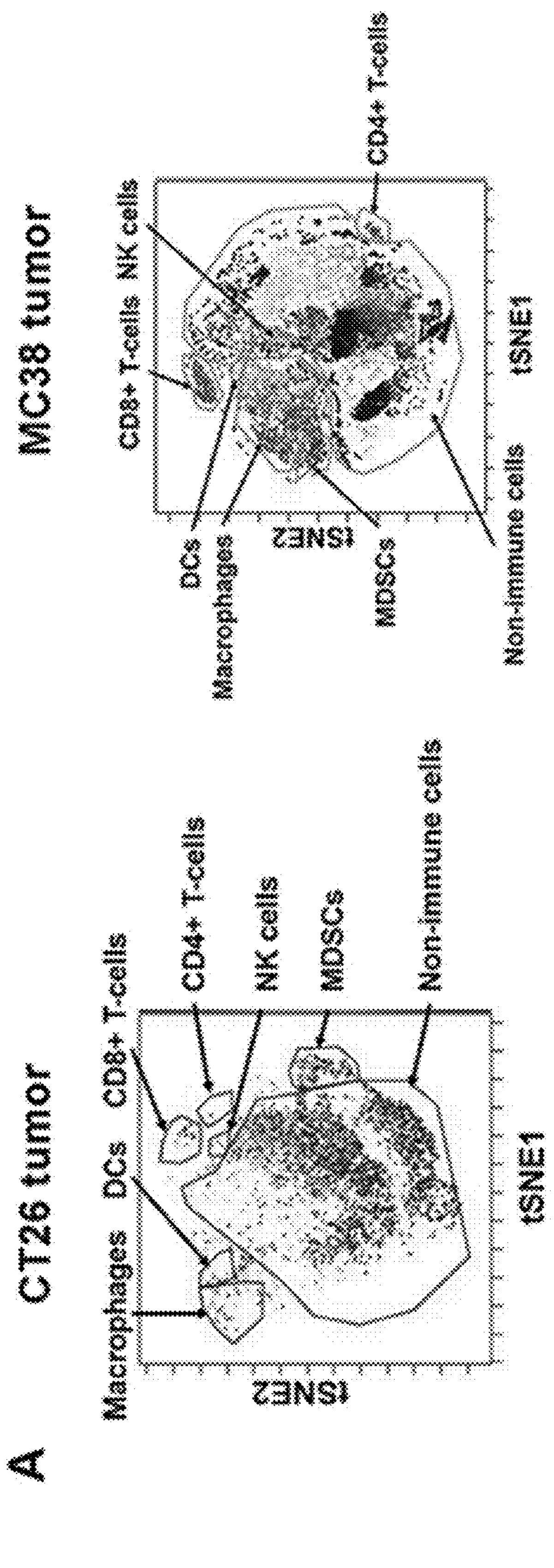
FIGS. 25A-25B show gating of the tumor-infiltrating immune cells. Related to FIG. 18.
Figures 25A, 25B:
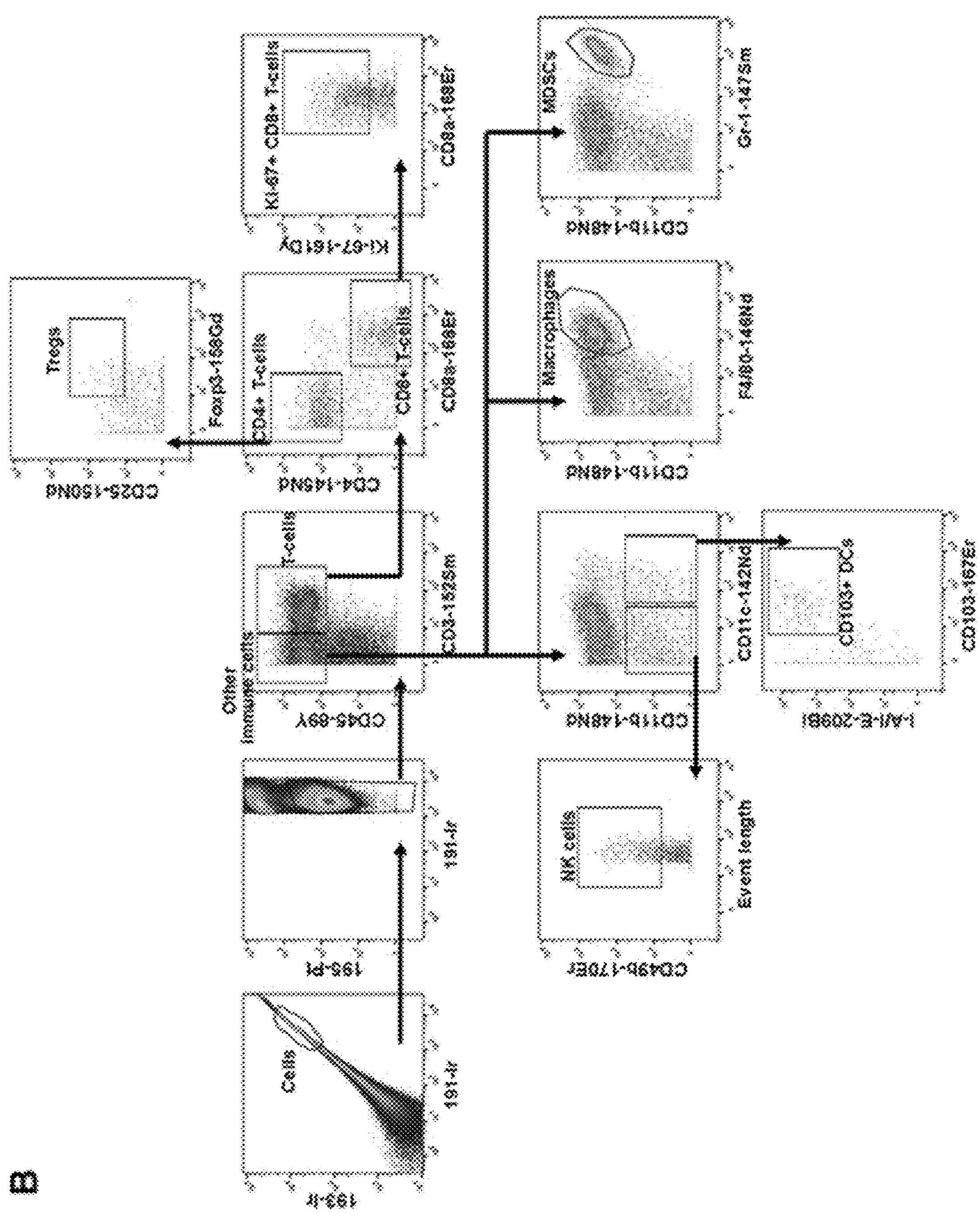

Sequential Treatment of 5-FU and Anti-4-1BB or Anti-PD-1 Stimulates a Strong Antitumor Immune Response Our pre-clinical models suggested that 5-FU and anti-4-1BB or anti-PD-1 sequential treatment has superior tumor controlling effects than the concurrent treatment schedule. We investigated the potential mechanisms of this result by performing mass cytometry to generate a comprehensive immune landscape characterization in tumor tissues (FIG. 25). Notably, CD80 and CD86 expression were upregulated after 5-FU and anti-4-1BB sequential treatment in CT26 tumors (FIG. 18A). High expression of these two critical co-stimulatory factors suggests enhanced tumor visibility by T cells. The expression of PD-L1 on tumor tissue was not significantly changed among different groups FIG. 18A). Furthermore, tumor immune infiltration studies showed that anti-4-1BB monotherapy stimulated tumor-infiltrating T-cell proliferation and increased the $CD8^+$ T-cell versus regulatory T-cell ratio (FIG. 18B, C, D). In sum, these experiments showed that 5-FU and anti-4-1BB sequential treatment alone maintained the positive effects of anti-4-1BB on the T cell population (FIG. 18B, C, D).

Meanwhile, the tumors treated by the sequential therapy had the lowest MDSC frequency and highest NK cell frequency (FIG. 18F, H). PD-1 expression on $CD8^+$ T cells and macrophages frequency was similar among all groups (FIG. 18E, G). $CD103^+$ DC frequency trended higher in the anti-4-1BB monotherapy group, but was not statistically significant (FIG. 18I). We repeated the same experiment in MC38 tumors (FIG. 26) and obtained similar results as in CT26 tumors with most parameters tested. However, CD80 and CD86 expression levels in MC38 tumors were not increased significantly by 5-FU and anti-4-1BB sequential treatments. This difference between MC38 and CT26 tumors indicates the tumor-dependent effects of the treatment. In CT26 tumors, we also evaluated the immunoregulatory effects of 5-FU and anti-PD-1 combination (FIG. 27). Tumor-wide expression of PD-L1, CD86, and CD80 was increased in 5-FU and anti-PD-1 sequential treatment group. In addition, the frequencies of total T cells, proliferating $CD8^+$ T cells and NK cell was highest in tumors treated by 5-FU and anti-PD-1 sequential therapy (FIG. 27). Notably, the frequency of MDSCs was decreased by 5-FU monotherapy and combination treatment (FIG. 27). These findings showed the immunological impacts of different treatment strategies and reinforced that using 5-FU as an induction treatment and then anti-4-1BB or anti-PD-1 as maintenance treatments produces the most prominent and synergic effect in reversing the immunosuppressive tumor microenvironment.

Discussion:

Immunotherapies are mostly used as second- or third-line treatments for treatment-refractory tumors. However, studies that investigate the impact of different clinical conditions and combination strategies on tumor immunotherapy are limited. Here, we comprehensively profiled the impacts of tumor-draining lymph nodes (TdLNs) resection and different chemotherapy combination schedules on ICBT responses.

Surgery has been a dominant strategy for several decades to prevent, diagnose, stage, and treat cancers. Radical surgery—a procedure that removes blood supply to the tumor, lymph nodes and sometimes adjacent structures—is routinely performed in many cancers such as colorectal cancer, breast cancer, and lung cancer. Early-stage cancer patients have excellent disease control with surgery alone, yet advanced diseases require more comprehensive treatments, including chemotherapies, oncogenic pathway targeted therapies, and immunotherapies. Currently, most immunotherapies are used as adjuvant treatments (given after surgeries). TdLNs are the primary lymphatic organs where antitumor immune responses are initiated (Fisher and Fisher, 1971; Jeanbart et al., 2014; Marzo et al., 1999; Munn and Mellor, 2006; Shu et al., 2006). In mouse models with resected TdLNs before tumor cell inoculation, we observed that removal of TdLNs significantly accelerated tumor growth and compromised response to immunotherapy. These data uncovered a key role for TdLNs in preventing cancer cells from evading antitumor immunity at early stages. Mechanistically, TdLNs resection in early-stage disease led to inadequate antitumor immune simulation, featured by a low frequency of tumor antigen-specific T cells in lymphatic organs. Our observations were in line with previous studies, highlighting the significance of TdLNs in initiating antitumor immunity and regulating immunotherapy response in early-stage disease (Fransen et al., 2018).

Recently, Fransen et al reported that TdLNs are determining factors of PD-1/PD-L1 immune checkpoint therapies in early-stage tumor models (Fransen et al., 2018). However, whether the TdLNs are critical for immunotherapy response in recurrent tumor models, which represent a major clinical issue, had not been addressed. In our study, we established a model to mimic tumor recurrence from residual tumor lesions after primary tumor and TdLN resection. We first thoroughly resected the primary tumors either with or without TdLN resection and confirmed a clean surgical margin. We then inoculated tumor cells in situ to induce a secondary tumor. This method allows all secondary tumors to have a relatively similar baseline volume and growth dynamic before any treatment. We also allow the localized secondary tumors to connect with systemic circulation and establish a tumor microenvironment before treatment was initiated. Our well-designed model provided a platform for an unbiased evaluation of treatment efficacy in residual disease after primary tumor resection.

With our model, we found that resection of TdLNs in advanced tumors did not influence localized secondary tumor immunity and response to immunotherapies (anti-PD-1 and anti-4-1BB). Furthermore, we investigated the factors that determine the significance of TdLNs in antitumor immunity and immunotherapeutic response. Previous findings indicated that the bidirectional crosstalk between tumor cells and TdLNs allowed remodeling of each other during tumor progression (Fisher and Fisher, 1971; Ito et al., 2006; Munn and Mellor, 2006; Shu et al., 2006; Watanabe et al., 2008). Immunosuppressive factors derived from tumors such as TGFβ, can drain to TdLNs and induce an immunosuppressive microenvironment (Cochran et al., 2006; Ito et al., 2006). We tested the hypothesis that antitumor function of TdLNs is impaired in advanced tumor models. We compared the immune responses in naïve LNs, TdLNs of early-stage and advanced tumors and demonstrated a trend between potent immunosuppression in TdLNs and tumor progression. Although the TdLNs eventually became immunotolerant, the distribution of tumor antigen-specific T cells are extensive in lymphatic tissues in advanced tumors. Resection of TdLNs did not significantly reduce the population of tumor-antigen specific T cells that respond to immunotherapies. Our data corroborate with previous reports showing strong immunosuppression development in TdLNs of human cancers (Murthy et al., 2019; Shuang et al., 2017). This explains why resection of TdLNs may not influence the antitumor immunity in late-stage tumor models. Finally, it is also important to understand that the resected TdLNs in our experimental models might have developed immunotolerance. However, since humans have more TdLNs than the mouse model, immunoactive TdLNs do exist in certain circumstances and might influence immunotherapy response (Toki et al., 2020; Wu et al., 2014). Therefore, it will be critical to evaluate the functional status of TdLNs in humans before extending our conclusions to human cancers.

Systemic therapies, such as chemotherapies are used to treat primary tumors, eradicate micrometastatic disease, or stabilize the disease in widespread incurable conditions (DeVita and Chu, 2008). Chemotherapies have the advantages of being fast-acting and effective, thus they are widely administered as the primary treatment for combinational strategies (DeVita and Chu, 2008). Combinations of chemotherapies with immunotherapies are extensively discussed and currently tested in pre-clinical models and clinical trials (Emens and Middleton, 2015; Kareva, 2017; Pfirschke et al., 2016; Wang et al., 2018). Comprehensive studies have revealed the mechanisms by which chemotherapy can promote antitumor immunity by induction of immunogenic cell death and disruption of tumor microenvironment components that are used to evade the immune response (Galluzzi et al., 2017; Lutsiak et al., 2005; Michels et al., 2012; Samanta et al., 2018; Tesniere et al., 2010). However, cancer chemotherapies are also considered immunosuppressive due to their cytotoxic effects on immune cells. Therefore, we speculated that the same chemotherapy may have different impacts on anti-tumor immunity, either stimulatory or inhibitory, depending on the specific combination schedules. We used 5-FU, a common chemotherapeutic agent, as a representative agent to study the influences of different chemotherapeutic and immunotherapeutic combination strategies on the anti-tumor immune response.

Through extensive study of 5-FU induced immune responses, we revealed both systemic immunosuppressive effects and immune-stimulating effects in the tumor microenvironment. 5-FU treatment upregulated CD80 expression and depleted MDSCs. CD80 is a protein found on antigen-presenting cells as well as tumor cells and belongs to the B7 family; it provides a costimulatory signal necessary for activating T cells and natural killer cells (Beyranvand Nejad et al., 2016; Chambers et al., 1996; Lanier et al., 1995; Singh et al., 2003). Thus, the upregulation of CD80 in tumor tissue induced by 5-FU treatment will potentially lead to increased tumor visibility by T cells. MDSCs are a heterogeneous population of cells that potently suppress T-cell responses (Kumar et al., 2016; Veglia et al., 2018). By depleting MDSCs in tumor tissue, 5-FU treatment may potentiate antitumor immunity by eliminating the negative regulations. These findings are also supported by a previous report (Vincent et al., 2010). In addition to the immunogenic effects, we also observed that 5-FU treatment suppressed the T-cell population in the tumor microenvironment. Thus, avoiding the immunosuppressive effects and preserving the immunogenic effects of 5-FU treatment will determine the response of 5-FU and immunotherapy combinations.

In our study, the administration of anti-4-1BB or anti-PD-1 after 5-FU treatment significantly improved tumor responses. In this combination strategy, anti-4-1BB or anti-PD-1 selectively boosted response of T-cell and NK cells while the 5-FU treatment increased tumor visibility and suppressed MDSCs. However, when anti-4-1BB or anti-PD-1 was added to the repetitive 5-FU treatment, less synergistic effects were observed. Our data highlighted the importance of determining the best schedule for designing a successful chemo-immunotherapy combination. In addition to timing, dosing is another potential factor that affects the chemotherapy-induced immune response. Low dose chemotherapies have shown special immunoregulatory effects in tumor models (Cao et al., 2014; Ghiringhelli et al., 2007). Further studies are needed to test different chemotherapy doses on the chemo-immunotherapy combination.

In conclusion, our research investigated how traditional cancer treatments will affect novel immunotherapies in clinically relevant tumor models. Our findings indicate that TdLN resection can have adverse impact on anti-tumor immunity, but only in early-stage tumor models. In advanced tumor models, resection of immunotolerant TdLNs during primary tumor surgery does not significantly alter anti-tumor immunity or immunotherapy response in secondary tumors that mimic localized tumor recurrence. Meanwhile, minimizing the immunosuppression and strengthening the immunogenic effects of traditional cancer therapies are critical for immunotherapy induced durable cancer remission. Specifically, sequential cytotoxic chemotherapy followed by immunotherapy produced a significantly higher degree of anti-tumor response compared to concurrent combination therapy. These findings highlight the need to test immunotherapies in tumor models that more closely mimic different clinical conditions and establish references for designing clinical trials to determine the most effective cancer immunotherapy strategies.

Materials and Methods:

Cell Cultures

Murine CRC cell lines CT26 (purchased from American Type Culture Collection (ATCC)) and MC38 (gift from Dr. Nicholas Haining) were used for the study and were authenticated by STR profiling. CT26 cells were maintained in complete RPMI-1640 medium (GIBCO BRL), supplemented with 10% heat-inactivated FBS (Thermo Fisher Scientific), 100 IU/mL penicillin, and 100 μg/mL streptomycin (Invitrogen Life Technologies). MC38 cells were cultured in the complete DMEM medium (GIBCO BRL) with the same supplements as the RPMI 1640 medium. All cells were routinely authenticated and tested for *mycoplasma.*

Mice

Wild type BALB/c mice (6-8 weeks old, Jackson Laboratory) and C57BL/6 mice (6-8 weeks old, Charles River Laboratories) were used for animal studies. All mice were kept in a specific pathogen-free facility with fully autoclaved cages to minimize non-tumor specific immune activation. Animal studies were approved by the institutional animal care and use committee (IACUC). All mice are female. We don't expect the any influence of gender on our study aims.

Subcutaneous Tumor Induction

For the subcutaneous syngeneic model, the cells were harvested at low passages, washed, and resuspended in Matrigel matrix (Corning Inc.) before injection. Mice were shaved right before injection. CT26 ($2\times10^5$ cells/injection) or MC38 ($5\times10^5$ cells/injection) cells were inoculated subcutaneously into the right hind-flank of 6 to 8-week-old female BALB/c or C57BL/6 mice. The same amount of tumor cells were used for the rechallenge experiment in FIG. 13. Tumor length and width were measured every three to seven days, and the volume was calculated according to the formula (length×width$^2$)/2. Mice were divided into different experimental groups at random when tumors reached a specific size.

Identification of Major Tumor-Draining Lymph Nodes

To identify the major tumor-draining lymph nodes (TdLNs), we injected 50 μl 1% Evans blue (Sigma-Aldrich) or 50 μl 1% Alexa Fluor® 488 dye (Thermo Fisher Scientific) into the subcutaneous tumor (~400-500 mm3) at the right hind flank. The left and right inguinal LNs, axillary LNs, brachial LNs, popliteal LNs, and mesentery LNs were taken at 10 min, 30 min, and 60 min post Evan blue injection. For the fluorescence-labeled group, we collected LNs at 0.5 h, 3 h, 24 h, and 48 h post-injection. The intact LNs were visually examined for Evans blue staining. LNs, spleen, and tumor tissues were ground and meshed for single cell suspension, which was measured by flow cytometry for Alexa Fluor® 488 dye signal. To evaluate the physical change of LNs and spleen during tumor development, we weighted LNs and spleen from naïve mice and mice with different sizes of the tumor (100-200 $mm^3$, 500-700 $mm^3$, or 1200-1500 $mm^3$).

Subcutaneous Tumor and TdLNs Resection

Primary tumors were resected when they reached the indicated volume as shown in the experimental schematics in each figure. Tumor-bearing mice were anesthetized with Ketamine (100 mg/kg) and Xylazine (10 mg/kg) by intraperitoneal injection. To minimize animal pain, we administrated Buprenorphine (slow-releasing, 2 mg/kg) subcutaneously 2 hours before anesthesia. Mice were prepared by removing hair from the skin region over the tumor. We prepared the skin by wiping with iodine prep pads and then alcohol prep pads. Resections were performed by elliptical incisions, 5 mm left to the subcutaneous tumors. With iris scissors, we separated the capsule of subcutaneous tumors from the surrounding connective tissue to isolate and resect intact tumors. Once tumors were removed from the adjacent fascia, the incisions were sutured with 5/0 vicryl ties (polyglactin 910, Ethicon). For the TdLNs resection, the TdLNs were located based on the superficial anatomic landmark points. The mice were prepared as mentioned above. A 5-10 mm incision was made and TdLNs were removed. Then the skin was sutured with 5/0 vicryl ties. For tumor rechallenge, 1 day after surgery, we inoculated the secondary tumor (CT26: 5×105 cells/injection, MC38: 1×106 cells/injection) to the surgical site to mimic tumor recurrence.

RT-qPCR

We used the murine leukemia virus envelope gp70 as a biomarker of tumor burden. Biopsies were collected from normal mouse skin, tumor tissue, and surgical margin after tumor resection. The mirVana microRNA (miRNA) Isolation Kit (Thermo Fisher Scientific) was used to extract total RNA from these biopsies. 500 ng of total RNA was used for establishing the cDNA library with the QuantiTect Reverse Transcription Kit (Qiagen). We used the LightCycler 480 Instrument (Roche Life Science) to measure 18S ribosomal RNA (rRNA) and gp70 expression.

Primers used: 18S rRNA forward primer: GTTGGTTTTCGGAACTGAGG (SEQ ID NO: 22), 18S rRNA reverse primer: AGTCGGCATCGTTTATGGTC (SEQ ID NO:23), gp70 forward primer: AAAGTGACACATGCCCACAA (SEQ ID NO:24), gp70 reverse primer: CCCCAAGAGGCACAATAGAA (SEQ ID NO:25; Scrimieri et al., 2013).

Flow Cytometry

Flow cytometry was used to measure tumor tissue immune infiltration, tumor antigen-specific T cells, and immune cell functions. Harvested tumor tissues were chopped into small pieces (around 3 mm×3 mm) and then digested in a solution of collagenase IV (1 mg/ml) and deoxyribonuclease (DNase, 50 units/ml) at 37° C. for 1 hr with shaking. The digested tissue was then meshed and filtered through a 70 μm cell strainer. The cell suspension was centrifuged and resuspended in red blood cell lysis buffer for 15 minutes at room temperature (RT) for eliminating red blood cells. Another centrifugation was performed to get the cell pellet for staining. For the lymphatic organs, we directly meshed the tissue and filtered through a 40 μm cell strainer to get single cell suspension, followed by red blood cells elimination.

Following the tissue sample preparation, cells were stained with the fixable cell viability dye and then cell surface marker antibodies for a 15 min incubation at 4° C. Next, cells were fixed and permeabilized for intracellular staining for a 30 min incubation at RT. The cells were finally stained with intracellular markers (30 min at RT) and analyzed on a BD FACS-CANTO instrument (BD Biosciences). To analyze the tumor antigen-specific T cells, we performed H-2Ld MuLV gp70-SPSYVYHQF (SEQ ID NO:26) APC conjugated tetramer (MBL International) staining by following the manufacturer's instruction, before antibody staining. The influenza hemagglutinin-IYST-VASSL (SEQ ID NO:27) APC conjugated tetramer (MBL International), which should only stain a very minimal population of T cells in mice without influenza hemagglutinin stimulation, was used as a negative control for ruling out false positive in the tetramer staining and setting up the gate for gp70 tetramer. Lymphatic tissues from naïve mice were also used as negative controls. According to the manufacture's instruction and our preliminary experiment optimization, we used anti-CD8 (clone KT15) antibody (MBL International) to further reduce false-positive rate of the tetramer staining. All antibodies for flow cytometry were purchased from Biolegend and summarized in supplementary materials. Data were analyzed using FlowJo software (Tree Star, Inc.).

Mass Cytometry

Details on antibodies and reagents used are listed in materials table. We purchased the prelabeled antibodies from Fluidigm Corporation and unlabeled antibodies (MaxPar® Ready purified) from Biolegend. Conjugation of the purified antibodies with metal tags was performed by using the MaxPar X8 antibody labeling kit (Fluidigm Corporation) according to the manufacturer's instructions. The metal tagged antibodies were then validated and titrated in positive control and negative control samples.

Tumor samples were collected and digested using standard flow cytometry procedure. A total of 3 million single cells were used for each mass cytometry staining. In brief, the single cell pellets were first incubated with Cell-ID Cisplatin with a final concentration of 5 μM for 5 min at RT to identify dead cells. Cells were then washed and blocked by Fc-receptor blocking solution. Cell membrane staining was then performed with metal-conjugated antibodies for 30 min at RT. After staining, cells were fixed and permeabilized. The intracellular staining antibodies were then added and incubated for 45 min at RT. Finally, cells were labeled with 1 ml 1,000× diluted 125 μM Cell-ID intercalator-Ir to stain all cells in MaxPar Fix and Perm Buffer overnight at 4° C. EQ Four Element Calibration Beads with the reference EQ passport P13H2302 were added to each staining tube right before data acquisition by a CyTOF 2 mass cytometer. The mass cytometry data were then normalized and exported for gating on alive single cells, which were then imported to the Cytobank software. A t-SNE analysis was performed with default parameters (perplexity, 30; iterations, 1,000) on all cell types in tumor samples.

Mouse IFN-γ Enzyme-Linked Immunosorbent Assays

Mouse naïve lymph nodes and TdLNs were collected, weighed, and ground in 100 μl RIPA lysis and extraction buffer. After the tissues were lysed, the total protein was used for enzyme-linked immunosorbent assay (ELISA, Affymetrix) to detect mouse IFNγ, by following the manufacturer's protocol.

Histology

Mouse naïve lymph nodes, TdLNs, and non-tumor draining lymph nodes (NdLNs) were collected and fixed in 10% formalin for 24 hr. Tissues were embedded in paraffin and cut for hematoxylin and eosin (H&E) staining. The whole tissue sections were scanned and analyzed for potential metastatic tumor cells.

T Cell Depletion

We tested the effects of 5-FU treatment and 5-FU and anti-4-1BB combination treatment on T cell depletion in vivo. Intraperitoneal administration of anti-CD3 treatment (clone: 17A2, BioXcell, 5 mg/kg every 3 days) was given to induce T cell depletion in mice. One dose of 5-FU (150 mg/kg) or 5-FU (150 mg/kg) and anti-4-1BB (5 mg/kg) combination treatment was given intraperitoneally in naïve mice. Mice were sampled on days 2, 4, 7, and 9 after treatment for quantifying T cells in lymph nodes, spleen, bone marrow, and blood circulation.

Mouse Treatments

Mice were treated with IgG (5 mg/kg as an anti-4-1BB control, 10 mg/kg as an anti-PD-1 control), 5-FU (150 mg/kg), anti-4-1BB agonist (5 mg/kg, clone: 3H3), or anti-PD-1 (10 mg/kg, clone: RMP1-14) for treatment purpose. For the 5-FU monotherapy, one dose of 5-FU was given every 12 days to minimize the severe side effects. For anti-4-1BB and IgG monotherapy, mice were treated every 3 days. For the 5-FU and anti-4-1BB sequential treatment, anti-4-1BB treatment started 9 days after one dose 5-FU treatment and continued as 3 days per injection after that. For the 5-FU and anti-4-1BB concurrent treatment, we added the anti-4-1BB cycle to the 5-FU cycle. The anti-PD-1 was used as the same as the anti-4-1BB cycle. All treatments were given intraperitoneally and continued until the endpoint of study design. The treatment starting points and endpoints varied in different experiments for different purposes and were shown in the individual figure or figure legend.

5-FU Toxicity Evaluation

We recorded animal body weight and diarrhea scores after treatments. Mice were weighed on day 12, 24, and 32 after treatment. The diarrhea score was assessed at the endpoint of each treatment by using a 4-point scoring system: 0=normal stool; 1=slight diarrhea (soft formed stool without perianal staining of the coat); 2=moderate diarrhea (unformed stool with moderate perianal staining of the coat); and 3=severe diarrhea (watery stool with severe perianal staining of the coat) (Song et al., 2013).

Statistical Analysis

All statistical analyses and graphing were performed using GraphPad Prism software (Version 6). Data were displayed as means±SEMs. For comparison of two groups' quantitative data, paired or unpaired Student's t-test was performed. When applicable, one-way analysis of variance (ANOVA) was utilized for multiple groups' comparison, followed by post hoc (Tukey's) multiple comparisons test. Kaplan-Meier curves were plotted to visualize mouse survival, and log-rank tests were used to compare survival outcomes between subgroups. A two-tail P value of less than 0.05 was considered statistically significant.

TABLE 3

| Key materials | | | |
|---|---|---|---|
| Reagent for immune assays | Clone | Vendor | Identifier |
| Anti-mouse CD3-FITC | 17A2 | BioLegend | 100204 |
| Anti-mouse CD28-PE | 37.51 | BioLegend | 102106 |
| Anti-mouse PD-1-PerCP/Cy5.5 | 29F.1A12 | BioLegend | 135208 |
| Anti-mouse CD62L-PE/Cy7 | MEL-14 | BioLegend | 104418 |
| Anti-mouse CD8a-APC/Cy7 | 53-6.7 | BioLegend | 100714 |
| Anti-mouse LAG-3-BV421 | C9B7W | BioLegend | 125221 |
| Anti-mouse/human CD44-PE | IM7 | BioLegend | 103008 |
| Anti-mouse CD19-Pacific Blue | 6D5 | BioLegend | 115523 |
| Anti-mouse CD4-BV510 | GK1.5 | BioLegend | 100449 |
| Anti-mouse CD86-PE | GL-1 | BioLegend | 105007 |
| Anti-mouse F4/80-PE/Cy5 | BM8 | BioLegend | 123111 |
| Anti-mouse CD80-PE/Cy7 | 16-10A1 | BioLegend | 104734 |
| Anti-mouse/human CD11b-APC | M1/70 | BioLegend | 101212 |
| Anti-mouse I-A/I-E-APC/Cy7 | M5/114.15.2 | BioLegend | 107628 |
| Anti-mouse CD11c-BV510 | N418 | BioLegend | 117338 |
| Anti-mouse CD45-Pacific Blue | 30-F11 | BioLegend | 103126 |
| Anti-mouse CD45-FITC | 30-F11 | BioLegend | 103108 |
| Anti-mouse CD3-PerCP/Cyanine5.5 | 17A2 | BioLegend | 100218 |
| Anti-mouse CD3ε-PE/Cy7 | 145-2C11 | BioLegend | 100320 |
| Anti-mouse CD 103-Pacific Blue | 2E7 | BioLegend | 121418 |
| Anti-mouse Gr-1-PE/Cy7 | RB6-8C5 | BioLegend | 108416 |
| Anti-mouse CD45-BV510 | 30-F11 | BioLegend | 103138 |
| Anti-mouse Podoplanin-APC/Cy7 | 8.1.1 | BioLegend | 127418 |
| Anti-mouse CD31-Pacific Blue | 390 | BioLegend | 102422 |
| Anti-mouse CD45-89Y | 30-F11 | Fluidigm | 3089005B |
| Anti-mouse Ly-6G-41Pr | 1A8 | Fluidigm | 3141008B |
| Anti-mouse CD11c-142Nd | N418 | Fluidigm | 3142003B |
| Anti-mouse CD4-145Nd | RM4-5 | Fluidigm | 3145002B |
| Anti-mouse F4/80-146Nd | BM8 | Fluidigm | 3146008B |
| Anti-mouse Gr-1-147Sm | RB6-8C5 | BioLegend/ Fluidigm | 108449/ 201147B |
| Anti-mouse CD11b-148Nd | M1/70 | Fluidigm | 3148003B |
| Anti-mouse CD19-149Sm | 6D5 | Fluidigm | 3149002B |
| Anti-mouse CD25-150Nd | 3C7 | Fluidigm | 3150002B |
| Anti-mouse CD28-151Eu | 37.51 | Fluidigm | 3151005B |
| Anti-mouse CD3e-152Sm | 145-2C11 | Fluidigm | 3152004B |
| Anti-mouse CD274-153Eu | 10F.9G2 | Fluidigm | 3153016B |
| Anti-mouse CD152-154Sm | UC10-4B9 | Fluidigm | 3154008B |
| Anti-mouse CD279-155Gd | RMP1-30 | BioLegend/ Fluidigm | 109113/ 201155A |
| Anti-mouse CD335-156Gd | 29A1.4 | BioLegend/ Fluidigm | 137625/ 201156B |
| Anti-mouse Foxp3-158Gd | FJK-16s | Fluidigm | 3158003A |
| Anti-mouse RORgt-B2D-159Tb | B2D | Fluidigm | 3159019B |
| Anti-mouse CD62L-160Gd | MEL-14 | Fluidigm | 3160008B |
| Anti-mouse Ki-67-161Dy | B56 | Fluidigm | 3161007B |
| Anti-mouse Ly-6C-162Dy | HK1.4 | Fluidigm | 3162014B |
| Anti-mouse CD197-164Dy | 4B12 | Fluidigm | 3164013A |
| Anti-mouse IFNg-165Ho | XMG1.2 | Fluidigm | 3165003B |
| Anti-mouse IL-4-166Er | 11B11 | Fluidigm | 3166003B |
| Anti-mouse CD103-167Er | 2E7 | BioLegend/ Fluidigm | 121402/ 201167B |
| Anti-mouse CD8a-168Er | 53-6.7 | Fluidigm | 3168003B |
| Anti-mouse CD49b-170Er | HMa2 | Fluidigm | 3170008B |
| Anti-mouse CD80-171Yb | 16-10A1 | Fluidigm | 3171008B |
| Anti-mouse CD86-172Yb | GL1 | Fluidigm | 3172016B |
| Anti-mouse Granzyme B-173Yb | GB11 | Fluidigm | 3173006B |
| Anti-mouse CD127-174Yb | A7R34 | Fluidigm | 3174013B |
| Anti-mouse CD44-176Yb | IM7 | BioLegend/ Fluidigm | 103051/ 201176B |
| Anti-mouse I-A/I-E-209Bi | M5/114.15.2 | Fluidigm | 3209006B |
| Cell-ID ™ Intercalator-Ir | NA | Fluidigm | 201192B |
| Cell-ID ™ Cisplatin | NA | Fluidigm | 201064 |
| H-2Ld MuLV gp70 Tetramer-APC | NA | MBL International | TB-M521-2 |
| IFN gamma Mouse ELISA Kit | NA | Thermo Fisher Scientific | BMS606 |
| Zombie Violet ™ Fixable Viability Kit | NA | BioLegend | 423113 |

TABLE 3-continued

| | | | |
|---|---|---|---|
| Zombie Aqua ™ Fixable Viability Kit | NA | BioLegend | 423101 |
| Zombie Green ™ Fixable Viability Kit | NA | BioLegend | 423111 |
| MuLV gp70 Tetramer-APC | NA | MBL International | TB-M521-2 |
| Influenza HA Tetramer-APC | NA | MBL International | TS-M520-2 |
| Anti-mouse CD8-FITC | KT15 | MBL International | D271-4 |
| **Drugs or antibodies for treatment** | **Clone** | **Vendor** | **Identifier** |
| Anti-mouse 4-1BB (CD137) | 3H3 | BioXcell | BE0239 |
| Anti-mouse PD-1 | RMP1-14 | BioXcell | BP0146 |
| Anti-mouse CD3 | 17A2 | Bio Xcell | BE0002 |
| 5-Fluorouracil | NA | Intas Pharma-ceuticals | DB00544 |
| **Mouse** | **Age** | **Vendor** | **Identifier** |
| BALB/cJ | 6-8 weeks | The Jackson Laboratory | 000651 |
| C57BL/6 | 6-8 weeks | Charles River | 027 |

References:

Beyranvand Nejad, E., van der Sluis, T. C., van Duikeren, S., Yagita, H., Janssen, G. M., van Veelen, P. A., Melief, C. J., van der Burg, S. H., and Arens, R. (2016). Tumor Eradication by Cisplatin Is Sustained by CD80/86-Mediated Costimulation of CD8+ T Cells. Cancer research 76, 6017-6029.

Buchan, S. L., Dou, L., Remer, M., Booth, S. G., Dunn, S. N., Lai, C., Semmrich, M., Teige, I., Martensson, L., Penfold, C. A., et al. (2018). Antibodies to Costimulatory Receptor 4-1BB Enhance Anti-tumor Immunity via T Regulatory Cell Depletion and Promotion of CD8 T Cell Effector Function. Immunity 49, 958-970 e957.

Cao, Z., Zhang, Z., Huang, Z., Wang, R., Yang, A., Liao, L., and Du, J. (2014). Antitumor and immunomodulatory effects of low-dose 5-FU on hepatoma 22 tumor-bearing mice. Oncology letters 7, 1260-1264.

Chambers, B. J., Salcedo, M., and Ljunggren, H. G. (1996). Triggering of natural killer cells by the costimulatory molecule CD80 (B7-1). Immunity 5, 311-317.

Chester, C., Ambulkar, S., and Kohrt, H. E. (2016). 4-1BB agonism: adding the accelerator to cancer immunotherapy. Cancer immunology, immunotherapy: CII 65, 1243-1248.

Cochran, A. J., Huang, R. R., Lee, J., Itakura, E., Leong, S. P., and Essner, R. (2006). Tumour-induced immune modulation of sentinel lymph nodes. Nature reviews Immunology 6, 659-670.

Cochran, A. J., Morton, D. L., Stern, S., Lana, A. M., Essner, R., and Wen, D. R. (2001). Sentinel lymph nodes show profound downregulation of antigen-presenting cells of the paracortex: implications for tumor biology and treatment. Modern pathology: an official journal of the United States and Canadian Academy of Pathology, Inc 14, 604-608.

DeVita, V. T., Jr., and Chu, E. (2008). A history of cancer chemotherapy. Cancer research 68, 8643-8653.

Emens, L. A., and Middleton, G. (2015). The interplay of immunotherapy and chemotherapy: harnessing potential synergies. Cancer immunology research 3, 436-443.

Fend, L., Yamazaki, T., Remy, C., Fahrner, C., Gantzer, M., Nourtier, V., Preville, X., Quemeneur, E., Kepp, O., Adam, J., et al. (2017). Immune Checkpoint Blockade, Immunogenic Chemotherapy or IFN-alpha Blockade Boost the Local and Abscopal Effects of Oncolytic Virotherapy. Cancer research 77, 4146-4157.
Fisher, B., and Fisher, E. R. (1971). Studies concerning the regional lymph node in cancer. I. Initiation of immunity. Cancer 27, 1001-1004.
Fransen, M. F., Schoonderwoerd, M., Knopf, P., Camps, M. G., Hawinkels, L. J., Kneilling, M., van Hall, T., and Ossendorp, F. (2018). Tumor-draining lymph nodes are pivotal in PD-1/PD-L1 checkpoint therapy. JCI insight 3.
Galluzzi, L., Buque, A., Kepp, O., Zitvogel, L., and Kroemer, G. (2017). Immunogenic cell death in cancer and infectious disease. Nature reviews Immunology 17, 97-111.
Ghiringhelli, F., Menard, C., Puig, P. E., Ladoire, S., Roux, S., Martin, F., Solary, E., Le Cesne, A., Zitvogel, L., and Chauffert, B. (2007). Metronomic cyclophosphamide regimen selectively depletes CD4+CD25+ regulatory T cells and restores T and NK effector functions in end stage cancer patients. Cancer immunology, immunotherapy: CII 56, 641-648.
Gide, T. N., Wilmott, J. S., Scolyer, R. A., and Long, G. V. (2018). Primary and Acquired Resistance to Immune Checkpoint Inhibitors in Metastatic Melanoma. Clinical cancer research: an official journal of the American Association for Cancer Research 24, 1260-1270.
Ito, M., Minamiya, Y., Kawai, H., Saito, S., Saito, H., Nakagawa, T., Imai, K., Hirokawa, M., and Ogawa, J. (2006). Tumor-derived TGFbeta-1 induces dendritic cell apoptosis in the sentinel lymph node. Journal of immunology 176, 5637-5643.
Jeanbart, L., Ballester, M., de Titta, A., Corthesy, P., Romero, P., Hubbell, J. A., and Swartz, M. A. (2014). Enhancing efficacy of anticancer vaccines by targeted delivery to tumor-draining lymph nodes. Cancer immunology research 2, 436-447.
Kamphorst, A. O., Wieland, A., Nasti, T., Yang, S., Zhang, R., Barber, D. L., Konieczny, B. T., Daugherty, C. Z., Koenig, L., Yu, K., et al. (2017). Rescue of exhausted CD8 T cells by PD-1-targeted therapies is CD28-dependent. Science 355, 1423-1427.
Kareva, I. (2017). A Combination of Immune Checkpoint Inhibition with Metronomic Chemotherapy as a Way of Targeting Therapy-Resistant Cancer Cells. International journal of molecular sciences 18.
Karlsson, M., Marits, P., Dahl, K., Dagoo, T., Enerback, S., Thorn, M., and Winqvist, O. (2010). Pilot study of sentinel-node-based adoptive immunotherapy in advanced colorectal cancer. Annals of surgical oncology 17, 1747-1757.
Khosravianfar, N., Hadjati, J., Namdar, A., Boghozian, R., Hafezi, M., Ashourpour, M., Kheshtchin, N., Banitalebi, M., Mirzaei, R., and Razavi, S. A. (2018). Myeloid-derived Suppressive Cells Elimination by 5-Fluorouracil Increased Dendritic Cell-based Vaccine Function and Improved Immunity in Tumor Mice. Iranian journal of allergy, asthma, and immunology 17, 47-55.
Kumar, V., Patel, S., Tcyganov, E., and Gabrilovich, D. I. (2016). The Nature of Myeloid-Derived Suppressive Cells in the Tumor Microenvironment. Trends in immunology 37, 208-220.
Lake, R. A., O'Hehir, R. E., Verhoef, A., and Lamb, J. R. (1993). CD28 mRNA rapidly decays when activated T cells are functionally anergized with specific peptide. International immunology 5, 461-466.
Lanier, L. L., O'Fallon, S., Somoza, C., Phillips, J. H., Linsley, P. S., Okumura, K., Ito, D., and Azuma, M. (1995). CD80 (B7) and CD86 (B70) provide similar costimulatory signals for T cell proliferation, cytokine production, and generation of CTL. Journal of immunology 154, 97-105.
Le, D. T., Durham, J. N., Smith, K. N., Wang, H., Bartlett, B. R., Aulakh, L. K., Lu, S., Kemberling, H., Wilt, C., Luber, B. S., et al. (2017). Mismatch repair deficiency predicts response of solid tumors to PD-1 blockade. Science 357, 409-413.
Lee, C. K., Man, J., Lord, S., Links, M., Gebski, V., Mok, T., and Yang, J. C. (2017). Checkpoint Inhibitors in Metastatic EGFR-Mutated Non-Small Cell Lung Cancer-A Meta-Analysis. Journal of thoracic oncology: official publication of the International Association for the Study of Lung Cancer 12, 403-407.
Linterman, M. A., Denton, A. E., Divekar, D. P., Zvetkova, I., Kane, L., Ferreira, C., Veldhoen, M., Clare, S., Dougan, G., Espeli, M., et al. (2014). CD28 expression is required after T cell priming for helper T cell responses and protective immunity to infection. eLife 3.
Li, J., Blake, S. J., Yong, M. C., Harjunpaa, H., Ngiow, S. F., Takeda, K., Young, A., O'Donnell, J. S., Allen, S., Smyth, M. J., et al. (2016). Improved Efficacy of Neoadjuvant Compared to Adjuvant Immunotherapy to Eradicate Metastatic Disease. Cancer discovery 6, 1382-1399.
Lutsiak, M. E., Semnani, R. T., De Pascalis, R., Kashmiri, S. V., Schlom, J., and Sabzevari, H. (2005). Inhibition of CD4 (+) 25+T regulatory cell function implicated in enhanced immune response by low-dose cyclophosphamide. Blood 105, 2862-2868.
Marzo, A. L., Lake, R. A., Lo, D., Sherman, L., McWilliam, A., Nelson, D., Robinson, B. W., and Scott, B. (1999). Tumor antigens are constitutively presented in the draining lymph nodes. Journal of immunology 162, 5838-5845.
Michels, T., Shurin, G. V., Naiditch, H., Sevko, A., Umansky, V., and Shurin, M. R. (2012). Paclitaxel promotes differentiation of myeloid-derived suppressor cells into dendritic cells in vitro in a TLR4-independent manner. Journal of immunotoxicology 9, 292-300.
Munn, D. H., and Mellor, A. L. (2006). The tumor-draining lymph node as an immune-privileged site. Immunological reviews 213, 146-158.
Murthy, V., Katzman, D. P., Tsay, J. J., Bessich, J. L., Michaud, G. C., Rafeq, S., Minehart, J., Mangalick, K., de Lafaille, M. A. C., Goparaju, C., et al. (2019). Tumor-draining lymph nodes demonstrate a suppressive immunophenotype in patients with non-small cell lung cancer assessed by endobronchial ultrasound-guided transbronchial needle aspiration: A pilot study. Lung cancer 137, 94-99.
Pfirschke, C., Engblom, C., Rickelt, S., Cortez-Retamozo, V., Garris, C., Pucci, F., Yamazaki, T., Poirier-Colame, V., Newton, A., Redouane, Y., et al. (2016). Immunogenic Chemotherapy Sensitizes Tumors to Checkpoint Blockade Therapy. Immunity 44, 343-354.
Rizvi, N. A., Mazieres, J., Planchard, D., Stinchcombe, T. E., Dy, G. K., Antonia, S. J., Horn, L., Lena, H., Minenza, E., Mennecier, B., et al. (2015). Activity and safety of nivolumab, an anti-PD-1 immune checkpoint inhibitor, for patients with advanced, refractory squamous non-small-cell lung cancer (CheckMate 063): a phase 2, single-arm trial. The Lancet Oncology 16, 257-265.
Robert, C., Thomas, L., Bondarenko, I., O'Day, S., Weber, J., Garbe, C., Lebbe, C., Baurain, J. F., Testori, A., Grob, J. J., et al. (2011). Ipilimumab plus dacarbazine for previously untreated metastatic melanoma. The New England journal of medicine 364, 2517-2526.

Samanta, D., Park, Y., Ni, X., Li, H., Zahnow, C. A., Gabrielson, E., Pan, F., and Semenza, G. L. (2018). Chemotherapy induces enrichment of CD47 (+)/CD73 (+)/PDL1 (+) immune evasive triple-negative breast cancer cells. Proceedings of the National Academy of Sciences of the United States of America 115, E1239-E1248.

Scrimieri, F., Askew, D., Corn, D. J., Eid, S., Bobanga, I. D., Bjelac, J. A., Tsao, M. L., Allen, F., Othman, Y. S., Wang, S. C., et al. (2013). Murine leukemia virus envelope gp70 is a shared biomarker for the high-sensitivity quantification of murine tumor burden. Oncoimmunology 2, e26889.

Sharma, P., Hu-Lieskovan, S., Wargo, J. A., and Ribas, A. (2017). Primary, Adaptive, and Acquired Resistance to Cancer Immunotherapy. Cell 168, 707-723.

Shu, S., Cochran, A. J., Huang, R. R., Morton, D. L., and Maecker, H. T. (2006). Immune responses in the draining lymph nodes against cancer: implications for immunotherapy. Cancer metastasis reviews 25, 233-242.

Shuang, Z.-Y., Mao, Y.-Z., Liu, Y.-C., Lin, G.-H., Wang, J.-C., Wang, J., and Li, S.-P. (2017). The tumor-draining lymph nodes are immunosuppressed in patients with hepatocellular carcinoma. Translational Cancer Research 6, 1188-1196.

Singh, N. P., Yolcu, E. S., Taylor, D. D., Gercel-Taylor, C., Metzinger, D. S., Dreisbach, S. K., and Shirwan, H. (2003). A novel approach to cancer immunotherapy: tumor cells decorated with CD80 generate effective antitumor immunity. Cancer research 63, 4067-4073.

Song, M. K., Park, M. Y., and Sung, M. K. (2013). 5-Fluorouracil-induced changes of intestinal integrity biomarkers in BALB/c mice. Journal of cancer prevention 18, 322-329.

Tesniere, A., Schlemmer, F., Boige, V., Kepp, O., Martins, I., Ghiringhelli, F., Aymeric, L., Michaud, M., Apetoh, L., Barault, L., et al. (2010). Immunogenic death of colon cancer cells treated with oxaliplatin. Oncogene 29, 482-491.

Toki, M. I., Kumar, D., Ahmed, F. S., Rimm, D. L., and Xu, M. L. (2020). Benign Lymph Node Microenvironment is Associated with Response to Immunotherapy. Precision Clinical Medicine.

Topalian, S. L., Hodi, F. S., Brahmer, J. R., Gettinger, S. N., Smith, D. C., McDermott, D. F., Powderly, J. D., Carvajal, R. D., Sosman, J. A., Atkins, M. B., et al. (2012). Safety, activity, and immune correlates of anti-PD-1 antibody in cancer. The New England journal of medicine 366, 2443-2454.

Vallejo, A. N., Brandes, J. C., Weyand, C. M., and Goronzy, J. J. (1999). Modulation of CD28 expression: distinct regulatory pathways during activation and replicative senescence. Journal of immunology 162, 6572-6579.

Veglia, F., Perego, M., and Gabrilovich, D. (2018). Myeloid-derived suppressor cells coming of age. Nature immunology 19, 108-119.

Vincent, J., Mignot, G., Chalmin, F., Ladoire, S., Bruchard, M., Chevriaux, A., Martin, F., Apetoh, L., Rebe, C., and Ghiringhelli, F. (2010). 5-Fluorouracil selectively kills tumor-associated myeloid-derived suppressor cells resulting in enhanced T cell-dependent antitumor immunity. Cancer research 70, 3052-3061.

Wang, N., Wang, Z., Xu, Z., Chen, X., and Zhu, G. (2018). A Cisplatin-Loaded Immunochemotherapeutic Nanohybrid Bearing Immune Checkpoint Inhibitors for Enhanced Cervical Cancer Therapy. Angewandte Chemie 57, 3426-3430.

Watanabe, S., Deguchi, K., Zheng, R., Tamai, H., Wang, L. X., Cohen, P. A., and Shu, S. (2008). Tumor-induced CD11b+Gr-1+ myeloid cells suppress T cell sensitization in tumor-draining lymph nodes. Journal of immunology 181, 3291-3300.

Wu, X., Zhang, H., Xing, Q., Cui, J., Li, J., Li, Y., Tan, Y., and Wang, S. (2014). PD-1(+) CD8(+) T cells are exhausted in tumours and functional in draining lymph nodes of colorectal cancer patients. British journal of cancer 111, 1391-1399.

Zhang, L., Dermawan, K., Jin, M., Liu, R., Zheng, H., Xu, L., Zhang, Y., Cai, Y., Chu, Y., and Xiong, S. (2008). Differential impairment of regulatory T cells rather than effector T cells by paclitaxel-based chemotherapy. Clinical immunology 129, 219-229.

Zhao, X., and Subramanian, S. (2017). Intrinsic Resistance of Solid Tumors to Immune Checkpoint Blockade Therapy. Cancer research 77, 817-822.

Example 3: Modified Tumor-Derived Extracellular Vesicles Prevent Secondary Tumor Formation Tumor recurrence after surgery and other treatments is a major cause of death in colon cancer patients. In Example 1, we demonstrated that the modified tumor-derived extracellular vesicles (EVs) are immunogenic in primary tumors. In the present Example, the inventors investigated the effects of modified tumor-derived EVs on preventing secondary tumor formation. To do so, they created a mouse model in which primary tumors are induced and surgically resected before any treatment, and then tumor-derived EVs are used as a preventive treatment before secondary tumor induction. They found that mice treated by the modified tumor-derived EVs are resistant to secondary tumor formation. Further, they tested the dose-dependent effects of modified tumor-derived EVs on tumor prevention and found that 10 μg/injection of the modified tumor-derived EVs generated a superior effect than 5 ug/injection, but that further increases in dose did not increase the protection.

Materials and Methods:

Cell Cultures

The murine CRC cell line CT26 (purchased from American Type Culture Collection (ATCC)) was used for this study and was authenticated by STR profiling. CT26 cells were maintained in complete RPMI-1640 medium (GIBCO BRL), supplemented with 10% heat-inactivated FBS (Thermo Fisher Scientific), 100 IU/mL penicillin, and 100 μg/mL streptomycin (Invitrogen Life Technologies).

Mice

Wild type BALB/c mice (6-8 weeks old, Jackson Laboratory) were used for animal studies. All mice were kept in a specific pathogen-free facility with fully autoclaved cages to minimize non-tumor specific immune activation. Animal studies were approved by the institutional animal care and use committee (IACUC). All mice are female. We don't expect the any influence of gender on our study aims.

Subcutaneous Tumor Induction

For the subcutaneous syngeneic model, the cells were harvested at low passages, washed, and resuspended in Matrigel matrix (Corning Inc.) before injection. Mice were shaved right before injection. CT26 cells ($2\times10^5$ cells/injection) were inoculated subcutaneously into the right hind-flank of 6- to 8-week-old female BALB/c. Tumor volume was calculated according to the formula (length× width$^2$)/2. Mice were divided into different experimental groups at random when tumors reached a specific size.

Subcutaneous Tumor Resection

Primary tumors were resected when they reached the indicated volume as shown in the experimental schematics in each figure. Tumor-bearing mice were anesthetized with Ketamine (100 mg/kg) and Xylazine (10 mg/kg) by intraperitoneal injection. To minimize animal pain, we administrated Buprenorphine (slow-releasing, 2 mg/kg) subcutaneously 2 hours before anesthesia. Mice were prepared by removing hair from the skin region over the tumor. We prepared the skin by wiping with iodine prep pads and then alcohol prep pads. Resections were performed by elliptical incisions, 5 mm left to the subcutaneous tumors. With iris scissors, we separated the capsule of subcutaneous tumors from the surrounding connective tissue to isolate and resect intact tumors. Once tumors were removed from the adjacent fascia, the incisions were sutured with 5/0 vicryl ties (polyglactin 910, Ethicon). For tumor rechallenge, we inoculated the secondary tumor (CT26: $5\times10^5$ cells/injection) to the surgical site to mimic tumor recurrence.

Isolation of Extracellular Vesicles (EVs)

For EVs isolation from cell culture supernatants, cells were cultured in media supplemented with 10% exosome depleted FBS (Gibco). Supernatants were collected from 24 h cell cultures and EVs were purified by a standard differential centrifugation protocol. In brief, culture supernatants were centrifuged at 300 g for 10 min to remove cells. The supernatant was then centrifuged at 3,000 g for 10 min to remove dead cells. Debris was pelleted after centrifugation at 10,000 g for 30 min. Supernatants were then centrifuged at 100,000 g for 70 min at 4° C. (Beckman Coulter). The pelleted EVs were suspended in PBS and collected by ultracentrifugation at 100,000 g for 70 min at 4° C. again to minimize protein.

Results:

The Tumor Prevention Effect of Modified Tumor-Derived EVs is Dose-Dependent

We injected a different amount of modified tumor-derived EVs (5 ug/dose, 10 ug/dose, and 20 ug/dose) to naïve mice on day 0 and day 4. On day 14, we induced subcutaneous tumors in those animals. Our data indicated that, on day 28, the mice treated by 5 ug/dose modified tumor-derived EVs had bigger tumors than mice treated by 10 ug/dose modified tumor-derived EVs. However, there is no significant difference between the 10 ug/dose and the 20 ug/dose groups.

Modified Tumor-Derived EVs Limit Secondary Tumor Growth

To represent tumor recurrence in human CRC patients, we established a mouse model in which we resected the primary tumor and induced the secondary tumor in the same animal. After the primary tumor resection, we treated the mice with wild-type tumor-derived EVs and modified tumor-derived EVs. Then the secondary tumor was induced. At the end of follow-up, we measured the secondary tumor volume and observed that mice treated with modified tumor-derived EVs had smaller secondary tumors than other groups.

Conclusions:

Our data showed that the modified tumor-derived EVs limit secondary tumor growth. The tumor protection effect is dose-dependent.

The above description, attached figures, and claims listed below are intended to be illustrative and not limiting of this invention. In light of the invention described herein, many themes and variations to this invention will be suggested to one skilled in the art. All such themes and variations are within the contemplation hereof. For instance, while this invention has been described in conjunction with the various exemplary embodiments outlined above and in the below claims, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A composition comprising: modified tumor-derived extracellular vesicles (EVs) isolated from a tumor cell lacking expression of an immune suppressive factor, wherein the immune suppressive factor is miR-424, and wherein the isolated modified tumor-derived EVs are suspended in a pharmaceutically acceptable carrier; and one or more checkpoint inhibitor.

2. The composition of claim 1, wherein the EVs are exosomes or microvesicles.

3. The composition of claim 1, wherein the EVs are about 30 to about 300 nanometers in diameter.

4. The composition of claim 1, wherein the EVs are isolated from a tumor cell that has been modified to inhibit expression of the immune suppressive factor.

5. The composition of claim 1, wherein the tumor cell is a cultured tumor cell or a tumor organoid.

6. The composition of claim 5, wherein the tumor cell is selected from the group consisting of a colorectal cancer cell, breast cancer cell, endometrial cancer cell, prostate cancer cell, lung cancer cell, melanoma cell, and pancreatic cancer cell.

7. The composition of claim 1, wherein the EVs comprise one or more exogenous antigens.

8. The composition of claim 1, wherein the tumor or tumor organoid cell has been modified to inhibit expression of the mi-424 immune suppressive factor by one of the following:

a) transducing the tumor cell with an anti-miR-424 expression vector, b) transfecting the tumor cells with an anti-miRNA-424 oligo, or c) knocking out the miR-424 gene from the tumor cell using CRISPR/Cas9 genome editing.

9. The composition of claim 1, wherein the one or more checkpoint inhibitors are selected from the group consisting of a PD-1 inhibitor, a PD-L1 inhibitor, and a CTLA-4 inhibitor.

10. The composition of claim 1, wherein the EVs are present at a concentration of at least 50 μg/mL.

11. The composition of claim 1, wherein the modified tumor-derived EVs comprise two or more tumor-derived EVs, and wherein the two or more tumor-derived EVs are from different individual tumors.

* * * * *